(12) United States Patent
Gregory et al.

(10) Patent No.: US 9,090,657 B2
(45) Date of Patent: *Jul. 28, 2015

(54) COMPOUND AND METHODS FOR ITS PRODUCTION

(75) Inventors: Matthew Alan Gregory, Cambridge (GB); Steven James Moss, Cambridge (GB); Barrie Wilkinson, Cambridge (GB)

(73) Assignee: NEUROVIVE PHARMACEUTICAL AB, Lund (SE)

( * ) Notice: Subject to any disclaimer, the term of this patent is extended or adjusted under 35 U.S.C. 154(b) by 465 days.

This patent is subject to a terminal disclaimer.

(21) Appl. No.: 13/433,944

(22) Filed: Mar. 29, 2012

(65) Prior Publication Data
US 2012/0251581 A1 Oct. 4, 2012

(30) Foreign Application Priority Data

Mar. 29, 2011 (GB) .................................. 1105293.3
Aug. 8, 2011 (GB) .................................. 1113629.8
Feb. 7, 2012 (GB) .................................. 1202060.8

(51) Int. Cl.
| | |
|---|---|
| *C07D 498/04* | (2006.01) |
| *C07K 5/065* | (2006.01) |
| *A61K 38/06* | (2006.01) |
| *C07K 5/083* | (2006.01) |
| *C07K 5/06* | (2006.01) |
| *C07D 498/06* | (2006.01) |

(52) U.S. Cl.
CPC ............. *C07K 5/06078* (2013.01); *A61K 38/06* (2013.01); *C07D 498/04* (2013.01); *C07D 498/06* (2013.01); *C07K 5/06191* (2013.01); *C07K 5/0808* (2013.01)

(58) Field of Classification Search
None
See application file for complete search history.

(56) References Cited

FOREIGN PATENT DOCUMENTS

| WO | 2006/138507 | 12/2006 |
|---|---|---|
| WO | 2011/098805 | 8/2011 |
| WO | 2011/098808 | 8/2011 |
| WO | 2011/098809 | 8/2011 |

OTHER PUBLICATIONS

Grujic. Rapid Communications in Mass Spectometry, 2008, 22, 67-74.*
Banteli, R., et al. "Synthesis of derivatives of the novel cyclophilin-binding immunosuppressant sanglifehrin A with reduced numbers of polar functions." Bioorg Med Chem Lett. Jun. 18, 2001;11(12):1609-12.
Metternich, R., et al. "Toward a Total Synthesis of the Immunosuppressant Sanglifehrin. A. Preparation of Two Relay Compounds by Degradation and Their Use in the Reassembly of the Natural Product." J. Org. Chem. 1999;64:9632-9639.
Kallen, J., et al. "Structure of human cyclophilin A in complex with the novel immunosuppressant sanglifehrin A at 1.6 a resolution." J Biol Chem. Jun. 10, 2005;280(23):21965-71. Epub Mar. 16, 2005.
Fehr, T., et al. "Sanglifehrins A, B, C and D, novel cyclophilin-binding compounds isolated from Streptomyces sp. A92-308110. II. Structure elucidation, stereochemistry and physico-chemical properties." J Antibiot (Tokyo). May 1999;52(5):474-9.
Sanglier, J.J., et al. "Sanglifehrins A, B, C and D, novel cyclophilin-binding compounds isolated from Streptomyces. sp. A92-308110. I. Taxonomy, fermentation, isolation and biological activity." J Antibiot (Tokyo). May 1999;52(5):466-73.
Moss, S.J., et al. "Sangamides, a new class of cyclophilin-inhibiting host-targeted antivirals for treatment of HCV infection." Med. Chem. Commun. Oct. 2011;3:944-949.
Gregory, M.A., et al. "Preclinical characterization of naturally occurring polyketide cyclophilin inhibitors from the sanglifehrin family." Antimicrob Agents Chemother. May 2011;55(5):1975-81. Epub Mar. 7, 2011.
Moss, S.J., et al. "BC556, a potent, pan-genotypic, high barrier to resistance, second generation cyclophilin inhibitor for treatment of chronic HCV infection." Poster presentation, 47th Annual meeting of the European Associate for the study of liver, EASL—The international Liver Congress, Barcelona, Spain—Apr. 18-22, 2012.
Moss, S.J., et al. "Preclinical characterization of novel cyclophilin inhibitors based on the polyketide, sanglifehrin." Poster presentation. 46th Annual meeting of the European Association for the study of the liver, EASL—The international Liver Congress, Berlin, Germany—Mar. 30-Apr. 3, 2011.
Sedrani, R., et al. "Sanglifehrin-cyclophilin interaction: degradation work, synthetic macrocyclic analogues, X-ray crystal structure, and binding data." J Am Chem Soc. Apr. 2, 2003;125(13):3849-59.

* cited by examiner

*Primary Examiner* — Noble Jarrell
(74) *Attorney, Agent, or Firm* — Robert C. Netter, Jr.; Kathleen D. Rigaut; Dann, Dorfman, Herrell & Skillman

(57) ABSTRACT

There is provided inter alia a compound of formula (I):

Formula (I)

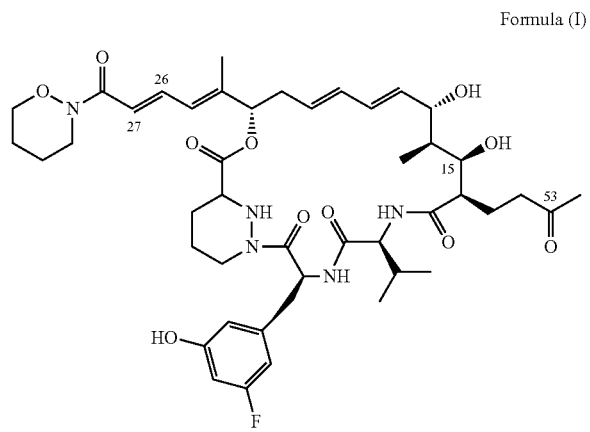

Figure 1:
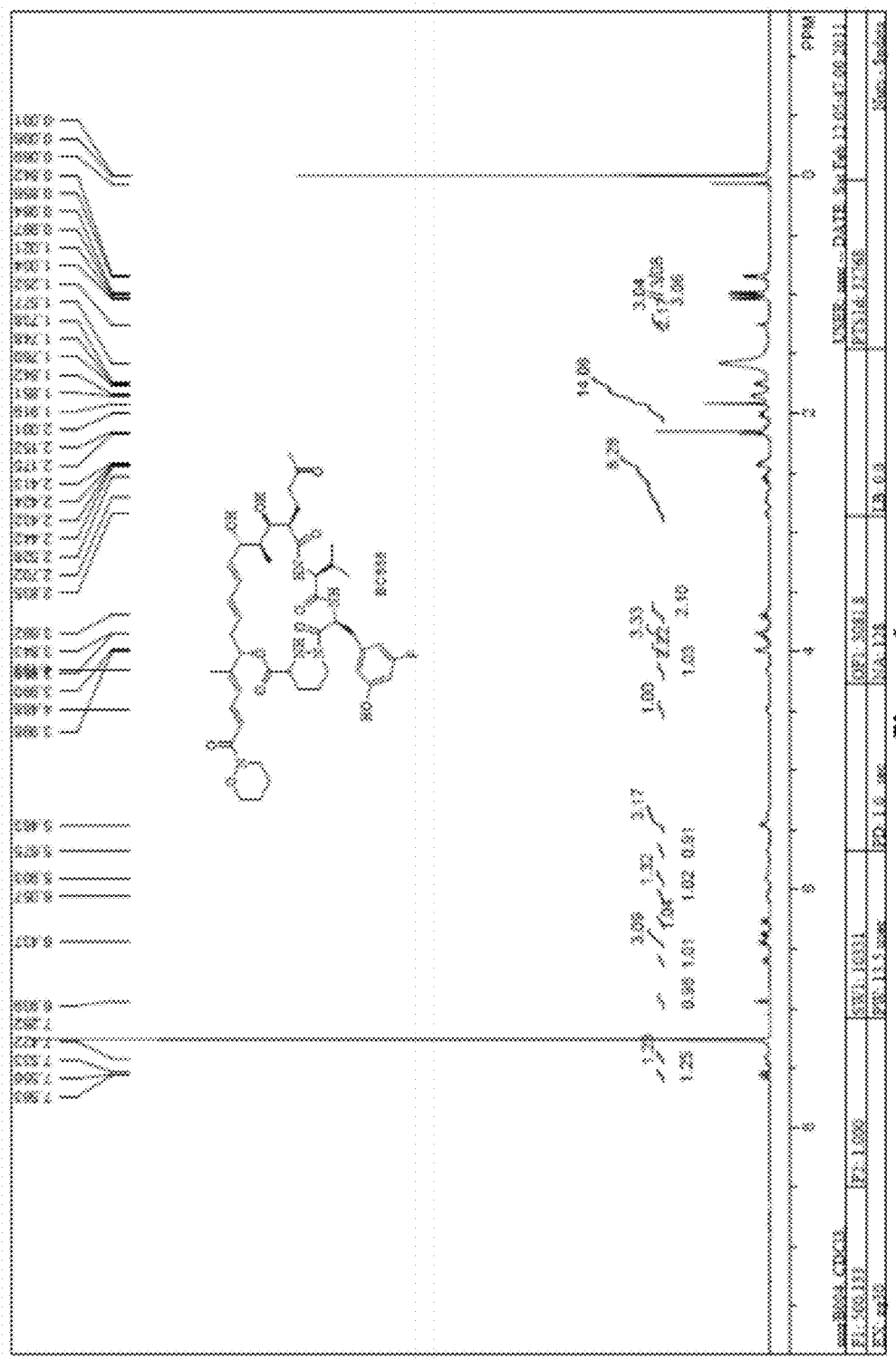

for use in treatment of viral infection or as an immunosuppressant.

8 Claims, 2 Drawing Sheets

COMPOUND AND METHODS FOR ITS PRODUCTION

The present application claims priority under 35 U.S.C. §119(a) to Great Britain Patent Application No. 1105293.3, filed Mar. 29, 2011; Great Britain Patent Application No. 1113629.8, filed Aug. 8, 2011; and Great Britain Patent Application No. 1202060.8, filed Feb. 7, 2012. The entire disclosure of each of the foregoing applications is incorporated by reference herein.

INTRODUCTION

The present invention relates to a sanglifehrin analogue, that is useful both as a cyclophilin inhibitor, e.g. in the treatment of viral infection by viruses such as Hepatitis C virus (HCV), Hepatitis B Virus (HBV) and Human Immunodeficiency Virus (HIV) and/or as an immunosuppressant e.g. for use in prophylaxis of transplant rejection and as an anti-inflammatory agent, e.g. for use in inflammatory disorders. The present invention also provides methods for its use in medicine, in particular for the treatment of HCV or HIV infection and for use as an immunosuppressant or anti-inflammatory agent, in diseases where inhibition of the Mitochondrial Permeability Transition Pore (mPTP) is useful such as muscular dystrophy or as an intermediate in the generation of further medicinally useful compounds.

BACKGROUND OF THE INVENTION

Hepatitis C

Hepatitis C virus (HCV) is a positive strand RNA virus, and infection is a leading cause of post-transfusional hepatitis. HCV is the most common chronic blood borne infection, and the leading cause of death from liver disease in United States. The World Health Organization estimates that there are more than 170 million chronic carriers of HCV infection, which is about 3% of the world population. Among the untreated HCV-infected patients, about 70%-85% develop chronic HCV infection, and are therefore at high risk to develop liver cirrhosis and hepatocellular carcinoma. In developed countries, 50-76% of all cases of liver cancer and two-thirds of all liver transplants are due to chronic HCV infection (Manns et al, 2007).

In addition to liver diseases, chronically infected patients may also develop other chronic HCV-related diseases, and serve as a source of transmission to others. HCV infection causes non-liver complications such as arthralgias (joint pain), skin rash, and internal organ damage predominantly to the kidney. HCV infection represents an important global health-care burden, and currently there is no vaccine available for hepatitis C (Strader et al., 2004; Jacobson et al. 2007; Manns et al., 2007; Pawlotsky, 2005; Zeuzem & Hermann, 2002).

Treatment of HCV

The current standard of care (SoC) is subcutaneous injections of pegylated interferon-α (pIFNα) and oral dosing of the antiviral drug ribavirin for a period of 24-48 weeks. Success in treatment is defined by sustained virologic response (SVR), which is defined by absence of HCV RNA in serum at the end of treatment period and 6 months later. Overall response rates to SoC depend mainly on genotype and pretreatment HCV RNA levels. Patients with genotype 2 and 3 are more likely to respond to SoC than patients infected with genotype 1 (Melnikova, 2008; Jacobson et al., 2007).

A significant number of HCV patients do not respond adequately to the SoC treatment, or cannot tolerate the therapy due to side effects, leading to frequent issues with completion of the full course. The overall clinical SVR rate of SoC is only around 50% (Melnikova, 2008). Development of resistance is another underlying factor for failure of treatment (Jacobson et al. et al. 2007). SoC is also contraindicated in some patients who are not considered candidates for treatment, such as patients with past significant episodes of depression or cardiac disease. Side effects of the SoC, which frequently lead to discontinuation of treatment, include a flu-like illness, fever, fatigue, haematological disease, anemia, leucopaenia, thrombocytopaenia, alopecia and depression (Manns et al., 2007).

Considering the side effects associated with the lengthy treatments using SoC, development of resistance, and suboptimum overall rate of success, more efficacious and safer new treatments are urgently needed for treatment of HCV infection. The objectives of new treatments include improved potency, improved toxicity profile, improved resistance profile, improved quality of life and the resulting improvement in patient compliance. HCV has a short life cycle and therefore development of drug resistance during drug therapy is common.

Novel, specifically targeted antiviral therapy for hepatitis C(STAT-C) also known as direct acting antiviral (DAA) drugs are being developed that target viral proteins such as viral RNA polymerase NS5B or viral protease NS3 (Jacobson et al, 2007; Parfieniuk et al., 2007). In addition, novel compounds also are being developed that target human proteins (e.g. cyclophilins) rather than viral targets, which might be expected to lead to a reduction in incidence of resistance during drug therapy (Manns et al., 2007; Pockros, 2008; Pawlotsky J-M, 2005).

Cyclophilin Inhibitors

Cyclophilins (CyP) are a family of cellular proteins that display peptidyl-prolyl cis-trans isomerase activity facilitating protein conformation changes and folding. CyPs are involved in cellular processes such as transcriptional regulation, immune response, protein secretion, and mitochondrial function. HCV virus recruits CyPs for its life cycle during human infection. Originally, it was thought that CyPs stimulate the RNA binding activity of the HCV non-structural protein NS5B RNA polymerase that promotes RNA replication, although several alternative hypotheses have been proposed including a requirement for CyP PPlase activity. Various isoforms of CyPs, including A and B, are believed to be involved in the HCV life cycle (Yang et al., 2008; Appel et al., 2006; Chatterji et al., 2009; Gaither et al., 2010). The ability to generate knockouts in mice (Colgan et al., 2000) and human T cells (Braaten and Luban, 2001) indicates that CyPA is optional for cell growth and survival. Similar results have been observed with disruption of CyPA homologues in bacteria (Herrler et al., 1994), *Neurospora* (Tropschug et al., 1989) and *Saccharomyces cerevisiae* (Dolinski et al. 1997). Therefore, inhibiting CyPs represent a novel and attractive host target for treating HCV infection, and a new potential addition to current SoC or STAT-C/DAA drugs, with the aim of increasing SVR, preventing emergence of resistance and lowering treatment side effects.

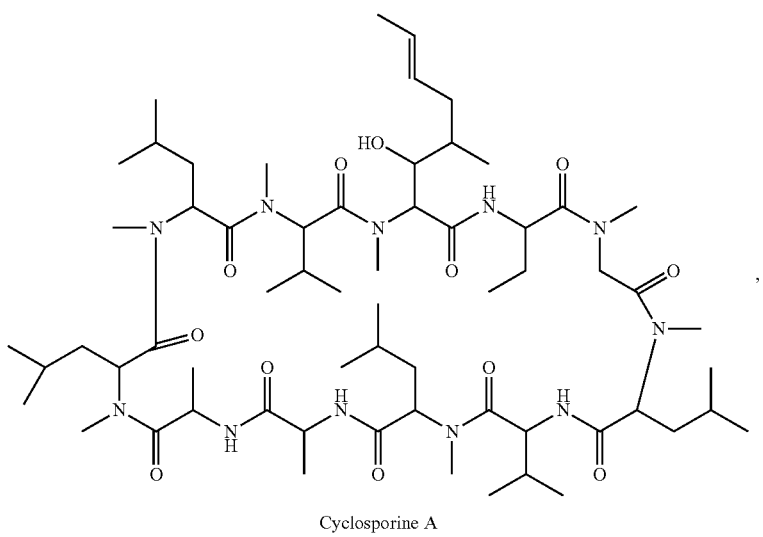
Cyclosporine A
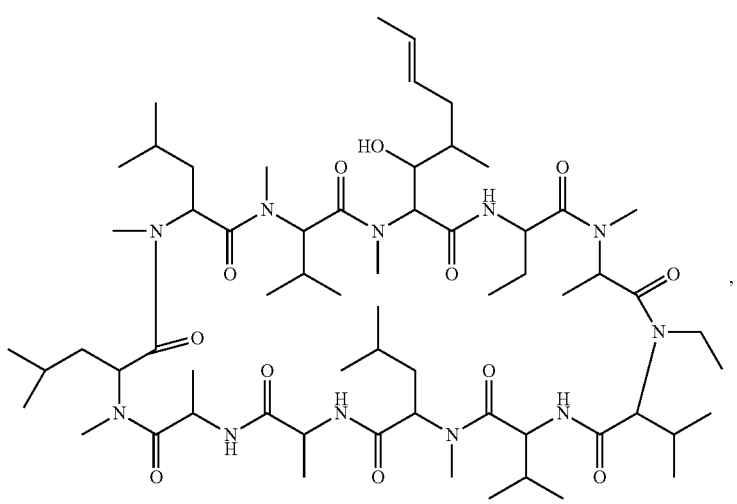
DEBIO-025
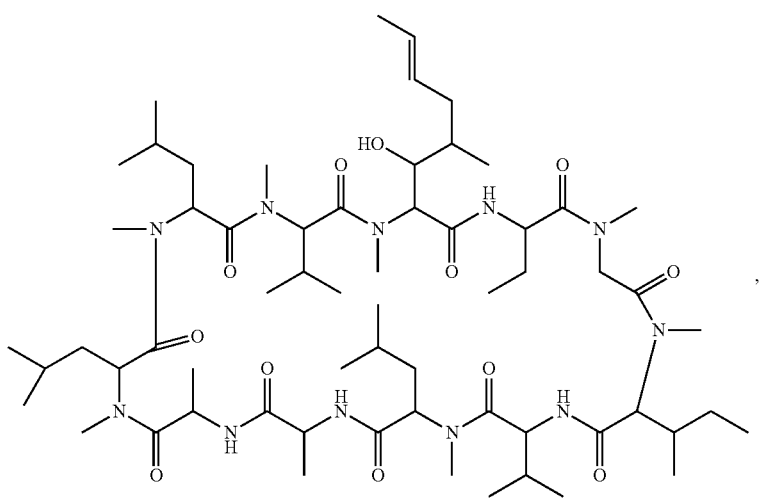
NIM-811

-continued

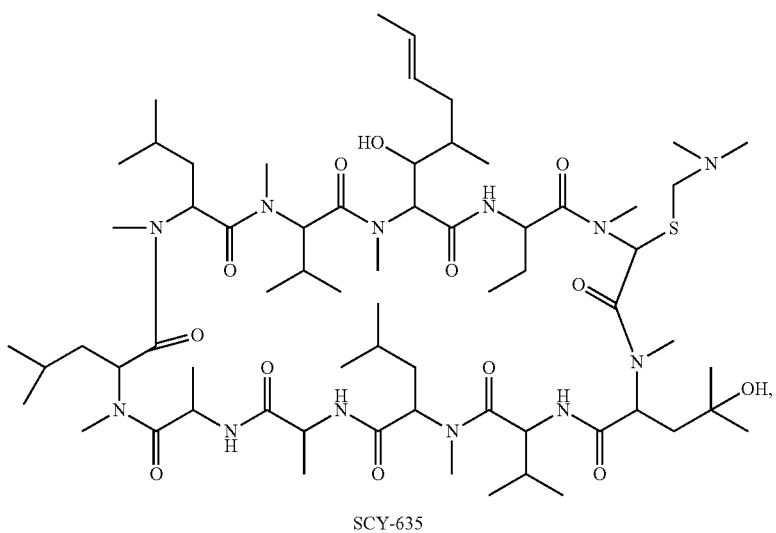

SCY-635

Cyclosporine A (Inoue et al. 2003) ("CsA") and its closely structurally related non-immunosuppressive clinical analogues DEBIO-025 (Paeshuyse et al. 2006; Flisiak et al. 2008), NIM811 (Mathy et al. 2008) and SCY-635 (Hopkins et al., 2009) are known to bind to cyclophilins, and as cyclophilin inhibitors have shown in vitro and clinical efficacy in the treatment of HCV infection (Crabbe et al., 2009; Flisiak et al. 2008; Mathy et al. 2008; Inoue et al., 2007; Ishii et al., 2006; Paeshuyse et al., 2006). Although earlier resistance studies on CsA showed mutations in HCV NS5B RNA polymerase and suggested that only cyclophilin B would be involved in the HCV replication process (Robida et al., 2007), recent studies have suggested an essential role for cyclophilin A in HCV replication (Chatterji et al. 2009; Yang et al., 2008). Considering that mutations in NS5A viral protein are also associated with CsA resistance and that NS5A interacts with both CyPA and CypB for their specific peptidyl-prolyl cis/trans isomerase (PPIase) activity, a role for both cyclophilins in viral life cycle is further suggested (Hanoulle et al., 2009).

The anti-HCV effect of cyclosporine analogues is independent of the immunosuppressive property, which is dependent on calcineurin. This indicated that the essential requirement for HCV activity is CyP binding and calcineurin binding is not needed. DEBIO-025, the most clinically advanced cyclophilin inhibitor for the treatment of HCV, has shown in vitro and in vivo potency against the four most prevalent HCV genotypes (genotypes 1, 2, 3, and 4). Resistance studies showed that mutations conferring resistance to DEBIO-025 were different from those reported for polymerase and protease inhibitors, and that there was no cross resistance with STAT-C/DAA resistant viral replicons. More importantly, DEBIO-025 also prevented the development of escape mutations that confer resistance to both protease and polymerase inhibitors (Crabbe et al., 2009).

However, the CsA-based cyclophilin inhibitors in clinical development have a number of issues, which are thought to be related to their shared structural class, including: certain adverse events that can lead to a withdrawal of therapy and have limited the clinical dose levels; variable pharmacokinetics that can lead to variable efficacy; and an increased risk of drug-drug interactions that can lead to dosing issues.

The most frequently occurring adverse events (AEs) in patients who received DEBIO-025 included jaundice, abdominal pain, vomiting, fatigue, and pyrexia. The most clinically important AEs were hyperbilirubinemia and reduction in platelet count (thrombocytopaenia). Peg-IFN can cause profound thrombocytopaenia and combination with DEBIO-025 could represent a significant clinical problem. Both an increase in bilirubin and decrease in platelets have also been described in early clinical studies with NIM-811 (Ke et al., 2009). Although the hyperbilirubinemia observed during DEBIO-025 clinical studies was reversed after treatment cessation, it was the cause for discontinuation of treatment in 4 out of 16 patients, and a reduction in dose levels for future trials. As the anti-viral effect of cyclophilin inhibitors in HCV is dose related, a reduction in dose has led to a reduction in anti-viral effect, and a number of later trials with CsA-based cyclophilin inhibitors have shown no or poor reductions in HCV viral load when dosed as a monotherapy (Lawitz et al., 2009; Hopkins et al., 2009; Nelson et al., 2009). DEBIO-025 and cyclosporine A are known to be inhibitors of biliary transporters such as bile salt export pumps and other hepatic transporters (especially OAT1B1/OAT1B3/MRP2/MRP3/cMOAT/ABCC2) (Crabbe et al., 2009). It has been suggested that the interaction with biliary transporters, in particular MRP2, may be the cause of the hyperbilirubinaemia seen at high dose levels of DEBIO-025 (Nelson et al., 2009, Wring et al., 2010). CsA class-related drug-drug interactions (DDIs) via inhibition of other drug transporters such as P-glycoprotein (Pgp/MDR1), BSEP, OAT1B1 and OAT1B3 (Konig et al., 2010) may also be a concern, potentially limiting certain combinations and use in some patients undergoing treatment for co-infections such as HIV (Seden et al., 2010).

Moreover, DEBIO-025 and cyclosporine A are substrates for metabolism by cytochrome P450 (especially CYP3A4), and are known to be substrates and inhibitors of human P-glycoprotein (MDR1) (Crabbe et al., 2009). Cyclosporine A has also been shown to be an inhibitor of CYP3A4 in vitro (Niwa et al., 2007). This indicates that there could be an increased risk of drug-drug interactions with other drugs that are CYP3A4 substrates, inducers or inhibitors such as for example ketoconazole, cimetidine and rifampicin. In addition, interactions are also expected with drugs that are subject to transport by P-glycoprotein (e.g. digoxin), which could cause severe drug-drug interactions in HCV patients receiving medical treatments for other concomitant diseases (Crabbe et al. 2009). CsA is also known to have highly variable pharmacokinetics, with early formulations showing oral bioavailability from 1-89% (Kapurtzak et al., 2004). Without expensive monitoring of patient blood levels, this can lead to increased prevalence of side effects due to increased plasma levels, or reduced clinical response due to lowered plasma levels.

Considering that inhibition of cyclophilins represent a promising new approach for treatment of HCV, there is a need for discovery and development of more potent and safer CyP inhibitors for use in combination therapy against HCV infection.

Sanglifehrins

Sanglifehrin A (SfA) and its natural congeners belong to a class of mixed non-ribosomal peptide/polyketides, produced by *Streptomyces* sp. A92-308110 (also known as DSM 9954) (see WO 97/02285), which were originally discovered on the basis of their high affinity to cyclophilin A (CyPA). SfA is the most abundant component in fermentation broths and exhibits approximately 20-fold higher affinity for CyPA compared to CsA. This has led to the suggestion that sanglifehrins could be useful for the treatment of HCV (WO2006/138507). Sanglifehrins have also been shown to exhibit a lower immunosuppressive activity than CsA when tested in vitro (Sanglier et al., 1999; Fehr et al., 1999). SfA binds with high affinity to the CsA binding site of CyPA (Kallen et al., 2005).

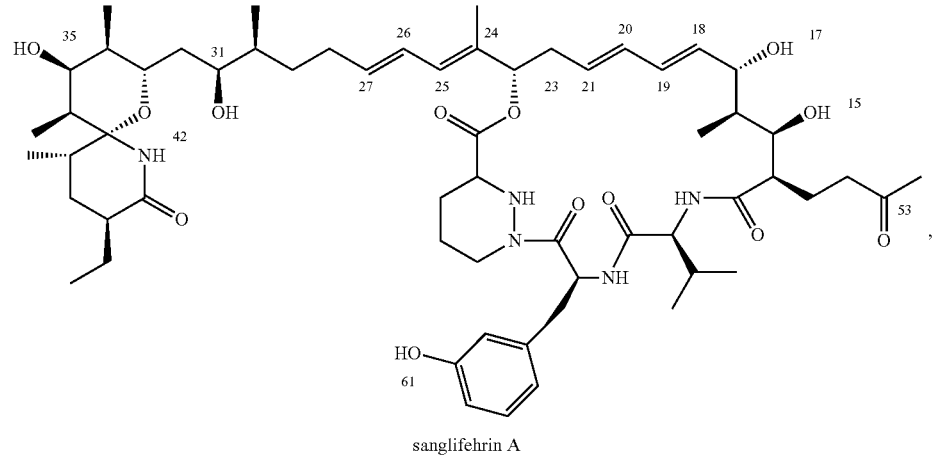

sanglifehrin A

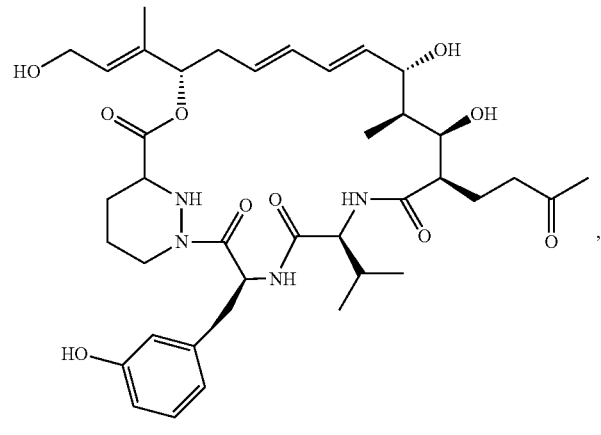

hydroxymacrocycle

-continued

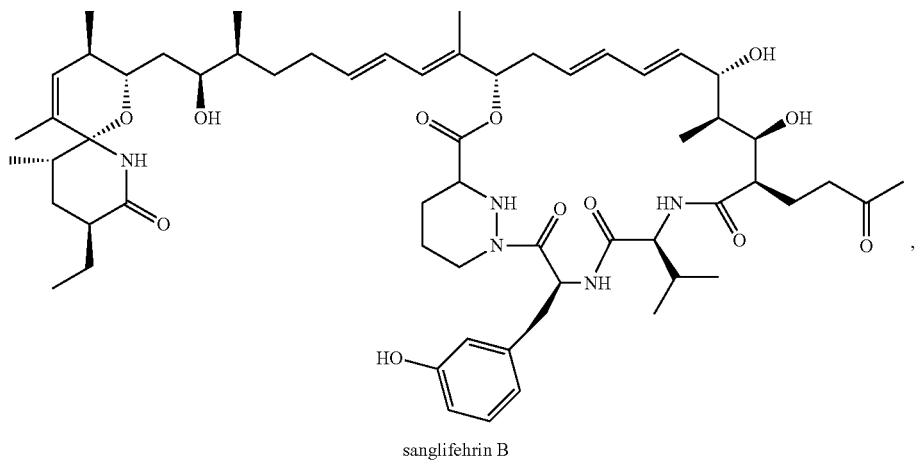

sanglifehrin B

Biosynthesis of Sanglifehrins

Sanglifehrins are biosynthesised by a mixed polyketide synthase (PKS)/Non-ribosomal peptide synthetase (NRPS) (see WO2010/034243). The 22-membered macrolide backbone consists of a polyketide carbon chain and a tripeptide chain. The peptide chain consists of one natural amino acid, valine, and two non-natural amino acids: (S)-meta-tyrosine and (S)-piperazic acid, linked by an amide bond. Hydroxylation of phenylalanine (either in situ on the NRPS or prior to biosynthesis) to generate (S)-meta-tyrosine is thought to occur via the gene product of sfaA.

Immunosuppressive Action of Sanglifehrins

The immunosuppressive mechanism of action of SfA is different to that of other known immunophilin-binding immunosuppressive drugs such as CsA, FK506 and rapamycin. SfA does not inhibit the phosphatase activity of calcineurin, the target of CsA (Zenke et al. 2001), instead its immunosuppressive activity has been attributed to the inhibition of interleukin-6 (Hartel et al., 2005), interleukin-12 (Steinschulte et al., 2003) and inhibition of interleukin-2-dependent T cell proliferation (Zhang & Liu, 2001). However, the molecular target and mechanism through which SfA exerts its immunosuppressive effect is hitherto unknown.

The molecular structure of SfA is complex and its interaction with CyPA is thought to be mediated largely by the macrocyclic portion of the molecule. In fact, a macrocyclic compound (hydroxymacrocycle) derived from oxidative cleavage of SfA has shown strong affinity for CyPA (Sedrani et al., 2003). X-ray crystal structure data has shown that the hydroxymacrocycle binds to the same active site of CyPA as CsA. Analogues based on the macrocycle moiety of SfA have also previously been shown to be devoid of immunosuppressive properties (Sedrani et al., 2003), providing opportunity for design of non-immunosuppressive CyP inhibitors for potential use in HCV therapy.

Converse to this, there is also an opportunity to develop immunosuppressive agents with low toxicity for use in such areas as prophylaxis of transplant rejection, autoimmune, inflammatory and respiratory disorders, including, but not limited to, Crohn's disease, Behcet syndrome, uveitis, psoriasis, atopic dermatitis, rheumatoid arthritis, nephritic syndrome, aplastic anaemia, biliary cirrhosis, asthma, pulmonary fibrosis, chronic obstructive pulmonary disease (COPD) and celiac disease. Sanglifehrins have been shown to have a novel mechanism of immunosuppressive activity (Zenke et al., 2001), potentially acting through dendritic cell chemokines (Immecke et al., 2011), and there is therefore an opportunity to develop agents with a mechanism of action different to current clinical agents, such as cyclosporine A, rapamycin and FK506. Sanglifehrin A has been shown to be 10 fold less potent than Cyclosporine A, so the ideal novel agent would have improved potency and/or therapeutic window.

Other Therapeutic Uses of Cyclophilin Inhibitors

Human Immunodeficiency Virus (HIV)

Cyclophilin inhibitors, such as CsA and DEBIO-025 have also shown potential utility in inhibition of HIV replication. The cyclophilin inhibitors are thought to interfere with function of CyPA during progression/completion of HIV reverse transcription (Ptak et al., 2008). However, when tested clinically, DEBIO-025 only reduced HIV-1 RNA levels and >1 log 10 copies/mL in nine and two patients respectively, whilst 27 of the treated patients showed no reduction in HIV-1 RNA levels (Steyn et al., 2006). Following this, DEBIO-025 was trialled in HCV/HIV coinfected patients, and showed better efficacy against HCV, and the HIV clinical trials were discontinued (see Watashi et al., 2010).

Treatment of HIV

More than 30 million people are infected by HIV-1 worldwide, with 3 million new cases each year. Treatment options have improved dramatically with the introduction of highly active antiretroviral therapy (HAART) (Schopman et al., 2010), By 2008, nearly 25 antiretroviral drugs had been licensed for treatment of HIV-1, including nine nucleoside reverse transcriptase inhibitors (NRTI), four non-nucleoside reverse transcriptase inhibitors (NNRTI), nine protease inhibitors (PI), one fusion inhibitor, one CCR5 inhibitor and one integrase inhibitor (Shafer and Schapiro, 2008). However, none of these current regimens leads to complete viral clearance, they can lead to severe side effects and antiviral resistance is still a major concern. Therefore, there still remains a need for new antiviral therapies, especially in mechanism of action classes where there are no approved drugs, such as is the case for cyclophilin inhibitors.

Hepatitis B Virus

Hepatitis B is a DNA virus of the family hepadnaviridae, and is the causative agent of Hepatitis B. As opposed to the cases with HCV and HIV, there have been very few published accounts of activity of cyclophilin inhibitors against Hepatitis B virus. Ptak et al. 2008 have described weak activity of Debio-025 against HBV (IC50 of 4.1 µM), whilst Xie et al., 2007 described some activity of CsA against HBV (IC50>1.3 µg/mL). This is in contrast to HIV and HCV, where there are numerous reports of nanomolar antiviral activity of cyclophilin inhibitors.

Treatment of HBV

HBV infects up to 400 million people worldwide and is a major cause of chronic viral hepatitis and hepatocellular carcinoma. As of 2008, there were six drugs licensed for the treatment of HBV; interferon alpha and pegylated interferon alpha, three nucleoside analogues (lamivudine, entecavir and telbivudine) and one nucleotide analogue (adefovir dipivoxil). However, due to high rates of resistance, poor tolerability and possible side effects, new therapeutic options are needed (Ferir et al., 2008).

Inhibition of the Mitochondrial Permeability Transition Pore (mPTP)

Opening of the high conductance permeability transition pores in mitochondria initiates onset of the mitochondrial permeability transition (MPT). This is a causative event, leading to necrosis and apoptosis in hepatocytes after oxidative stress, Ca2+ toxicity, and ischaemia/reperfusion. Inhibition of Cyclophilin D (also known as Cyclophilin F) by cyclophilin inhibitors has been shown to block opening of permeability transition pores and protects cell death after these stresses. Cyclophilin D inhibitors may therefore be useful in indications where the mPTP opening has been implicated, such as muscular dystrophy, in particular Ullrich congenital muscular dystrophy and Bethlem myopathy (Millay et al., 2008, WO2008/084368, Palma et al., 2009), multiple sclerosis (Forte et al., 2009), diabetes (Fujimoto et al., 2010), amyotrophic lateral sclerosis (Martin 2009), bipolar disorder (Kubota et al., 2010), Alzheimer's disease (Du and Yan, 2010), Huntington's disease (Perry et al., 2010), recovery after myocardial infarction (Gomez et al., 2007) and chronic alcohol consumption (King et al., 2010).

Further Therapeutic Uses

Cyclophilin inhibitors have potential activity against and therefore in the treatment of infections of other viruses, such as Varicella-zoster virus (Ptak et al., 2008), Influenza A virus (Liu et al., 2009), Severe acute respiratory syndrome coronavirus and other human and feline coronaviruses (Chen et al., 2005, Ptak et al., 2008), Dengue virus (Kaul et al., 2009), Yellow fever virus (Qing et al., 2009), West Nile virus (Qing et al., 2009), Western equine encephalitis virus (Qing et al., 2009), Cytomegalovirus (Kawasaki et al., 2007) and Vaccinia virus (Castro et al., 2003).

There are also reports of utility of cyclophilin inhibitors and cyclophilin inhibition in other therapeutic areas, such as in cancer (Han et al., 2009).

General Comments on Sanglifehrins

One of the issues in drug development of compounds such as sanglifehrins is rapid metabolism and glucuronidation, leading to low oral bioavailability. This can lead to an increased chance of food effect, more frequent incomplete release from the dosage form and higher interpatient variability.

Therefore there remains a need to identify novel cyclophilin inhibitors, which may have utility, particularly in the treatment of HCV infection, but also in the treatment of other disease areas where inhibition of cyclophilins may be useful, such as HIV infection, Muscular Dystrophy or aiding recovery after myocardial infarction or where immunosuppression or anti-inflammatory effect is useful. Preferably, such cyclophilin inhibitors have improved properties over the currently available cyclophilin inhibitors, including one or more of the following properties: longer half-life or increased oral bioavailability, possibly via reduced P450 metabolism and/or reduced glucuronidation, improved water solubility, improved potency against HCV, reduced toxicity (including hepatotoxicity), improved pharmacological profile, such as high exposure to target organ (e.g. liver in the case of HCV) and/or long half life (enabling less frequent dosing), reduced drug-drug interactions, such as via reduced levels of CYP3A4 metabolism and inhibition and reduced (Pgp) inhibition (enabling easier multi-drug combinations) and improved side-effect profile, such as low binding to MRP2, leading to a reduced chance of hyperbilirubinaemia, lower immunosuppressive effect, improved activity against resistant virus species, in particular CsA and CsA analogue (e.g. DEBIO-025) resistant virus species and higher therapeutic (and/or selectivity) index. The present invention discloses a novel sanglifehrin analogue which may have one or more of the above properties. In particular, the present invention discloses a novel mutasynthetic sanglifehrin analogue, which is anticipated to have reduced metabolism via P450 or glucuronidation, for example as shown by increased microsome half-life and/or reduced improved potency against HCV, for example as shown by a low replicon $EC_{50}$.

In addition, there is also a need to develop a novel immunosuppressive agent, which may have utility in the prophylaxis of transplant rejection, or in the treatment of autoimmune, inflammatory and respiratory disorders. Preferably, such an immunosuppressant will have improved properties over the known natural sanglifehrins, including one or more of the following properties: longer half-life or increased oral bioavailability, possibly via reduced P450 metabolism and/or reduced glucuronidation, improved water solubility, improved potency in immunosuppressive activity, such as might be seen in T-cell proliferation assays, reduced toxicity (including hepatotoxicity), improved pharmacological profile, such as high exposure to target organ and/or long half-life (enabling less frequent dosing), reduced drug-drug interactions, such as via reduced levels of CYP3A4 metabolism and inhibition and reduced (Pgp) inhibition (enabling easier multi-drug combinations) and improved side-effect profile. The present invention discloses a novel sanglifehrin analogue which may have one or more of the above properties. In particular, the present invention discloses a novel derivative, which has reduced metabolism via P450 or glucuronidation, for example as shown by increased microsome half-life and/or improved immunosuppressive potency, for example as shown by a low t-cell proliferation $IC_{50}$.

Thus, as can be seen from the Examples, the compound of the invention has the following favourable therapeutically relevant properties:

improved antiviral potency against HCV and HIV as compared with the prior art cyclophilin inhibitors Cyclosporin A, DEBIO-025 (alisporivir) and Sanglifehrin A;

reduced clearance and increased oral expose as compared with the prior art compound Sanglifehrin A;

more potent inhibition of CypA PPlase activity as compared with the prior art cyclophilin inhibitors Cyclosporin A, DEBIO-025 (alisporivir) and Sanglifehrin A;

improved side effect profile and reduced drug-drug interactions as demonstrated by reduced inhibition of bilirubin transporters (OATP-1B1, OATP-1B3, MRP2 and MRP3) and reduced inhibition of xenobiotic transporters (Pgp and BSEP).

SUMMARY OF THE INVENTION

The present invention provides a novel macrocyclic sanglifehrin analogue, which has been generated by semisynthetic modification of mutasynthetic sanglifehrins. This analogue may be generated by dihydroxylation of a mutasynthetic sanglifehrin, such as described in formula IIA and formula IIB, followed by cleavage to generate the aldehydic macrocycle, followed by further chemistry, including Horner-Emmons type reactions and other coupling reactions involving an aldehyde. As a result, the present invention provides a macrocyclic sanglifehrin analogue, methods for the preparation of this compound, and methods for the use of this compound in medicine or as an intermediate in the production of further compounds.

Therefore, in a first aspect, the present invention provides a macrocyclic sanglifehrin analogue according to formula (I) below, or a pharmaceutically acceptable salt thereof:

Formula (I)

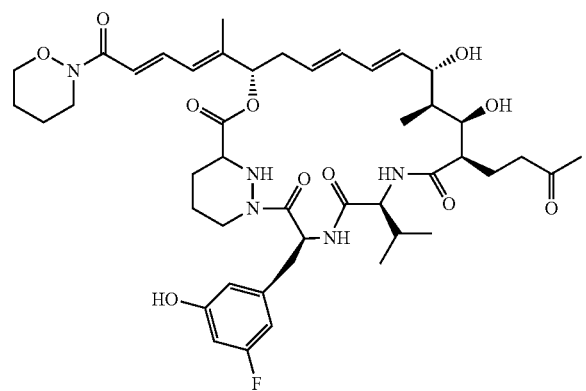

including any tautomer thereof; and including a methanol adduct thereof in which a ketal is formed by the combination of the C-53 keto and the C-15 hydroxyl group and methanol.

The above structure shows a representative tautomer and the invention embraces all tautomers of the compound of formula (I) for example a keto compound where an enol compound is illustrated and vice versa.

Specific tautomers that are included within the definition of formula (I) are those in which (i) the C-53 keto group forms a hemiketal with the C-15 hydroxyl, or (ii) the C-15 and C-17 hydroxyl can combine with the C-53 keto to form a ketal. All numberings use the system for the parent sanglifehrin A structure.

The compound of formula (I), or a pharmaceutically acceptable salt thereof, may optionally be present in the form of a pharmaceutically acceptable solvate, such as a hydrate.

In a further aspect, the present invention provides a macrocyclic sanglifehrin analogue according to formula (I) in solid crystalline form (Form I).

DEFINITIONS

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "sanglifehrin(s)" refers to chemical compounds that are structurally similar to sanglifehrin A but which differ slightly in composition (as in the replacement of one atom by another or in the presence or absence of a particular functional group), in particular those generated by fermentation of Streptomyces sp. A92-308110. Examples include the sanglifehrin-like compounds discussed in WO97/02285 and WO98/07743, such as sanglifehrin B.

As used herein the term "mutasynthetic sanglifehrin(s)" or "mutasynthetic sanglifehrin analogue(s)" refers to chemical compounds that are structurally similar to sanglifehrin A, B, C or D but which differ slightly in composition (as in the replacement of one or more atom by another or in the presence or absence of a particular functional group), in particular, those generated by fermentation of Streptomyces sp. A92-308110 or a mutant thereof, where the culture is fed with a meta-tyrosine analogue.

As used herein the term "meta-tyrosine analogue(s)" refers to chemical compounds that are structurally similar to meta-tyrosine but which differ slightly in composition (as in the replacement of one or more atom by another or in the presence or absence of a particular functional group), in particular, those described in formula (III).

As used herein, the term "macrocyclic analogue", "macrocyclic sanglifehrin analogue" or "macrocyclic sanglifehrin", refers to a compound referred to above as representing the invention in its broadest aspect, for example a compound according to formula (I) above, or a pharmaceutically acceptable salt thereof. These compounds are also referred to as "compounds of the invention" or "derivatives of sanglifehrin" or "sanglifehrin analogues" and these terms are used interchangeably in the present application.

As used herein, the term "HCV" refers to Hepatitis C Virus, a single stranded, RNA, enveloped virus in the viral family Flaviviridae.

As used herein, the term "HIV" refers to Human Immunodeficiency Virus, the causative agent of Human Acquired Immune Deficiency Syndrome.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Egorin et al. 2002).

The term "water solubility" as used in this application refers to solubility in aqueous media, e.g. phosphate buffered saline (PBS) at pH 7.4, or in 5% glucose solution. Tests for water solubility are given below in the Examples as "water solubility assay".

The pharmaceutically acceptable salts of compounds of the invention such as the compound of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Hydrochloric acid salts are of particular interest. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both a compound of formula (I) and its pharmaceutically acceptable salts.

As used herein, the term "alkyl" represents a straight chain or branched alkyl group, containing typically 1-10 carbon atoms, for example a $C_{1-6}$ alkyl group. Examples of alkyl groups include $C_{1-4}$ alkyl groups such as methyl, ethyl, n-propyl, i-propyl, and n-butyl.

The term "treatment" includes prophylactic as well as therapeutic treatment.

The term "formula II" refers to formula IIA and formula IIB collectively.

FIGURE LEGEND

FIG. 1: $^1$H NMR of compound 24
FIG. 2: X-ray powder diffraction pattern of compound 24 in solid crystalline form (Form I)

DESCRIPTION OF THE INVENTION

The present invention provides a macrocyclic sanglifehrin analogue, as set out above, methods for preparation of this compound and methods for the use of this compound in medicine.

In one embodiment, the compound is a methanol adduct thereof in which a hemi-ketal is formed by the combination of the C-53 keto and the C-15 hydroxyl groups and methanol. In another embodiment it is not.

In an embodiment of the invention, the double bond at the C26, 27 position is in the cis form, as represented by the following formula:

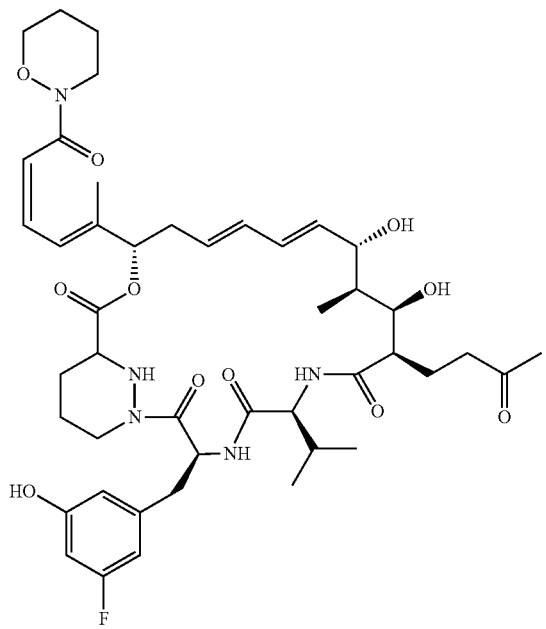 [SMILES: CC(=O)CC[C@H]1C(=O)N[C@@H](C(C)C)C(=O)N[C@@H](Cc2cc(O)cc(F)c2)C(=O)N2CCCC(N2)C(=O)O[C@H](/C(C)=C/C=C\C(=O)N2CCCCO2)C/C=C/C=C/[C@H](O)[C@H](C)[C@H]1O]

Such a compound may be produced during chemical synthesis.

In a further embodiment, there is provided a macrocyclic sanglifehrin analogue according to formula (I) in solid crystalline form. In particular, there is provided a solid crystalline form (Form I) of a macrocyclic sanglifehrin analogue according to formula (I) which is obtainable (or obtained) by crystallization of amorphous macrocyclic sanglifehrin analogue according to formula (I) from methyl isobutyl ketone (MIBK). In one embodiment, said amorphous form is slurried in MIBK and the temperature is cycled between a minimum and maximum temperature for a total period of time of, for example, 1 hour, 2 hours, 5 hours, 24 hours, 1 day, 2 days, 3 days, 4 days, 5 days, 6 days 7 days or 2 weeks. In one embodiment, the temperature is cycled between ambient temperature and 60° C., for example between ambient temperature and 40° C. In one embodiment, the temperature cycles between the minimum and maximum temperature (and visa versa) every 2-8 hours, for example, every 3-5 hours or every 4 hours. In a preferred embodiment, the temperature is cycled between ambient temperature and 40° C. every 4 hours for a total of 5 days.

A method of crystallization of the amorphous form of macrocyclic sanglifehrin analogue according to formula (I) is described in detail in Example 8.

Figure 2:
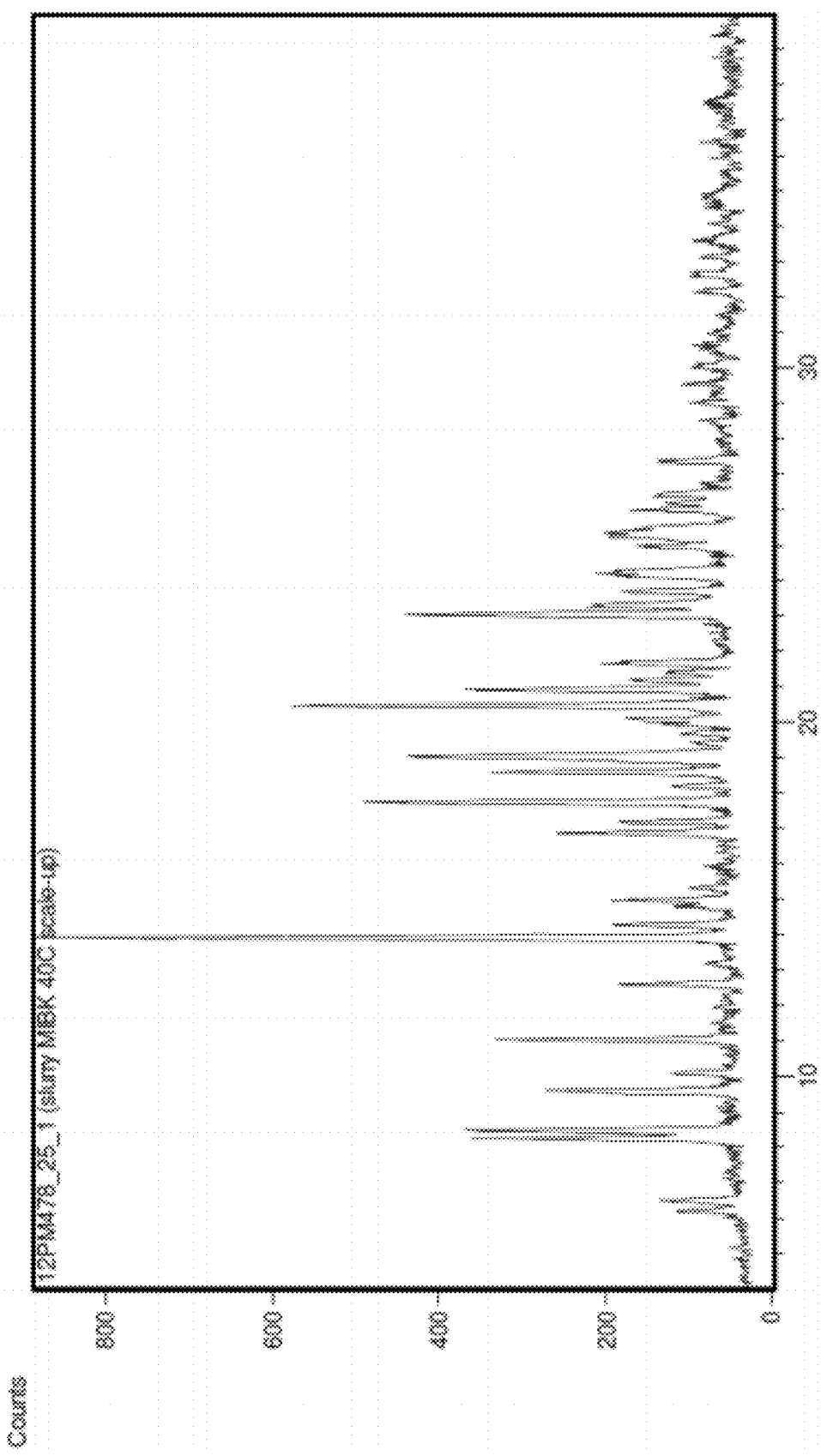

A macrocyclic sanglifehrin analogue according to formula (I) in the form of crystalline polymorph Form I has an X-ray powder diffraction (XRPD) pattern substantially as shown in FIG. 2. Table 2 (of Example 8) shows the peak listings and relative intensities. The method of obtaining the XRPD data is described in the General Methods.

Thus, there is provided a macrocyclic sanglifehrin analogue according to formula (I) in a crystalline form (Form I) having an XRPD pattern with at least at least one (for example, one, two, three, four, five, six, seven, eight, nine, ten, eleven, twelve, thirteen, fourteen, fifteen, sixteen or all seventeen) signals at 8.3, 8.5, 11.1, 12.6, 13.9, 14.3, 15.0, 16.9, 17.7, 18.6, 19.0, 20.1, 20.5, 20.9, 21.2, 21.7 and 23.0 (±0.2 degrees, 2-theta values), which signals constitute the major signals in the XRPD pattern of the Form I polymorph. The signals at 8.3, 8.5, 11.1, 13.9, 17.7, 18.6, 19.0, 20.5, 20.9 and 23.0 degrees 2-theta have comparatively high relative intensity (more than 26%—see FIG. 2) and therefore it is preferred to see at least one (for example, one, two, three, four, five, six, seven, eight, nine or all ten) of these. The signals at 13.9, 17.7, 19.0, 20.5 and 23.0 degrees 2-theta have particularly high relative intensity (more than 50%—see FIG. 2) and therefore it is preferred to see at least one (for example, one, two, three, four, or all five) of these.

The term "relative intensity" will be understood to mean the intensity given as a percentage as the intensity of the signal of highest intensity in the spectrum (which corresponds to the peak at 13.9 degrees 2-theta), as illustrated by FIG. 2.

In general, the compound of the invention is prepared by mutasynthesis to generate compounds of formula (II), followed by semisynthesis.

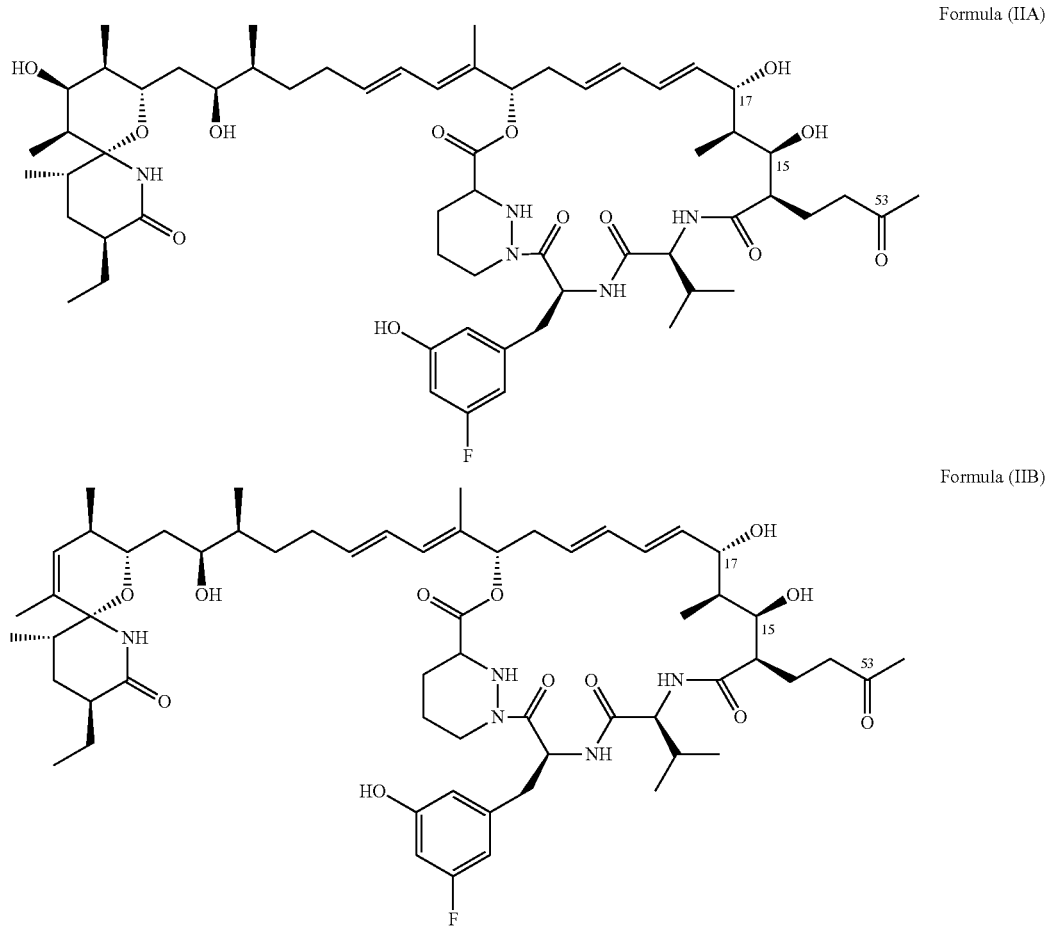

Formula (IIA)

Formula (IIB)

In general, a process for preparing precursors of a compound of formula (I) or a pharmaceutically acceptable salt thereof comprises:

Inoculating a fermentation broth with a culture of a sanglifehrin producer (such as *Streptomyces* sp. A92-308110, also known as DSM 9954) or more preferably, a sanglifehrin producer with the sfaA gene or sfaA gene homologue inactivated or deleted;

Feeding the fermentation broth with a meta-tyrosine analogue (as shown in formula (III), for example (S)-methyl 2-amino-3-(3-fluoro-5-hydroxyphenyl)propanoate, DL-5-fluoro-meta-tyrosine (9) or methyl 2-amino-3-(3-fluoro-5-hydroxyphenyl)propanoate (10))

Allowing fermentation to continue until compounds of formula IIA and formula IIB are produced Extracting and isolating compounds of formula IIA and formula IIB Semisynthetic derivatisation of compounds of formula IIA and formula IIB to generate the compound of formula I.

Compounds of formula (III) are defined as follows:

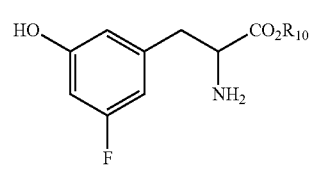

Formula (III)

where $R_{10}$ represents H or an ester forming group such as an alkyl group, e.g. $C_{1-6}$alkyl such as Me.

The feed may be racemic or the L-form of a compound of formula (III).

Compounds of formula (III) are either commercially available or prepared by standard organic synthetic chemistry techniques. One generic route to compounds of formula (III) is as shown in the following scheme 1a.

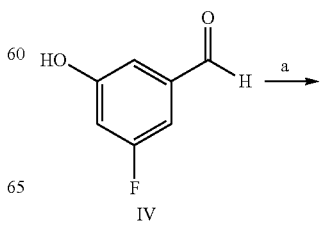

IV

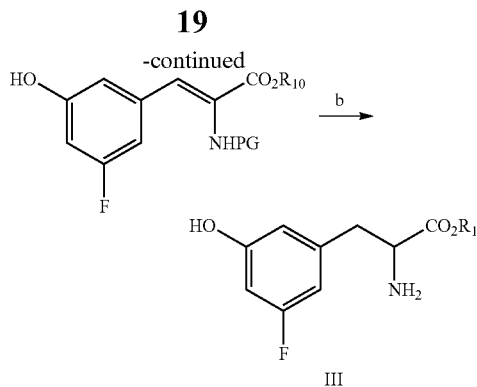

Scheme 1a: a) coupling aldehyde of formula (IV) with suitable fragment, e.g. $(R_{11}O)_2P(O)CH(NHPG)CO_2R_{10}$, and b) hydrogenation and deprotection as necessary. PG=protecting group.

Aldehydes of formula (IV) may be commercially available or readily synthesised by one skilled in the art. Protection and deprotection chemistry may need to be employed in generating compounds of formula (III) from compounds of formula (IV). These techniques are known to one skilled in the art and suitable protecting groups are described in Greene's Protective Groups in Organic Synthesis (Wuts and Greene, 4$^{th}$ Edition, 2007)

Following generation of compounds of formula (IIA) and formula (IIB), the compounds of the invention are prepared by semi-synthetic derivatisation. Semisynthetic methods for generating the sanglifehrin macrocyclic aldehyde are described in U.S. Pat. No. 6,124,453, Metternich et al., 1999, Banteli et al., 2001 and Sedrani et al., 2003.

In general, the semisynthetic process for preparing certain compounds of formula (I) or a pharmaceutically acceptable salt thereof from a sanglifehrin mutasynthetic analogue comprises:

(a) dihydroxylation of the sanglifehrin analogue;
(b) oxidative cleavage of the 1,2-diol to yield an aldehyde; and
(c) coupling said aldehyde with a stabilised carbanion (or canonical form thereof), such as a phosphonate carbanion, using a compound of formula V.

This is shown retrosynthetically below:

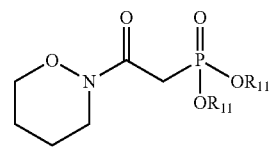

formula V

+

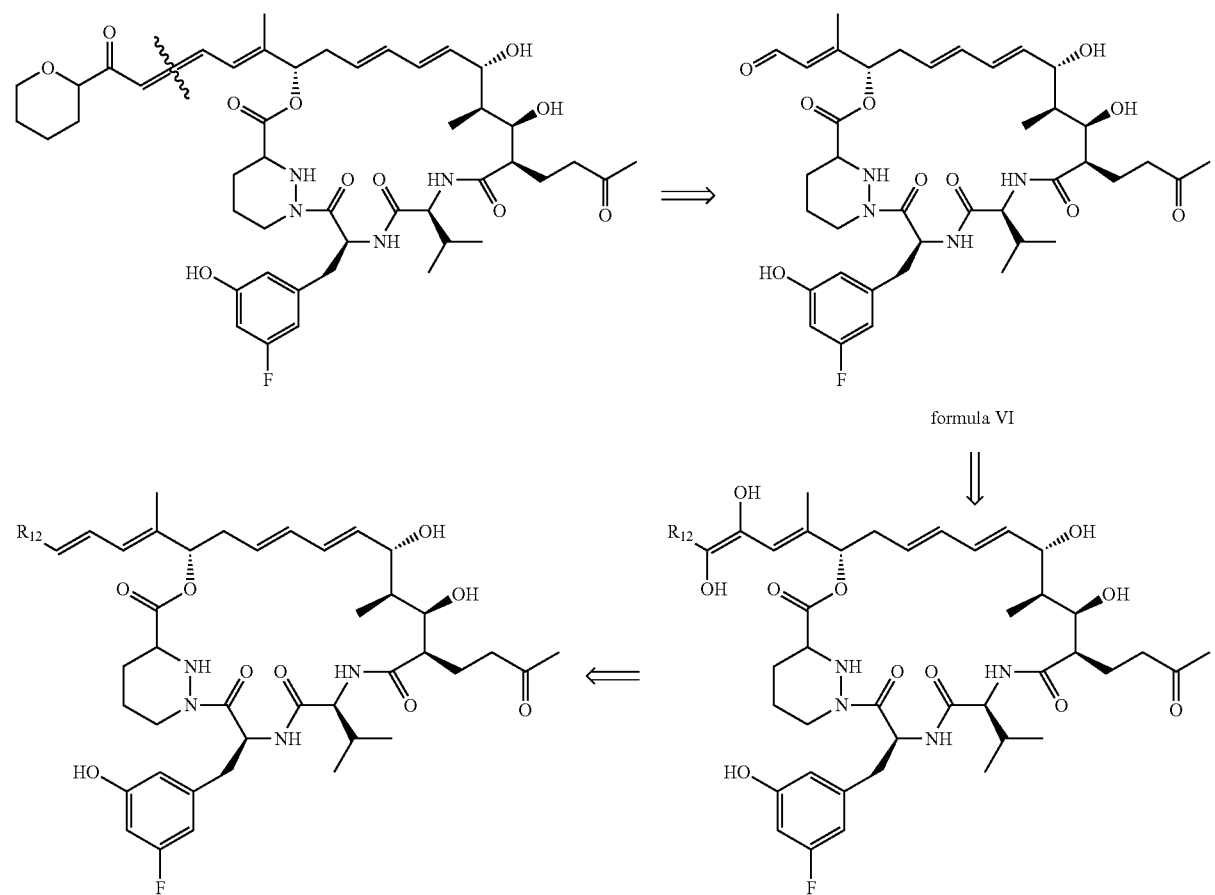

formula VI

Wherein for sanglifehrin A mutasynthetic analogues, $R_{12}$ = 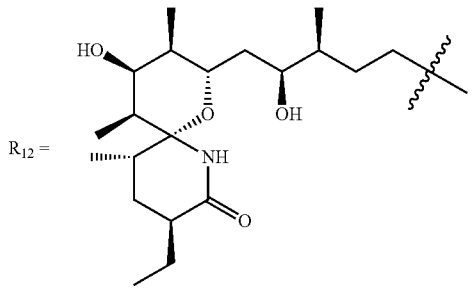 [SMILES: *CC[C@H](C)[C@@H](O)C[C@@H]1O[C@@]2(NC(=O)[C@@H](CC)C[C@@H]2C)[C@@H](C)[C@@H](O)[C@H]1C]

$R_{11}$ groups, which may be the same or different, independently represent alkyl (e.g. C1-4alkyl) or benzyl.

Hence, a process for preparing a compound of the invention comprises reacting a compound of formula (V) with an aldehydic macrocycle (compound of formula (VI)).

The preparation of compounds of formula (VI) may be performed by a process analogous to that described previously for the conversion of sanglifehrin A to its corresponding aldehydic macrocycle (Metternich et al. 1999). Briefly, the compound of formula (II) is dihydroxylated using modified Sharpless conditions (catalytic osmium tetroxide). The use of the chiral ligands aids in promoting selectivity. The resultant diol can then be cleaved oxidatively, using for instance sodium periodate. The resultant compound of formula VI can then be used as a substrate for derivatisation to a homologated amide, ester or ketone. Typically a compound of formula (V) is dissolved in an aprotic solvent, cooled and the treated with a base, for example sodium hydride. A compound of formula (VI) is then added and the reaction warmed in temperature. After a suitable period of time the reaction is stopped and the compound of formula I is purified by standard conditions (e.g. preparative HPLC, preparative TLC etc, normal phase flash chromatography).

Compounds of formula (V) may be known or may be prepared using known methods.

As shown in scheme 1 (below) the appropriate amine may be used to treat chloroacetyl chloride or similar to form an alpha-chloroamide. The alpha-chloroamide is then treated in an Arbuzov reaction to generate a compound of formula V. Other routes to compounds of formula V will be apparent to one skilled in the art.

Scheme 1

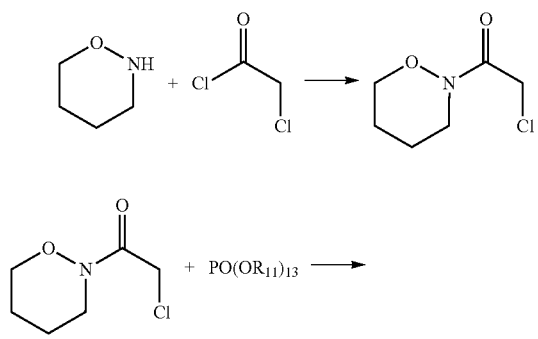

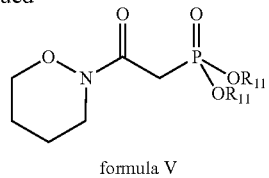

formula V

Further compounds of formula (V) may be known or readily synthesised from available carboxylic acid derivatives (e.g. $R_3COX$) wherein $R_3$ is the 1,2-oxazinane ring shown in scheme 2. As shown in scheme 2 (below) the carboxylic acid derivative may be coupled onto a methyl phosphonate after the phosphonate has been treated with base. This yields a compound of formula (V), though other routes to compounds of formula V will be apparent to one skilled in the art.

Scheme 2

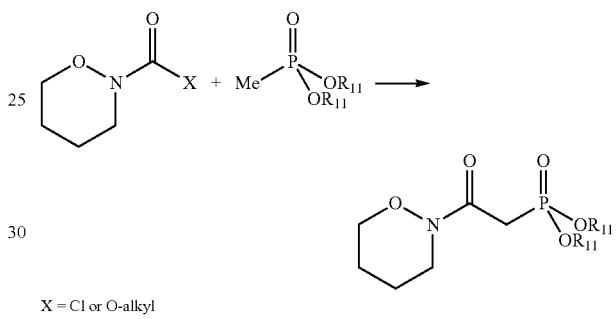

X = Cl or O-alkyl

If desired or necessary, protecting groups may be employed to protect functionality in the aldehydic macrocycle or macrocycle, or in compounds of formula V as described in T. W. Green, P. G. M. Wuts, *Protective Groups in Organic Synthesis*, Wiley-Interscience, New York, 1999.

In addition to the specific methods and references provided herein a person of skill in the art may also consult standard textbook references for synthetic methods, including, but not limited to Vogel's Textbook of Practical Organic Chemistry (Furniss et al., 1989) and March's Advanced Organic Chemistry (Smith and March, 2001).

A sanglifehrin analogue according to the invention may be administered alone or in combination with other therapeutic agents. Co-administration of two (or more) agents may allow for lower doses of each to be used, thereby reducing side effect, can lead to improved potency and therefore higher SVR, and a reduction in resistance.

Therefore in one embodiment, the mutasynthetic sanglifehrin analogue is co-administered with one or more therapeutic agent/s for the treatment of HCV infection, taken from the standard of care treatments. This could be an interferon (e.g. pIFNα and/or ribavirin).

In an alternative embodiment, a sanglifehrin macrocycle of the invention is co-administered with one or more other antiviral agents, such as a STAT-C (specifically targeted agent for treatment of HCV) or DAA (direct acting antivirals), which could be one or more of the following: Non-nucleoside Polymerase inhibitors (e.g. ABT-333, ABT-072, BMS 791325, IDX375, VCH-222, BI 207127, ANA598, VCH-916, GS 9190, PF-00868554 (Filibuvir) or VX-759), Nucleoside or nucleotide polymerase inhibitors (e.g. 2'-C-methylcytidine, 2'-C-methyladenosine, R1479, PSI-6130, R7128, R1626, PSI 7977 or IDX 184), Protease inhibitors (e.g. ABT-450, ACH-1625, BI 201355, BILN-2061, BMS-650032, CTS1027, Danoprevir, GS 9256, GS 9451, MK 5172, IDX 320, VX-950(Telaprevir), SCH503034(Boceprevir), TMC435350, MK-7009 (Vaneprivir), R7227/ITMN-191, EA-058, EA-063 or VX 985), NS5A inhibitors (e.g. A-831, BMS 790052, BMS 824393, CY-102 or PPI-461), silymarin, NS4b inhibitors, serine C-palmitoyltransferase inhibitors, Nitazoxanide or viral entry inhibitors (e.g. PRO 206).

In an alternative embodiment, a sanglifehrin macrocycle of the invention is co-administered with one or more other antiviral agents (such as highly active antiretroviral therapy (HAART)) for the treatment of HIV, which could be one or more of the following: nucleoside reverse transcriptase inhibitors (NRTI) (e.g. Emtricitabine or Tenofovir), non-nucleoside reverse transcriptase inhibitors (NNRTI) (e.g. Rilipivirine or Efavirenz), protease inhibitors (PI) (e.g. Ritonavir or Lopinavir), fusion inhibitors (e.g. Maraviroc or Enfuvirtide), CCR5 inhibitors (e.g. Aplaviroc or Vicriviroc), maturation inhibitors (e.g. Bevirimat), CD4 monoclonal antibodies (e.g. Ibalizumab) and integrase inhibitors (e.g. Eltiegravir).

In an alternative embodiment, a sanglifehrin macrocycle of the invention is co-administered with one or more other antiviral agents for the treatment of HBV, which could be one or more of the following: interferons (e.g. interferon alpha or pegylated interferon alpha), nucleoside or nucleotide analogues (e.g. lamivudine, entecavir, adefovir dipivoxil or telbivudine), other immunomodulators (e.g. Thymosin alpha, CYT107 or DV-601) or HMG CoA reductase inhibitors (e.g. Simvastatin).

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds of the invention will normally be administered orally in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above the formulations of this invention may include other agents conventional in the art having regard to the type of formulation in question, for example those suitable for oral administration may include flavouring agents.

Advantageously, agents such as preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Further aspects of the invention include:

A compound according to the invention for use as a pharmaceutical;

A compound according to the invention for use as a pharmaceutical for the treatment of viral infections (especially RNA virus infections) such as HCV or HIV infection, for use as an anti-inflammatory or for prophylaxis of organ transplant rejection;

A pharmaceutical composition comprising a compound according to the invention together with a pharmaceutically acceptable diluent or carrier;

A pharmaceutical composition comprising a compound according to the invention together with a pharmaceutically acceptable diluent or carrier further comprising a second or subsequent active ingredient, especially an active ingredient indicated for the treatment of viral infections such as HCV or HIV infection, for use as an anti-inflammatory or for prophylaxis of organ transplant rejection;

A method of treatment of viral infections (especially RNA virus infections) such as HCV or HIV infection, for use as an anti-inflammatory or for prophylaxis of organ transplant rejection which comprises administering to a subject a therapeutically effective amount of a compound according to the invention;

Use of a compound according to the invention for the manufacture of a medicament for the treatment of viral infections such as HCV or HIV infection, for use as an anti-inflammatory or for prophylaxis of organ transplant rejection.

General Methods

Materials and Methods

Bacterial Strains and Growth Conditions

The sanglifehrin producer *Streptomyces* sp. A92-308110 (DSM no 9954, purchased from DSMZ, Braunschweig, Germany) also termed BIOT-4253 and BIOT-4370 or its derivatives, such as BIOT-4585 are maintained on medium oatmeal agar, MAM, ISP4 or ISP2 (see below) at 28° C.

BIOT-4585 (for construction methodology, see Example 1) was grown on oatmeal agar at 28° C. for 7-10 days. Spores from the surface of the agar plate were collected into 20% w/v sterile glycerol in distilled and stored in 0.5-ml aliquots at −80° C. Frozen spore stock was used for inoculating seed media SGS or SM25-3. The inoculated seed medium was incubated with shaking between 200 and 300 rpm at 5.0 or 2.5 cm throw at 27° C. for 24 hours. The fermentation medium SGP-2 or BT6 were inoculated with 2.5%-10% of the seed culture and incubated with shaking between 200 and 300 rpm with a 5 or 2.5 cm throw at 24° C. for 4-5 days. The culture was then harvested for extraction.

Meta-Tyrosine Analogue (S)-methyl 2-amino-3-(3-fluoro-5-hydroxyphenyl)propanoate was purchased from NetChem (USA). (3-bromo-5-fluoroanisole (9-1) was purchased from Accela ChemBio Co., Ltd., (Shanghai, China) and can also be purchased from Amfinecom Inc (USA) or Apollo Scientific Ltd. (UK)). DL-5-fluoro-meta-tyrosine (9) and methyl 2-amino-3-(3-fluoro-5-hydroxyphenyl)propanoate (10)) were synthesised as follows.

DL-5-fluoro-meta-tyrosine (9) and methyl 2-amino-3-(3-fluoro-5-hydroxyphenyl)propanoate (10)

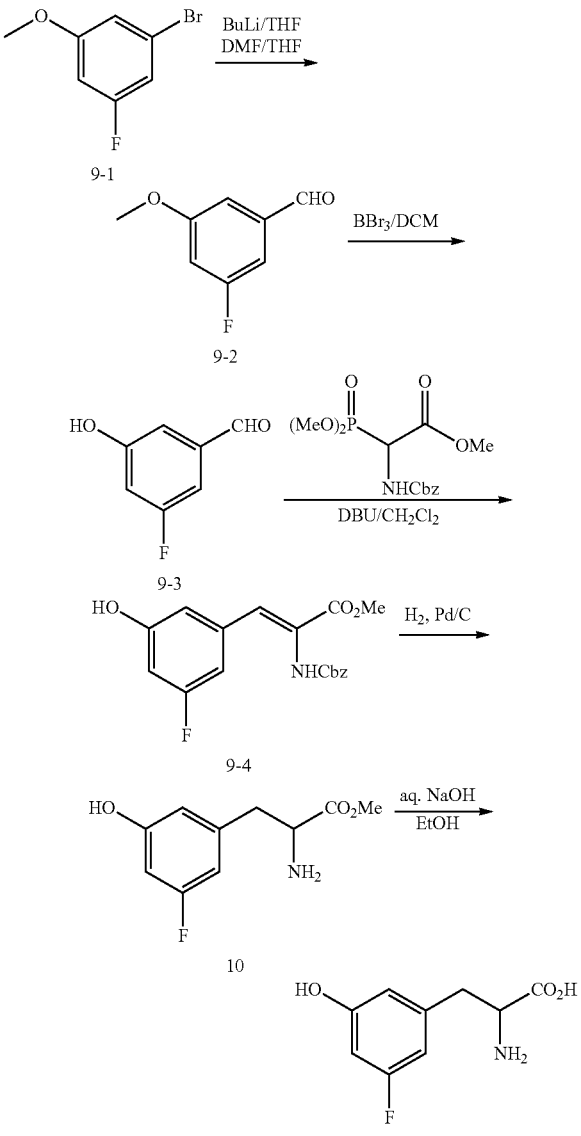

To a solution of 9-1 (20 g, 97.55 mmol) in tetrahydrofuran (100 mL) was added dropwise n-butyl lithium (43 mL, 2.5 M, 107.3 mmol) at −78° C. It was stirred for 30 minutes and N,N-dimethylformamide (15.1 mL, 195.1 mmol) was added at this temperature. It was stirred for another 30 minutes and the cold bath was removed. After 1 hour, the reaction was quenched with saturated aqueous ammonium chloride. The organic layer was washed with water and saturated aqueous sodium chloride, dried (sodium sulfate), filtered and concentrated. The residue was purified by chromatography on silica to give 9-2.

To a solution of 9-2 (6 g, 38.9 mmol) in dry DCM (200 mL) was added dropwise BBr₃ (4 M in DCM, 30 ml, 116.8 mmol)

at −70° C. After the addition, the reaction mixture was stirred at −20° C. for 3 hours, ice-water was added carefully, and extracted with DCM. The organic layers were washed with water and brine, dried over Na$_2$SO$_4$, filtered and concentrated. The residue was purified by flash chromatographed on silica to give the desired compound 9-3.

To a solution of methyl 2-(benzyloxycarbonylamino)-2-(dimethoxyphosphoryl)acetate (4.64 g, 14 mmol) in DCM (150 mL) was added DBU (4.26 g, 28 mmol) at room temperature. After 10 min, 9-3 (1.95 g, 14 mmol) was added and the resulting mixture was stirred at room temperature overnight. The solution was diluted with EtOAc (150 mL), separated and the organic layer was washed with 1 N HCl, dried over Na$_2$SO$_4$, filtered and concentrated. The residue was purified by flash chromatography on silica to give 9-4.

A solution of 9-4 (1 g) in MeOH (20 mL) was hydrogenated over 200 mg of 10% Pd/C at normal pressure overnight. After removal of the catalyst by filtration, the solvent was evaporated to give 10.

To a solution of 10 (300 mg, 1.4 mmol) in EtOH (30 mL) was added aq. NaOH (2 N, 4 mL), the reaction was stirred at room temperature for 30 minutes. The solvent was removed and the residue was neutralized to pH=6 with 2 N HCl and the white crystals that formed were collected by filtration to give the target compound 9.

Alternative route to methyl 2-amino-3-(3-fluoro-5-hydroxyphenyl)propanoate (10)

(3,5-Difluorobromobenzene (9a-1) was purchased from Darui Fine Chemicals Co., Ltd., (Shanghai, China) and can also be purchased from Alfa Aesar or Sigma Aldrich.)

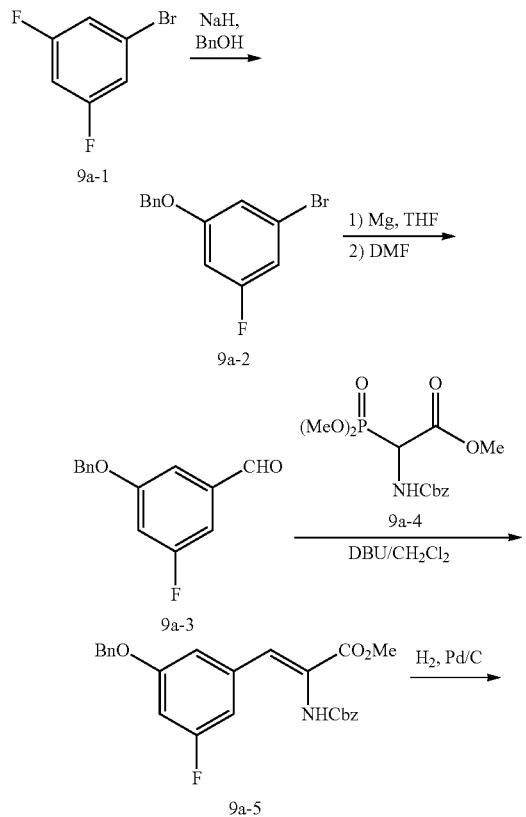

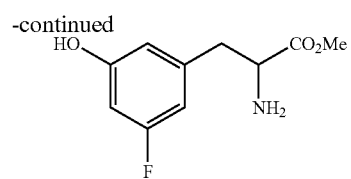

Preparation of 9a-2

To a solution of BnOH (1.61 mL, 15.54 mmol) in DMF (30 mL) was added NaH (622 mg, 60% dispersion in mineral oil, 15.54 mmol) at 0° C. Stirring was continued at room temperature for 0.5 h to give a clear solution. 9a-1 (1.79 mL, 15.54 mmol) was added at such a rate to maintain the temperature below 40° C. The mixture was stirred at room temperature overnight to give a yellow solution. The reaction was quenched by water and extracted with petroleum ether (35 mL×4). The combined organic layers were concentrated. And the residue was purified by silica gel chromatography eluting with petroleum ether to afford 9a-2 (2.544 g) as colorless oil.

Preparation of 9a-3

To a dry three flask were added Mg (170.1 mg, 7.10 mmol), anhydrous THF (10 mL), and a small quantity of iodine under nitrogen. ⅓ of 9a-2 (1.664 g, 5.9192 mmol) in THF (2 mL) was added. The mixture was heated to reflux. During this time, the yellow mixture gradually became bright yellow. Then the remaining ⅔ of 9a-2 was added dropwise, and the reaction mixture was refluxed for another 0.5 h.

To the above mixture was added DMF (0.504 mL, 6.51 mmol) slowly at 0° C. Stirring was continued for 0.5 h at room temperature. HCl (2 M, 10 mL) was added, and THF was evaporated. The residue was extracted with ethyl acetate (25 mL×3). And the combined organic layers were washed with brine and concentrated in vacuo. The residue was purified by silica gel chromatography eluting with petroleum ether to petroleum ether/ethyl acetate=20/1 to give 9a-3 (694 mg) as colorless oil.

Preparation of 9a-5

To a solution of methyl 2-(benzyloxycarbonylamino)-2-(dimethoxyphosphoryl)acetate, 9a-4 (993 mg, 3.00 mmol) in DCM (30 mL) was added DBU (832 uL, 5.57 mmol) at room temperature. After 10 min, 9a-3 (694 mg, 3.01 mmol) was added and the resulting mixture was stirred at room temperature for 1 hr. The solution was washed with HCl (1 M, 10 mL), and the combined organic layers were dried and concentrated in vacuo. The residue was purified by flash chromatography on silica (eluting with dichloromethane/ethyl acetate=10/1) to give 9a-5 (1.11 g).

Preparation of 10

A solution of 9a-5 (100 mg) in MeOH (50 mL) was hydrogenated over 20 mg of 10% Pd/C at normal pressure for 2 hrs. After removal of the catalyst by filtration, the solvent was evaporated to give 10 (33 mg).

Media Recipes

Water Used for Preparing Media was Prepared Using Millipore Elix Analytical Grade Water Purification System

| SGS Seed Medium | |
| --- | --- |
| Ingredient (and supplier) | Recipe |
| Glucose (Sigma, G7021) | 7.50 g |
| Glycerol (Fisher scientific, G/0650/25) | 7.50 g |
| yeast extract (Becton Dickinson, 212770) | 1.35 g |
| malt extract (Becton Dickinson, 218630) | 3.75 g |

SGS Seed Medium

| Ingredient (and supplier) | Recipe |
|---|---|
| potato starch (soluble) (Signma, S2004) | 7.50 g |
| NZ-amine A (Sigma, C0626) | 2.50 g |
| toasted soy flour, Nutrisoy (ADM, 063-160) | 2.50 g |
| L-asparagine (Sigma, A0884) | 1.00 g |
| $CaCO_3$ (Calcitec, V/40S) | 0.05 g |
| NaCl (Fisher scientific, S/3160/65) | 0.05 g |
| $KH_2PO_4$ (Sigma, P3786) | 0.25 g |
| $K_2HPO_4$ (Sigma, P5379) | 0.50 g |
| $MgSO_4 \cdot 7H_2O$ (Sigma, M7774) | 0.10 g |
| trace element solution B | 1.00 mL |
| agar | 1.00 g |
| SAG471 Antifoam (GE Silicones, SAG471) | *0.20 mL |
| RO $H_2O$ | to final vol. of **1.00 L | pre-sterilisation pH was adjusted to pH 7.0 with 10M NaOH/10M $H_2SO_4$ sterilised by heating 121° C., 20-30 min (autoclaving)
Notes
*antifoam only used in seed fermenters, NOT seed flasks
**final volume adjusted accordingly to account for seed volume

Trace Element Solution B

| Ingredient | Recipe |
|---|---|
| $FeSO_4 \cdot 7H_2O$ (Sigma, F8633) | 5.00 g |
| $ZnSO_4 \cdot 7H_2O$ (Sigma, Z0251) | 4.00 g |
| $MnCl_2 \cdot 4H_2O$ (Sigma, M8530) | 2.00 g |
| $CuSO_4 \cdot 5H_2O$ (Aldrich, 20,919-8) | 0.20 g |
| $(NH_4)_6Mo_7O_{24}$ (Fisher scientific, A/5720/48) | 0.20 g |
| $CoCl_2 \cdot 6H_2O$ (Sigma, C2644) | 0.10 g |
| $H_3BO_3$ (Sigma, B6768) | 0.10 g |
| KI (Alfa Aesar, A12704) | 0.05 g |
| $H_2SO_4$ (95%) (Fluka, 84720) | 1.00 mL |
| RO $H_2O$ | to final vol. of 1.00 L |

SGP2 Production Medium

| Ingredient | Recipe |
|---|---|
| toasted soy flour (Nutrisoy) (ADM, 063-160) | 20.00 g |
| Glycerol (Fisher scientific, G/0650/25) | 40.00 g |
| MES buffer (Acros, 172595000) | 19.52 g |
| SAG471 Antifoam (GE Silicones, SAG471) | *0.20 mL |
| RO $H_2O$ | to final vol. of **1.00 L | pre-sterilisation pH adjusted to pH 6.8 with 10M NaOH sterilised by heating 121° C., 20-30 min (autoclaving)
Notes
*final volume adjusted accordingly to account for seed volume
**antifoam was used only in fermentors not flasks

SM25-3 Medium (also termed SM25)

| Ingredient | |
|---|---|
| Glycerol (Fisher scientific, G/0650/25) | 40 g |
| Soy Peptone A3 SC (Organotechnie) | 10 g |
| Malt extract (Difco) | 21 g |
| to final vol. of | 1 L | pre-sterilisation pH not adjusted (i.e. pH 7.0)

ISP4 Medium

| Ingredient | |
|---|---|
| Soluble Starch (Difco) | 10 g |
| $K_2HPO_4$ | 1 g |
| $MgSO_4 \cdot 7H_2O$ | 1 g |
| NaCl | 1 g |
| $(NH_4)_2SO_4$ | 2 g |
| $CaCO_3$ | 2 g |
| ISP Trace Salts Solution | 1 mL |
| Agar | 20 g |
| to final vol. of | 1 L |

Make a paste with the starch in a small volume of cold water and bring to volume of 500 ml
Add other ingredients to solution II in 500 mls water pH should be between pH 7.0 and pH 7.4 (pH 7.3) Mix two solutions together and add agar

ISP Trace Salts

| | |
|---|---|
| $FeSO_4 \cdot 7H_2O$ | 1 g |
| $MnCl_2 \cdot 4H_2O$ | 1 g |
| $ZnSO_4 \cdot 7H_2O$ | 1 g |
| to final vol. of | 1 L |

Store at 4 degrees C

Oatmeal Agar (ISP3)

| Ingredient | Recipe |
|---|---|
| Oatmeal | 20.00 g |
| ISP trace element solution | 1.00 mL |
| Bacto Agar (Becton Dickinson) | 18.00 g |
| RO $H_2O$ | to final vol. of 1.00 L |

20 g oatmeal is cooked in 1 L water on a hotplate (or microwave) for 20 minutes. The cooked mixture is filtered through muslin/cheesecloth and brought to pH 7.2 and remade up to 1 L. 1 ml ISP trace elements solution is added. 18 g per L agar is then added before sterilizing.

MAM Agar

| Ingredient | Recipe |
|---|---|
| Wheat starch (Sigma) | 10.00 g |
| Corn steep powder (Roquette) | 2.50 g |
| Yeast extract (Becton Dickinson) | 3.00 g |
| $CaCO_3$ (Calcitec) | 3.00 g |
| $FeSO_4$ (Sigma) | 0.300 g |
| Bacto Agar (Becton Dickinson) | 20.00 g |
| RO $H_2O$ | to final vol. of 1.00 L | pH 5.8 prior to autoclaving

BT6 production media

| Ingredient | Recipe |
|---|---|
| Glucose (Sigma) | 50.00 g |
| Nutrisoy (ADM) | 30.00 g |
| NaCl (Fisher) | 5.00 g |
| $(NH_4)_2SO_4$ (Sigma) | 3.00 g |
| $CaCO_3$ (Calcitec) | 6.00 g |
| RO $H_2O$ | to final vol. of 1.00 L |

Adjust pH to 7.0 then add $CaCO_3$

| ISP2 agar | |
|---|---|
| Ingredient | Recipe |
| Yeast extract (Becton Dickinson) | 4.00 g |
| Malt Extract (Becton Dickinson) | 10.0 g |
| Dextrose (Sigma) | 4.00 g |
| Bacto Agar (Becton Dickinson) | 20.0 g |
| RO H$_2$O | to final vol. of 1.00 L |

Adjust pH to 7.3 prior to adding agar and sterilizing.

General Fermentation Method

Cryopreserved spore stocks of BIOT-4585 (for construction methodology, see Example 1) were thawed at room temperature. Vegetative cultures (seed cultures) were prepared by transferring 4.0 mL of spore stock into 400 mL medium SM25 in 2 L Erlenmeyer flasks with foam plug. Cultivation was carried out for 48 hours at 27° C. and 250 rpm (5.0 cm throw). From the seed culture 25 mL was transferred into 250 mL production medium SGP2+5% HP20 in 2 L Erlenmeyer flasks with foam plug. After 24 hours cultivation at 24° C. and 250 rpm (2.5 cm throw), 2 mL of a 250 mM racemic or 125 mM enantiomerically pure solution of the desired precursor (e.g. (S)-methyl 2-amino-3-(3-fluoro-5-hydroxyphenyl)propanoate, DL-5-fluoro-meta-tyrosine (9) or methyl 2-amino-3-(3-fluoro-5-hydroxyphenyl)propanoate (10)), in 1M hydrochloric acid and 2 mL of a 250 mM methanolic solution of DL-piperazic acid was added to each production flask to give a final 1 mM concentration of the individual enantiomers of the precursors. DMSO may optionally be used in place of 1M hydrochloric acid. The DL-piperazic acid may optionally be omitted. Cultivation was continued for further four days at 24° C. and 250 rpm (2.5 cm throw).

Analysis of Culture Broths by LC-UV and LC-UV-MS

Culture broth (1 mL) and ethyl acetate (1 mL) is added and mixed for 15-30 min followed by centrifugation for 10 min. 0.4 mL of the organic layer is collected, evaporated to dryness and then re-dissolved in 0.20 mL of acetonitrile.

HPLC Conditions:

C18 Hyperclone BDS C18 Column 3u, 4.6 mm×150 mm

Fitted with a Phenomenex Analytical C18 Security Guard Cartridge (KJ0-4282)

Column temp at 50° C.

Flow rate 1 mL/min

Monitor UV at 240 nm

Inject 20 uL aliquot

Solvent gradient:

0 min: 55% B 1.0 min: 55% B 6.5 min: 100% B 10.0 min: 100% B 10.05 min: 55% B 13.0 min: 55% B Solvent A is Water+0.1% Formic Acid Solvent B is Acetonitrile+0.1% Formic Acid Under these conditions SfA elutes at 5.5 min Under these conditions SfB elutes at 6.5 min LCMS is performed on an integrated Agilent HP1100 HPLC system in combination with a Bruker Daltonics Esquire 3000+ electrospray mass spectrometer operating in positive ion mode using the chromatography and solvents described above.

QC LC-MS Method

HPLC Conditions:

C18 Hyperclone BDS C18 Column 3u, 4.6 mm×150 mm

Fitted with a Phenomenex Analytical C18 Security Guard Cartridge (KJ0-4282)

Column temp at 50° C.

Flow rate 1 mL/min

Monitor UV at 210, 240 and 254 nm

Solvent gradient:

0 min: 10% B 2.0 min: 10% B 15 min: 100% B 17 min: 100% B 17.05 min: 10% B 20 min: 10% B Solvent A is Water+0.1% Formic Acid Solvent B is Acetonitrile+0.1% Formic Acid MS conditions:

MS operates in switching mode (switching between positive and negative), scanning from 150 to 1500 amu.

Xray Powder Diffraction (XRPD) Method

Approximately 2 mg of sample was gently compressed on the XRPD zero back ground single obliquely cut silica sample holder. The sample was then loaded into a Philips X-Pert MPD diffractometer and analysed using the following experimental conditions:

Tube anode: Cu

Generator tension: 40 kV

Tube current: 40 mA

Wavelength alpha1: 1.5406 Å

Wavelength alpha2: 1.5444 Å

Start angle [2 theta]: 5

End angle [2 theta]: 50

Continuous scan

In Vitro Replicon Assay for Assessment of HCV Antiviral Activity

Antiviral efficacy against genotype 1 HCV may be tested as follows: One day before addition of the test article, Huh5.2 cells, containing the HCV genotype 1b 1389luc-ubi-neo/NS3-3'/5.1 replicon (Vrolijk et al., 2003) and subcultured in cell growth medium [DMEM (Cat No. 41965039) supplemented with 10% FCS, 1% non-essential amino acids (11140035), 1% penicillin/streptomycin (15140148) and 2% Geneticin (10131027); Invitrogen] at a ratio of 1.3-1.4 and grown for 3-4 days in 75 cm$^2$ tissue culture flasks (Techno Plastic Products), were harvested and seeded in assay medium (DMEM, 10% FCS, 1% non-essential amino acids, 1% penicillin/streptomycin) at a density of 6 500 cells/well (100 µL/well) in 96-well tissue culture microtitre plates (Falcon, Beckton Dickinson for evaluation of the anti-metabolic effect and CulturPlate, Perkin Elmer for evaluation of antiviral effect). The microtitre plates are incubated overnight (37° C., 5% CO$_2$, 95-99% relative humidity), yielding a non-confluent cell monolayer.

Dilution series are prepared; each dilution series is performed in at least duplicate. Following assay setup, the microtitre plates are incubated for 72 hours (37° C., 5% CO$_2$, 95-99% relative humidity).

For the evaluation of anti-metabolic effects, the assay medium is aspirated, replaced with 75 µL of a 5% MTS (Promega) solution in phenol red-free medium and incubated for 1.5 hours (37° C., 5% CO$_2$, 95-99% relative humidity). Absorbance is measured at a wavelength of 498 nm (Safire$^2$, Tecan) and optical densities (OD values) are converted to percentage of untreated controls.

For the evaluation of antiviral effects, assay medium is aspirated and the cell monolayers are washed with PBS. The wash buffer is aspirated, 25 μL of Glo Lysis Buffer (Cat. No. E2661, Promega) is added after which lysis is allowed to proceed for 5 min at room temperature. Subsequently, 50 μL of Luciferase Assay System (Cat. No. E1501, Promega) is added and the luciferase luminescence signal is quantified immediately (1000 ms integration time/well, Safire², Tecan). Relative luminescence units are converted to percentage of untreated controls.

The EC50 and EC90 (values derived from the dose-response curve) represent the concentrations at which respectively 50% and 90% inhibition of viral replication would be observed. The CC50 (value derived from the dose-response curve) represents the concentration at which the metabolic activity of the cells would be reduced to 50% of the metabolic activity of untreated cells. The selectivity index (SI), indicative of the therapeutic window of the compound, is calculated as $CC_{50}/EC_{50}$.

A concentration of compound is considered to elicit a genuine antiviral effect in the HCV replicon system when, at that particular concentration, the anti-replicon effect is above the 70% threshold and no more than 30% reduction in metabolic activity is observed.

In Vitro Replicon Assay for Assessment of HCV Antiviral Activity in Genotypes 1a and 2a The replicon cells (subgenomic replicons of genotype 1a (H77) and 2a (JFH-1)) are grown in Dulbecco's modified essential media (DMEM), 10% fetal bovine serum (FBS), 1% penicillin-streptomycin (pen-strep), 1% glutamine, 1% non-essential amino acids, 250 μg/ml G418 in a 5% $CO_2$ incubator at 37° C. All cell culture reagents may be purchased from Mediatech (Herndon, Va.).

The replicon cells are trypsinized and seeded at $5\times10^3$ cells per well in 96-well plates with the above media without G418. On the following day, the culture medium is replaced with DMEM containing compounds serially diluted in the presence of 5% FBS. The HCV replicon antiviral assay examines the effects of compounds in a serial of compound dilutions. Briefly, the cells containing the HCV replicon are seeded into 96-well plates. Test article is serially diluted with DMEM plus 5% FBS. The diluted compound is applied to appropriate wells in the plate. After 72 hr incubation at 37° C., the cells are processed. The intracellular RNA from each well is extracted with an RNeasy 96 kit (Qiagen). The level of HCV RNA is determined by a reverse transcriptase-real time PCR assay using TaqMan® One-Step RT-PCR Master Mix Reagents (Applied Biosystems, Foster City, Calif.) and an ABI Prism 7900 sequence detection system (Applied Biosystems) a as described previously (Vrolijk et al., 2003). The cytotoxic effects are measured with TaqMan0 Ribosomal RNA Control Reagents (Applied Biosystems) as an indication of cell numbers. The amount of the HCV RNA and ribosomal RNA is then used to derive applicable $IC_{50}$ values (concentration inhibiting on replicon replication by 50%).

Assessment of Microsome Metabolism (Microsome Stability Assay)

Rate of metabolism in microsomes may be tested as follows:

Mouse or human liver microsomes were diluted with buffer C (0.1 M Potassium Phosphate buffer, 1.0 mM EDTA, pH 7.4) to a concentration of 2.5 mg/mL. Microsomal stability samples were then prepared by adding 50 μL of 5 μM compound spiking solution (0.5 μL 10 mM DMSO stock solution in 9.5 μL ACN, added to 990 μL Buffer C) to 50 μL of microsomal solution (2.5 mg/mL), 110 μL Buffer C and mixed well. All samples were pre-incubated for approximately 15 minutes at 37° C. Following this, the reaction was initiated by adding 40 μL of the NADPH solution (12.5 mM) with gentle mixing. Aliquots (40 μL) were removed at 0, 215, 30, 45 and 60 minutes and quenched with ACN containing internal standard (120 μL). Protein was removed by centrifugation (4000 rpm, 15 min) and the sample plate analysed for compound concentration by LC-MS/MS. Half-lives were then calculated by standard methods, comparing the concentration of analyte with the amount originally present.

Assessment of Hepatocyte Stability

Cryopreserved hepatocytes, previously stored in liquid nitrogen are placed in a 37±1° C. shaking water bath for 2 min±15 sec. The hepatocytes are then added to 10× volume of pre-warmed Krebs-Henseleit bicarbonate (KHB) buffer (2000 mg/L glucose, no calcium carbonate and sodium bicarbonate, Sigma), mixed gently and centrifuged at 500 rpm for 3 minutes. After centrifugation, the supernatant is carefully removed and a 10× volume of pre-warmed KHB buffer added to resuspend the cell pellet. This is mixed gently and centrifuged at 500 rpm for 3 minutes. The supernatant is then removed and discarded. The cell viability and yield are then determined by cell counts, and these values used to generate human hepatocyte suspensions to the appropriate seeding density (viable cell density=$2\times10^6$ cells/mL). A 2× dosing solution is prepared in pre-warmed KHB (1% DMSO) (200 μM spiking solution: 20 μL of substrate stock solution (10 mM) in 980 μL of DMSO, 2× dosing solution: 10 μL of 200 μM spiking solution in 990 μL of KHB (2 μM after dilution).

50 μL of pre-warmed 2× dosing solution is added to the wells and 50 μL of pre-warmed hepatocyte solution (2×106 cells/mL) added and timing started. The plate is then incubated at 37° C. 100 μL of acetonitrile containing internal standard is added to each the wells after completion of incubation time (0, 15, 30, 60 and 120 minutes) mixed gently, and 50 μL of pre-warmed hepatocyte solution added (2×106 cells/mL). At the end of the incubation, cell viability is determined. Samples are centrifuged at 4000 rpm for 15 minutes at 4° C., supernatants diluted 2-fold with ultrapure water and compound levels analysed by LC-MS/MS.

Assessment of Water Solubility

Water solubility may be tested as follows: A 10 mM stock solution of the sanglifehrin analogue is prepared in 100% DMSO at room temperature. Triplicate 0.01 mL aliquots are made up to 0.5 mL with either 0.1 M PBS, pH 7.3 solution or 100% DMSO in amber vials. The resulting 0.2 mM solutions are shaken, at room temperature on an IKA® vibrax VXR shaker for 6 h, followed by transfer of the resulting solutions or suspensions into 2 mL Eppendorf tubes and centrifugation for 30 min at 13200 rpm. Aliquots of the supernatant fluid are then analysed by the LCMS method as described above.

Alternatively, solubility in PBS at pH7.4 may be tested as follows: A calibration curve is generated by diluting the test compounds and control compounds to 40 μM, 16 μM, 4 μM, 1.6 μM, 0.4 μM, 0.16 μM, 0.04 μM and 0.002 μM, with 50% MeOH in $H_2O$. The standard points are then further diluted 1:20 in MeOH:PBS 1:1. The final concentrations after 1:20 dilution are 2000 nM, 800 nM, 200 nM, 80 nM, 20 nM, 8 nM, 2 nM and 1 nM. Standards are then mixed with the same volume (1:1) of ACN containing internal standard (hydroxymacrocycle, 6). The samples are centrifuged (5 min, 12000 rpm), then analysed by LC/MS.

| | Solution (μL) | MeOH/H₂O (1:1) (μL) | | Working solution (μM) | Solution (μL) | MeOH/buffer (1:1) (μL) | | Final solution (nM) |
|---|---|---|---|---|---|---|---|---|
| 10 mM | 10 | 240 | → | 400 | | | | |
| 400 μM | 50 | 450 | → | 40 | 20 | 380 | → | 2000 |
| | 20 | 480 | → | 16 | 20 | 380 | → | 800 |
| 40 μM | 50 | 450 | → | 4 | 20 | 380 | → | 200 |
| 16 μM | 50 | 450 | → | 1.6 | 20 | 380 | → | 80 |
| 4 μM | 50 | 450 | → | 0.4 | 20 | 380 | → | 20 |
| 1.6 μM | 50 | 450 | → | 0.16 | 20 | 380 | → | 8 |
| 0.4 μM | 50 | 450 | → | 0.04 | 20 | 380 | → | 2 |
| 0.04 μM | 50 | 950 | → | 0.002 | 20 | 380 | → | 1 |

Test compounds are prepared as stock solutions in DMSO at 10 mM concentration. The stock solutions are diluted in duplicate into PBS, pH7.4 in 1.5 mL Eppendorf tubes to a target concentration of 100 μM with a final DMSO concentration of 1% (e.g. 4 μL of 10 mM DMSO stock solution into 396 μL 100 mM phosphate buffer). Sample tubes are then gently shaken for 4 hours at room temperature. Samples are centrifuged (10 min, 15000 rpm) to precipitate undissolved particles. Supernatants are transferred into new tubes and diluted (the dilution factor for the individual test article is confirmed by the signal level of the compound on the applied analytical instrument) with PBS. Diluted samples are then mixed with the same volume (1:1) of MeOH. Samples are finally mixed with the same volume (1:1) of ACN containing internal standard (hydroxymacrocycle, 6) for LC-MS/MS analysis.

Assessment of Cell Permeability

Cell permeability may be tested as follows: The test compound is dissolved to 10 mM in DMSO and then diluted further in buffer to produce a final 10 μM dosing concentration. The fluorescence marker lucifer yellow is also included to monitor membrane integrity. Test compound is then applied to the apical surface of Caco-2 cell monolayers and compound permeation into the basolateral compartment is measured. This is performed in the reverse direction (basolateral to apical) to investigate active transport. LC-MS/MS is used to quantify levels of both the test and standard control compounds (such as Propanolol and Acebutolol).

In Vivo Assessment of Pharmacokinetics

In vivo assays may also be used to measure the bioavailability of a compound. Generally, a compound is administered to a test animal (e.g. mouse or rat) both intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

Mice are dosed with 1, 10, or 100 mg/kg of the compound of the invention or the parent compound i.v. or p.o. Blood samples are taken at 5, 10, 15, 30, 45, 60, 90, 120, 180, 240, 360, 420 and 2880 minutes and the concentration of the compound of the invention or parent compound in the sample is determined via HPLC. The time-course of plasma concentrations can then be used to derive key parameters such as the area under the plasma concentration-time curve (AUC—which is directly proportional to the total amount of unchanged drug that reaches the systemic circulation), the maximum (peak) plasma drug concentration, the time at which maximum plasma drug concentration occurs (peak time), additional factors which are used in the accurate determination of bioavailability include: the compound's terminal half life, total body clearance, steady-state volume of distribution and F %. These parameters are then analysed by non-compartmental or compartmental methods to give a calculated percentage bioavailability, for an example of this type of method see Egorin et al. 2002, and references therein.

In Vivo Assessment of Oral and Intravenous Pharmacokinetics (Specific Method)

For sanglifehrin analogues, whole blood is analysed. Compounds are formulated in 5% ethanol/5% cremophor EL/90% saline for both p.o. and i.v. administration. Groups of 3 male CD1 mice are dosed with either 1 mg/kg i.v. or 5 or 10 mg/kg p.o. Blood samples (40 μL) are taken via saphenous vein, pre-dose and at 0.25, 0.5, 2, 8, and 24 hours, and diluted with an equal amount of $dH_2O$ and put on dry ice immediately. Samples are stored at −70° C. until analysis. The concentration of the compound of the invention or parent compound in the sample is determined via LCMS as follows: 20 μL of blood:$H_2O$ (1:1, v/v)/PK sample is added with 20 μL Internal standard (hydroxyl macrocycle, 6) at 100 ng/mL, 20 μL working solution/MeOH and 150 μL of ACN, vortexed for 1 minute at 1500 rpm, and centrifuged at 12000 rpm for 5 min. The supernatant is then injected into LC-MS/MS. The time-course of blood concentrations is plotted and used to derive area under the whole blood concentration-time curve (AUC—which is directly proportional to the total amount of unchanged drug that reaches the systemic circulation). These values are used to generate PK parameters where possible.

In Vitro Assessment of Cytotoxicity

Huh-7 and HepG2 cells obtained from ATCC are grown in Dulbecco's modified essential media (DMEM) containing 10% fetal bovine serum (FBS), 1% penicillin-streptomycin (pen-strep) and 1% glutamine; whereas CEM cells (human T-cell leukemia cells obtained from ATCC) are grown in RPMI 1640 medium with 10% FBS, 1% pen-strep and 1% glutamine. Fresh human PBMCs are isolated from whole blood obtained from at least two normal screened donors. Briefly, peripheral blood cells are pelleted/washed 2-3 times by low speed centrifugation and resuspension in PBS to remove contaminating platelets. The washed blood cells are then diluted 1:1 with Dulbecco's phosphate buffered saline (D-PBS) and layered over 14 mL of Lymphocyte Separation Medium (LSM; cellgrow by Mediatech, Inc.; density 1.078+/−0.002 g/ml; Cat.#85-072-CL) in a 50 mL centrifuge tube and centrifuged for 30 minutes at 600×g. Banded PBMCs are gently aspirated from the resulting interface and subsequently washed 2× with PBS by low speed centrifugation. After the final wash, cells are counted by trypan blue exclusion and resuspended at $1 \times 10^7$ cells/mL in RPMI 1640 supplemented with 15% Fetal Bovine Serum (FBS), 2 mM L-glutamine, 4 μg/mL PHA-P. The cells are allowed to incubate for 48-72 hours at 37° C. After incubation, PBMCs are centrifuged and resuspended in RPMI 1640 with 15% FBS, 2 mM L-glutamine, 100 U/mL penicillin, 100 µg/mL streptomycin, 10 µg/mL gentamycin, and 20 U/mL recombinant human IL-2.

Compound cytotoxicity is evaluated by testing half-log concentrations of each compound in triplicate against the cells described above. Cell containing medium alone served as the cell control (CC). Huh-7 and HepG2 cells are seeded in 96-well plates at a concentration of $5 \times 10^3$ cells per well. On the following day, the media is aspirated, and 100 µL of corresponding media containing 5% FBS is added. Test drug dilutions are prepared at a 2× concentration in microtiter tubes and 100 µL of each concentration is placed in appropriate wells in a standard format. After 72 hours, the cells are processed for cytotoxicity assessment. PBMCs are diluted in fresh medium and plated in the interior wells of a 96 well round bottom microplate at $5 \times 10^4$ cells/well in a volume of 100 L. Similarly, CEM cells are plated at $1 \times 10^4$ cells/well. Then, 100 µL of 2× preparations of the test drugs are added in appropriate wells in a standard format. The cultures are maintained for six to seven days and then processed for cytotoxicity determination.

Cytotoxicity is determined using CytoTox-ONE™ homogeneous membrane integrity assay kit (Promega). The assay measures the release of lactate dehyrodgenase (LDH) from cells with damaged membranes in a fluorometric, homogeneous format. LDH released into the culture medium is measured with a coupled enzymatic assay that results in the conversion of resazurin into a fluorescent resorufin product. The amount of fluorescence produced is proportional to the number of lysed cells. Six serially diluted concentrations of each compound are applied to the cells to derive where applicable TC50 (toxic concentration of the drug decreasing cell viability by 50%) and TC90 (toxic concentration of the drug decreasing cell viability by 90%) values.

In Vitro Assessment of Inhibition of MDR1 and MRP2 Transporters

To assess the inhibition and activation of the MDR1 (P-glycoprotein 1) and MRP2 transporters, an in vitro ATPase assay from Solvo Biotechnology Inc. can be used (Glavinas et al., 2003). The compounds (at 0.1, 1, 10 and 100 µM) are incubated with MDR1 or MRP2 membrane vesicles both in the absence and presence of vanadate to study the potential ATPase activation. In addition, similar incubations are conducted in the presence of verapamil/sulfasalazine in order to detect possible inhibition of the transporter ATPase activity. ATPase activity is measured by quantifying inorganic phosphate spectrophotometrically. Activation is calculated from the vanadate sensitive increase in ATPase activity. Inhibition is determined by decrease in verapamil/sulfasalazine mediated ATPase activity.

In Vitro Assessment of Inhibition of Pgp Transporters Using Mdck Cells

To assess the inhibition of the P-glycoprotein (Pgp/MDR1) transporter, an in vitro ATPase assay from Cyprotex was used. MDR1—MDCK cells obtained from the NIH (Rockville, Md., USA) were used. Following culture, the monolayers were prepared by rinsing both basolateral and apical surfaces twice with buffer at pH 7.4 and 37° C. Cells were then incubated with pH 7.4 buffer in both apical and basolateral compartments for 40 min at 37° C. and 5% $CO_2$ with a relative humidity of 95% to stabilise physiological parameters. For the apical to basolateral study (A-B), buffer at pH 7.4 was removed from the apical compartment and replaced with loperamide dosing solutions before being placed in the 'companion' plates. The solutions were prepared by diluting loperamide in DMSO with buffer to give a final loperamide concentration of 5 µM (final DMSO concentration adjusted to 1%). The fluorescent integrity marker Lucifer yellow was also included in the dosing solution. The experiment was performed in the presence and absence of the test compound (applied to both the apical and basolateral compartments). For basolateral to apical (B-A) study, the P-glycoprotein substrate, loperamide (final concentration=5 µM) was placed in the basolateral compartment. The experiment was performed in the presence and absence of the test compound (applied to the apical and basolateral compartments). Incubations were carried out in an atmosphere of 5% $CO_2$ with a relative humidity of 95% at 37° C. for 60 min. After the incubation period, the companion plate was removed and apical and basolateral samples diluted for analysis by LC-MS/MS. A single determination of each test compound concentration was performed. On each plate, a positive control inhibitor was also screened. The test compound was assessed at 0.1, 0.3, 1, 3, 10, 30 and 50 µM. The integrity of the monolayers throughout the experiment was checked by monitoring Lucifer yellow permeation using fluorimetric analysis. After analysis, an $IC_{50}$ was calculated (i.e., inhibitor concentration (test drug) achieving half maximal inhibition effect).

In Vitro Assessment of Inhibition of Uptake Transporters

To assess the inhibition of the OAT1B1 and OAT1B3 uptake transporters, an in vitro uptake transporter assay from Solvo Biotechnology Inc. was used. Uptake experiments with Test Article (TA) at 0.068, 0.2, 0.62, 1.8, 5.5, 16.7 and 50 µM, were performed on CHO cells stably expressing human SLC transporters OATP1B1 and OATP1B3. Parental cell line CHO-K was used as negative control. Cells ($1 \times 10^5$ in 200 µl 1:1 mixture of Dulbecco's Modified Eagle's Medium and Ham's F-12 DMEM (F-12, Lonza, N.J., US) supplemented with 5 mM sodium butyrate) were plated on standard 96-well tissue culture plates and incubated 24 hours before the experiment at 37° C. in an atmosphere of 5% CO2 and 95% air. Before experiments the medium was aspirated by vacuum suction, cells were washed with 2×100 µl of Krebs-Henseleit buffer pH 7.3 (prepared from Sigma chemicals, Sigma-Aldrich, St Louis, Mo.). Uptake experiments were carried out at 37° C. in 50 µl of Krebs-Henseleit buffer (pH 7.3) containing the probe substrate and the TA or solvent, respectively. The organic solvent concentration was equal in each well, and did not exceed 1% v/v. The probe substrate for the OATP1B1 assay was E3S (0.1 µM) and for the OATP1B3 assay was Fluo-3 (10 µM). The translocated amount of probe substrate was determined for each well in cpm. Relative activities were calculated from the equation:

$$\text{Activity\%} = (A-B)/(C-D) \times 100$$

Where A=translocated amount of substrate in the presence of TA on transfected cells, B=translocated amount of substrate in the presence of TA on parental cells, C=translocated amount of substrate in the presence of solvent on transfected cells and D=translocated amount of substrate in the presence of solvent on parental cells. $IC_{50}$ was defined as the TA concentration needed to inhibit transport of the probe substrate by 50%. $IC_{50}$ was derived from the three-parameter logistic equation; a curve fitted onto the relative activity vs. TA concentration plot by non-linear regression.

In Vitro Assessment of Inhibition of Efflux Transporters

To assess the inhibition of the MRP2, MRP3 and BSEP efflux transporters, an in vitro vesicular transporter assay from Solvo Biotechnology Inc. was used. The Test Articles (TAs) (at 0.068, 0.2, 0.62, 1.8, 5.5, 16.7 and 50 µM) were incubated with efflux transporter membrane vesicles (Solvo Biotechnology Inc.) both in the absence and presence of 4 mM ATP to distinguish between transporter mediated uptake and passive diffusion of TA's into the vesicles. In the case of MRP2 and MRP3 transporters reactions were carried out in the presence of 2 mM glutathione. Reaction mixtures were preincubated for ten minutes at 37° C. Reactions were started by the addition of 25 μl of 12 mM MgATP (4 mM final concentration in assay) or assay buffer for background controls. Reactions were stopped by adding 200 μl of ice-cold washing buffer and immediately followed by filtration on glass fiber filters in a 96-well format (filter plate). Scintillation buffer was added to the washed and dried filter plate and scintillation was counted subsequently. Probe substrates were taurocholate (2 μM) for BSEP vesicles and $E_2 17\beta G$ (1 μM) for MRP2 and MRP3 vesicles. For all wells the translocated amount of the probe substrate was determined in cpm units. Relative activities were calculated with the following equation:

Activity %=(A−B)/(C−D)×100 Where A=translocated amount of substrate in the presence of TA and ATP, B=translocated amount of substrate in the presence of TA, C=translocated amount of substrate in the presence of solvent and ATP and D=translocated amount of substrate in the presence of solvent. $IC_{50}$ was defined as the TA concentration needed to inhibit transport of the probe substrate by 50%. $IC_{50}$ was derived from the three-parameter logistic equation; a curve fitted onto the relative activity vs. TA concentration plot by non-linear regression.

In Vitro Assay for Assessment of HIV Antiviral Activity

Antiviral efficacy against HIV may be tested as follows: Blood derived CD4+ T-lymphocytes and macrophages are isolated as described previously (Bobardt et al., 2008). Briefly, human PBMCs were purified from fresh blood by banding on Ficoll-Hypaque (30 min, 800 g, 25° C.). Primary human CD4+ T cells were purified from PBMCs by positive selection with anti-CD4 Dynabeads and subsequent release using Detachabead. Cells were cultured in RPMI medium 1640 (Invitrogen) supplemented with 10% FCS, MEM amino acids, L-glutamine, MEM vitamins, sodium pyruvate, and penicillin plus streptomycin and were subsequently activated with bacterial superantigen staphylococcal enterotoxin B (SEB; 100 ng/ml) and mitomycin C-killed PBMC from another donor (10:1 PBMC:CD4 cell ratio). Three days after stimulation, cells were split 1:2 in medium containing IL-2 (200 units/ml final concentration). Cultures were then split 1:2 every 2 days in IL-2 medium and infected with HIV at 7 days after stimulation. For generating primary human macrophages, monocytes were purified from human PBMCs by negative selection and activated and cultured at a cell concentration of 106/ml in DMEM, supplemented with 10% FCS, MEM amino acids, L-glutamine, MEM vitamins, sodium pyruvate, and penicillin (100 units/ml), streptomycin (100 mg/ml), and 50 ng/ml recombinant human granulocyte—macrophage colony-stimulating factor (GM-CSF) and maintained at 37° C. in a humidified atmosphere supplemented with 5% $CO_2$. To obtain monocyte-derived macrophages, cells were allowed to adhere to plastic and cultured for 6 days to allow differentiation.

CD4+ HeLa cells, Jurkat cells, activated CD4+ peripheral blood T-lymphocytes and macrophages (500,000 cells/100 μL) were incubated with pNL4.3-GFP (X4 virus) or pNL4.3-BaL-GFP (R5 virus) (100 ng of p24) in the presence of increasing concentrations of test article, Forty-eight hours later, infection was scored by analyzing the percentage of GFP-positive cells by FACS and $EC_{50}$ calculated.

In Vitro Assay for Assessment of HBV Antiviral Activity

Antiviral efficacy against HBV may be tested as follows: HepG2 2.2.15 cells are plated in 96-well microtiter plates. After 16-24 hours the confluent monolayer of HepG2 2.2.15 cells is washed and the medium is replaced with complete medium containing various concentrations of a test compound in triplicate (e.g. six half-log concentrations). Three days later the culture medium is replaced with fresh medium containing the appropriately diluted test compounds. Six days following the initial administration of the test compound, the cell culture supernatant is collected, treated with pronase and then used in a real-time quantitative TaqMan qPCR assay. The PCR-amplified HBV DNA is detected in real-time by monitoring increases in fluorescence signals that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($IC_{50}$). A dye uptake assay is then employed to measure cell viability, which is used to calculate toxicity ($TC_{50}$). The therapeutic index (TI) is calculated as $TC_{50}/IC_{50}$.

In Vitro Mixed Lymphocyte Reaction (MLR) Assay for Assessment of Immunosuppressant Activity Immunosuppressant activity was tested as follows: Peripheral blood mononuclear cell (PBMC) populations were purified from the blood of two normal, unrelated volunteer donors (A & B), using centrifugation over histopaque. Cells were counted and plated out at $1 \times 10^5$ cells per well in 96 well plates in RPMI media, with supplements and 2% Human AB serum.

Culture conditions included: cell populations A & B alone and a mixed population of cells A&B in the absence or presence of test compounds, each at 6 different concentrations. Compounds were tested at doses ranging from 10 μM to 0.0001 μM in 1-log increments. Control wells contained a comparable concentration of vehicle (0.5% DMSO) to that present in the test compound wells. Cultures were established in triplicate in a 96 well plate and incubated at 37° C. in 5% $CO_2$ in a humidified atmosphere. 3H-thymidine was added on day 6 after assay set up and harvested 24 hrs later. The levels of proliferation between the different culture conditions were then compared.

The ability of each dilution of test compound to inhibit proliferation in the MLR was calculated as percentage inhibition. This allowed estimation of the $IC_{50}$ (concentration of test compound which resulted in a 50% reduction of counts per minute). In order to calculate the $IC_{50}$, the X axis was transformed to a log scale. Non-linear regression was used to fit to the mean data points. A sigmoidal variable slope was selected.

ELISA Analysis of Cyp-NS5A Interaction.

This assay was used to measure the disruption of Cyp-NS5A complexes, which can be used to show the potency of interaction with Cyclophilin D. Briefly, production and purification of recombinant GST, GST-CypD and Con1 NS5A-His proteins was carried out as described previously (Chatterji et al., 2010). Nunc MaxiSorb 8-well strip plates were coated with GST or GST-CypD for 16 h at 4° C. and blocked. Recombinant NS5A-His (1 ng/mL) was added to wells in 50 μL of binding buffer (20 mM Tris pH 7.9, 0.5 M NaCl, 10% glycerol, 10 mM DTT and 1% NP-40) for 16 h at 4° C. Captured NS5A-His was subsequently detected using mouse anti-His antibodies (1 μg/mL) (anti-6×His, Clontech) and rabbit anti-mouse-horseradish peroxidase phosphatase (HRP) antibodies (1:1000 dilution). All experiments were conducted twice using two different batches of recombinant CypD and NS5A proteins.

Anti-PPIAse Analysis of Cyclophilin Inhibition

An alternative methodology for analysing interaction with cyclophilins is described as follows: The PPlase activity of recombinant CypA or D, produced by thrombin cleavage of GST-CypA or D, was determined by following the rate of hydrolysis of N-succinyl-Ala-Ala-Pro-Phe-p-nitroanilide by chymotrypsin. Chymotrypsin only hydrolyzes the trans form of the peptide, and hydrolysis of the cis form, the concentration of which is maximized by using a stock dissolved in trifluoroethanol containing 470 mM LiCl, is limited by the rate of cis-trans isomerization. CypA or D was equilibrated for 1 h at 5° C. with selected test article using a drug concentration range from 0.1 to 20 nM. The reaction was started by addition of the peptide, and the change in absorbance was monitored spectrophotometrically at 10 data points per second. The blank rates of hydrolysis (in the absence of CypA or D) were subtracted from the rates in the presence of CypA or D. The initial rates of the enzymatic reaction were analyzed by first-order regression analysis of the time course of the change in absorbance.

EXAMPLES

Example 1

Construction of an sfaA Deletion Mutant of *Streptomyces* sp. A92-308110 (DSM9954)

1.1 Construction of the sfaA Deletion Construct

The ~7 kb EcoRV-StuI fragment of cosmid TL3006 (SEQ ID NO. 3) encompassing sfaA (nucleotide position 14396-21362, NCBI sequence accession number FJ809786) was excised by digestion with EcoRV and StuI and the resulting isolated fragment ligated directly into pKC1139 that had previously been digested with EcoRV and treated with shrimp alkaline phosphatase (Roche). This plasmid was designated pSGK268.

An in frame deletion of the sfaA gene contained within this clone was performed using the Red/ET recombination kit supplied by Gene Bridges (catalog number K006).

SfaA17161f
(SEQ ID NO. 1)
5'-CGCTCTGTGGCGCCTGGTTTCCAAGCGGCTCGCGGACCGGCACCGGC

ACATGCATAATTAACCCTCACTAAAGGGCG-3'

SfaA17825r
(SEQ ID NO. 2)
5'-TGGATGTATCGTCGCAGGACGCCCAGAATTCACCTGCGACGTCCTCC

AGATGCATTAATACGACTCACTATAGGGCTC-3'

Two oligonucleotides, SfaA17161f and SfaA17825r were used to amplify the neomycin marker from the FRT-PGK-gb2-neo-FRT template DNA supplied in the kit using KOD DNA polymerase. The resulting ~1.7 kb amplified product was isolated by gel electrophoresis and purified from the gel with QiaEX resin.

Plasmid pSGK268 was transformed into *E. coli* DH10B using standard techniques and selected on plates containing apramycin (50 μg/ml). Introduction of the deletion construct was performed essentially following the Gene Bridges kit protocol. A single colony was grown overnight in 2TY apramycin (50 μg/ml) and transformed with the pRedET (tet) plasmid and selected on apramycin (50 μg/ml) and tetracycline (3 μg/ml) at 30° C. A single colony was used to prepare an overnight culture of this strain in 3 ml 2TY apramycin (50 μg/ml) and tetracycline (3 μg/ml) at 30° C. 0.5 ml of this culture was used to inoculate 10 ml 2TY apramycin (50 μg/ml) and tetracycline (3 μg/ml) at 30° C. and grown to an $OD_{600nm}$ ~0.5. 1.4 ml of this culture was transferred to each of 2 eppendorf tubes and 50 μl 10 arabinose added to one tube to induce expression of the Red/ET recombination proteins. Tubes were shaken for ~1 hour at 37° C. Induced and non-induced cells were pelleted in a bench top centrifuge and washed twice with chilled sterile water; resuspending and centrifuging to pellet the cells each time. The resulting pellets were suspended in about 30-40 μl of water and kept on ice. The 1.7 kb disruption fragment isolated previously was added to the induced and non-induced tubes and transferred to 1 mm Biorad electrocuvettes on ice. The samples were electroporated (Biorad Micropulser at 1.8 kV, resulting time constant ~4 ms) and 1 ml 2TY (no antibiotics) added and mixed to remove the cells from the cuvette. Cells were incubated for ~3 hours at 37° C. with shaking (1100 rpm, eppendorf thermomixer compact) before plating onto 2TY plates containing apramycin (50 μg/ml and kanamycin 25 μg/ml and incubating over night at 37° C. Colonies from the induced sample plates were streaked onto 2TY plates containing kanamycin at 50 μg/ml to purify and confirm introduction of the kanamycin resistance cassette. PCR on individual bacterial colonies was used to confirm the introduction of the cassette. Plasmids were prepared from these cultures and digested to confirm the expected plasmid pSGK270. Plasmids were then digested with NsiI to remove the marker fragment, and the remainder religated to produce the sfaA in-frame deletion construct pSGK271.

1.2 Conjugation of *Streptomyces* sp. A92-308110 (DSM9954) and Introduction of an sfaA Deletion Plasmid pSGK271 was transformed into *E. coli* ET12567 pUZ8002 using standard techniques and selected on 2TY plates containing apramycin (50 μg/ml), kanamycin (25 μg/ml) and chloroamphenicol (10 μg/ml). The resulting strain was inoculated into 3 ml liquid 2TY containing apramycin (50 μg/ml), kanamycin (25 μg/ml) and chloroamphenicol (10 μg/ml) and incubated overnight at 37° C., 250 rpm. 0.8 ml of this culture was used to inoculate 10 ml liquid 2TY containing apramycin (50 μg/ml), kanamycin (25 μg/ml) and chloroamphenicol (10 μg/ml) in a 50 ml Falcon tube and incubated at 37° C. 250 rpm until $OD_{600\ nm}$ ~0.5 was reached. The resulting culture was centrifuged at 3500 rpm for 10 minutes at 4° C., washed twice with 10 ml 2TY media using centrifugation to pellet the cells after each wash. The resulting pellet was resuspended in 0.5 ml 2TY and kept on ice before use. This process was timed to coincide with the complete preparation of *Streptomyces* spores described below.

Spores of *Streptomyces* sp. A92-308110 (DSM9954) (Biot-4370) were harvested from a 1-2 week old confluent plate by resuspending in ~3 ml 20% glycerol. Spores were centrifuged (5000 rpm, 10 minutes room temperature) and washed twice with 50 mM TES buffer before resuspending in 1 ml 50 mM TES buffer and splitting between 2 eppendorf tubes. These tubes were heat shocked at 50° C. for 10 minutes in a water bath before adding 0.5 ml 2TY and incubating in an Eppendorf Thermomixer compact at 37° C. for 4-5 hours.

The prepared *E. coli* ET12567 pUZ8002 pSGK271 and Biot-4370 were mixed at ratios 1:1 (250 μL each strain) and 1:3 (100 μL *E. coli*) and immediately spread on R6 plates and transferred to a 37° C. incubator. After approximately 2 hours incubation these plates were overlaid with 2 ml of sterile water containing nalidixic acid to give a final in-plate concentration of 25 μg/L. Plates were returned to the 37° C. incubator overnight before overlaying with 2 ml of sterile water containing apramycin to give a final in-plate concentration of 20-25 μg/L. Ex-conjugant colonies appearing after ~4-7 days were patched to ISP4 media containing apramycin (25 μg/L) and nalidixic acid (25 μg/L) and incubated at 37° C. Once adequate mycelial growth was observed strains were repatched to ISP4 media containing apramycin (25 μg/L) at 37° C. and allowed to sporulate. Strains were then subcultured three times (to promote removal of the temperature sensitive plasmid) by patching to ISP4 (without antibiotic) and incubating at 37° C. for 3-4 days. Strains were finally patched to ISP4 and incubated at 28° C. to allow full sporulation (5-7 days). Spores were harvested and serially diluted onto ISP4 plates at 28° C. to allow selection of single colonies. Sporulated single colonies were doubly patched to ISP4 plates with or without apramycin (25 µg/L) to confirm loss of plasmid and allowed to grow ~7 days before testing for production of sanglifehrins.

1.3 Screening Strains for Production of Sanglifehrins in Falcon Tubes

A single ~7 mm agar plug of a well sporulated strain was used to inoculate 7 ml of sterile SM25-3 media and incubated at 27° C. 200 rpm in a 2" throw shaker. After 48 hours of growth 0.7 ml of this culture was transferred to a sterilised falcon tube containing 7 ml of SGP2 media with 5% HP20 resin. Cultures were grown at 24° C. 300 rpm on a 1 inch throw shaking incubator for 5 days before harvest. 0.8 ml bacterial culture was removed and aliquoted into a 2 ml eppendorf tube ensuring adequate dispersal of the resin in throughout the culture prior to aliquoting. 0.8 ml acetonitrile and 15 µl of formic acid were added and the tube mixed for about 30 minutes. The mixture was cleared by centrifugation and 170 µl of the extract removed into a HPLC vial and analysed by HPLC.

1.4 Analysis of Strains for Reversion to Wild Type or sfaA Phenotype.

Extracts of strains were analysed by HPLC. Strains that produced sanglifehrin A and B were not analysed further as these had reverted to wild type. Strains lacking sanglifehrin A and B production showed small levels (~1-2 mg/L) of a peak retention time 6.5 minutes that displayed a sanglifehrin like chromophore. Analysis by LCMS indicated this peak had a m/z 1073, −16 units from the expected m/z of sanglifehrin. It was postulated this peak was due to incorporation of phenylalanine in absence of meta-hydroxytyrosine.

Eight strains showing loss of sanglifeherin production were subsequently regrown to assess whether the potential sfaA mutation could be complemented chemically allowing a mutasynthetic process to novel sanglifehrins. Strains were grown in SM25-3 seed media for 48 hours before transferring to SGP2 production media with 5% resin. After a further 24 hours growth strains were fed in triplicate with 2 mM DL meta-hydroxytyrosine (addition of 100 ul of a 0.16M solution in 1M HCL) or 2 mM L-phenylalanine with an unfed strain used as control. Strains were also fed pipecolic acid (2 mM) in methanol) to enhance product yields. Strains were harvested after a further 4 days growth and extracted and analysed by HPLC. Meta-hydroxy tyrosine was shown to completely complement the sfaA mutation and addition of L-phenylalanine increased levels of the −16 amu compound. Strain Biot-4585 was chosen for further study as the sfaA deletion mutant.

Example 2

Other Methods for Construction of the sfaA Deletion Construct

Other methods can be used to generate sfaA deletion mutants. Examples include sfaA insertional inactivation mutants (such as example 12 from WO2010/034243). This strain was generated as described in WO2010/034243, and given the strain designation BIOT-4452.

In an alternative procedure to generate the deletion of sfaA two oligonucleotides 15209F 5'-CAGAGAATTCGCGG-TACGGGGCGGACGACAAGGTGTC-3' (SEQ ID NO. 4) and 17219R 5'-GCGCATGCATGTGCCGGTGCCGGTC-CGCGAGCCGCTTGG-3' (SEQ ID NO. 5) are used to amplify an upstream region of homology using cosmid TL3006 (SEQ ID NO. 3) as template and KOD DNA polymerase. The amplified product is treated with T4 polynucleotide kinase (NEB) and cloned into pUC18 that has been dephosphorylated by treating with shrimp alkaline phosphatase (Roche). The resulting construct is checked by restriction digestion and thoroughly sequenced to ensure the desired sequence is generated and that errors have not been introduced during polymerase amplification. This construct is digested with EcoRI and NsiI and the products analysed by gel electrophoresis. The desired sequence-containing band (i.e. upstream homology ~2 kb) is excised from the gel and purified using standard procedures (QiaEX resin). A second series of oligonucleotides: 17766F 5'-CCTCATGCATCTG-GAGGACGTCGCAGGTGAATTCTGGGCG-3' (SEQ ID NO. 6) and 19763R 5'-GGGCAAGCTTCTCCTGGCTGAGCT-TGAACATCG-3' (SEQ ID NO. 7) are used to amplify a downstream region of homology using cosmid TL3006 (SEQ ID NO. 3) as template and KOD DNA polymerase. The amplified product is treated with T4 polynucleotide kinase (NEB) and cloned into pUC18 that has been dephosphorylated by treating with shrimp alkaline phosphatase (Roche). The resulting construct is analysed by restriction digestion and thoroughly sequenced to ensure the desired sequence is generated and that errors have not been introduced during polymerase amplification. This construct is digested with HindIII and NsiI and the products analysed by gel electrophoresis. The desired sequence-containing band (i.e. downstream homology ~2 kb) is excised from the gel and purified using standard procedures (QiaEX resin). Vector pKC1139 is digested with EcoRI and HindIII and the large vector fragment isolated by gel electrophoresis and purified by standard methods (QiaEX resin). The isolated upstream and downstream homology fragments are then cloned into this fragment of pKC1139 in a three-way ligation to generate the desired sfaA deletion construct.

In a further alternative procedure for generation of a sfaA deletion construct commercial gene synthesis (i.e. Genscript or other vendor) is used to generate a construct containing the desired sequence (SEQ ID NO. 8). This purchased construct is digested using BamHI and XbaI to excise the sequence of interest and the products analysed by gel electrophoresis. The desired sequence-containing band (−4 kb) is excised from the gel and purified using standard procedures. Vector pKC1139 is digested with BamHI and XbaI and the large fragment isolated by gel electrophoresis and purified by standard methods. The two isolated fragments are then ligated together to generate the desired sfaA deletion construct.

These alternative sfaA deletion constructs are introduced into *Streptomyces* sp. A92-308110 (DSM9954) by conjugation and selection for the secondary cross using the methods described in Example 1.2. Growth and analysis of strains constructed in this way also follows the methods described in Example 1.2

Example 3

Array Feed of the sfaA Deletion Mutant

Spore stocks of a mutant disrupted in sfaA (BIOT-4452 or BIOT-4585) were prepared after growth on MAM, ISP4, ISP3 or ISP2 medium, and preserved in 20% w/v glycerol in distilled water and stored at −80° C. Vegetative cultures (seed cultures) were prepared by inoculating spore stock (1% v/v) into 7 mL seed medium (SM25 medium) in 50 mL centrifuge tubes with foam plugs. The culture tubes were incubated at 27° C., 250 rpm (5 cm throw) for 48 h. From the seed culture 10% (v/v) was transferred into 7 mL production medium SGP-2 in 50 mL centrifuge tubes with foam plugs. Cultivation was carried out at 24° C. and 300 rpm (2.5 cm throw). For production of sanglifehrin mutasynthetic analogues, 0.05 mL of a 0.32 M solution (in 1N HCl) of the feed compound (mutasynthon) was added to each tube at 24 hours post inoculation to give a final concentration of 2 mM. Additionally, 0.05 ml of a 0.32 M solution of piperazic acid (in methanol) was added to each tube at 24 hours to give a final concentration of 2 mM. Cultivation was continued for an additional four days post feeding.

Samples were extracted by transferring 0.8 ml of the whole broth into a 2 ml capped eppendorf tube. 0.8 ml of acetonitrile was added, along with 0.015 ml of formic acid. The mixture was then shaken for 30 minutes on a vibrax. The tube was then centrifuged at 13000 rpm for 10 minutes and 0.15 ml of the supernatant was removed for analysis. Extracts were analysed as described in general methods.

Table 1 shows the mutasynthons that were fed in this way, along with the LCMS H+ and Na+ adducts, anticipated molecular mass and retention time of the sanglifehrin mutasynthetic products observed. The major peaks, relating to the sanglifehrin A analogues, are shown. In all cases, LCMS peaks were also seen for the sanglifehrin B analogues (Mass −18).

Example 4

Isolation of 63-Fluoro Sanglifehrin A, Intermediate Compound 14

Fermentation carried out as described in general methods utilising methyl 2-amino-3-(3-fluoro-5-hydroxyphenyl)propanoate and DL-piperazic acid as precursors, both were added at 26 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using a magnetic stirrer. The acetonitrile extract was recovered either by centrifugation or by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (1.3 g).

The crude extract (1.3 g) was dissolved in ethyl acetate (2 ml) and loaded onto a silica gel column (10×2 cm) conditioned with ethyl acetate (500 ml). The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (278 mg) was dissolved in methanol (1.8 ml) and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (20 mg).

TABLE 1

| mutasynthon fed | mutasynthon name | $[M - H]^-$ observed (m/z) | $[M + Na]^+$ observed (m/z) | molecular mass (amu) | retention time (minutes) |
| --- | --- | --- | --- | --- | --- |
| (structure: HO-phenyl(F)-CH2-CH(NH2)-CO2H) | 2-amino-3-(3-fluoro-5-hydroxyphenyl)propanoic acid | 1106.4 | 1130.4 | 1107.4 | 5.7 |
| (structure: HO-phenyl(F)-CH2-CH(NH2)-CO2Me) | methyl 2-amino-3-(3-fluoro-5-hydroxyphenyl)proprionate | 1106.4 | 1130.4 | 1107.4 | 5.7 |

Example 5

Synthesis of diethyl (2-(1,2-oxazinan-2-yl)-2-oxoethyl)phosphonate

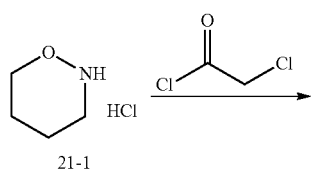

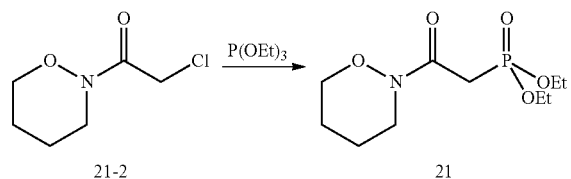

To a solution of 21-1 (ChemCollect, Germany)(100 mg, 0.81 mmol), Et$_3$N (246 mg, 2.43 mmol) in dry DCM (5 mL) was added dropwise chloroacetyl chloride (138 mg, 1.22 mmol). The reaction mixture was stirred at room temperature for 3 h, poured into ice water, and extracted with ethyl acetate. The organic layer was washed with brine and dried over Na$_2$SO$_4$, filtered, concentrated in vacuo. The residue (21-2) was used to the next step without any further purification. (123 mg, 90% yield).

A mixture of 21-2 (123 mg, 0.75 mmol) and triethyl phosphite (250 mg, 1.50 mmol) were stirred at 140° C. for 6 h. The reaction mixture was cooled to room temperature and was purified by flash chromatography to yield 21.

Alternative synthesis of synthesis of diethyl (2-(1,2-oxazinan-2-yl)-2-oxoethyl)phosphonate, 21

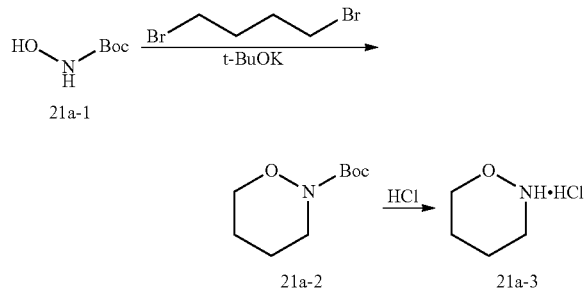

General procedure for preparation of 21a-2

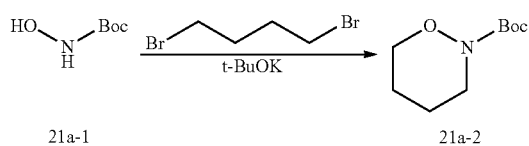

To a solution of t-BuOK (84.0 g, 0.75 mol) in tetrahydrofuran (2.0 L) was added 21a-1 (50.0 g, 0.38 mol) portion-wise at room temperature. the mixture was stirred for 1 h at room temperature. 1,4-Dibromobutane (81.2 g, 0.38 mol) was added dropwise at room temperature. Then the mixture was stirred at 80° C. for 16 h. After cooling down, water (2000 mL) was added, the mixture was extracted with ethyl acetate (2×1000 mL). The combined organic later was dried over anhydrous Na$_2$SO$_4$ for 16 h, after filtration and concentration, the residue was purified by silica-gel column chromatography (eluent: petroleum ether:ethyl acetate=100:1 to 10:1) to give 21a-2 (57 g) as a colorless oil.

General Procedure for Preparation of 21a-3

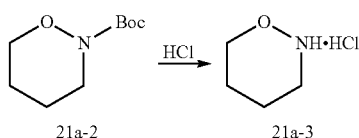

To a solution of 21a-2 (55 g, 0.29 mol) in tert-butyl methyl ether, TBME (80 mL) was added a solution of 4N HCl (600 ml, in TBME) at room temperature, the mixture was stirred for 3 h at room temperature. The precipitated solid was filtered and washed with TBME (50 mL) to give 21a-3 (30 g) as a white solid.

General Procedure for Preparation of 21

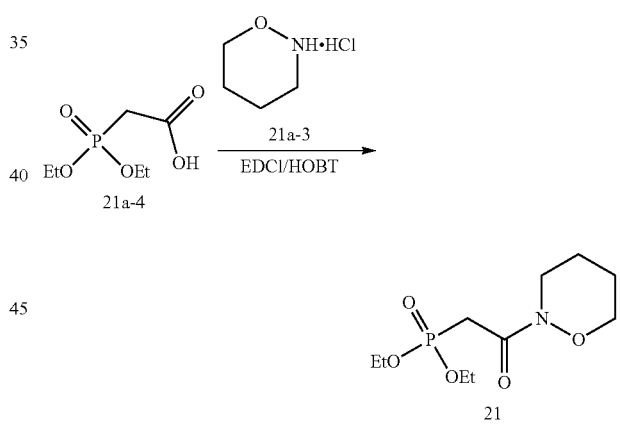

To a stirred solution of 21a-4 (35 g, 0.18 mol), hydroxybenzotriazole (HOBT) (29 g, 0.21 mol) and Et$_3$N (71 mL, 0.51 mol) in anhydrous dichloromethane (550 mL) was added 1-Ethyl-3-(3-dimethylaminopropyl)carbodiimide (EDCI) (41 g, 0.21 mol) portion-wise at 0° C. The reaction mixture was stirred at 0° C. for 0.5 h, then 21a-3 (24 g, 0.20 mol) was added at 0° C. and stirred for 16 h. Then TLC (petroleum ether/ethyl acetate: 3/1) showed that the reaction was complete. At this time the reaction mixture was slowly poured into water (500 mL) with vigorous stirring. The mixture was extracted with dichloromethane (2×200 mL). The combined organic layer was washed with brine (2×100 mL), dried with Na$_2$SO$_4$, filtered and concentrated to afford crude product. Chromatography (petroleum ether/ethyl acetate, 100:1 to 10:1) gave 21 (38 g) as a yellow oil.

Example 6
Preparation of Intermediate Compound 23-3
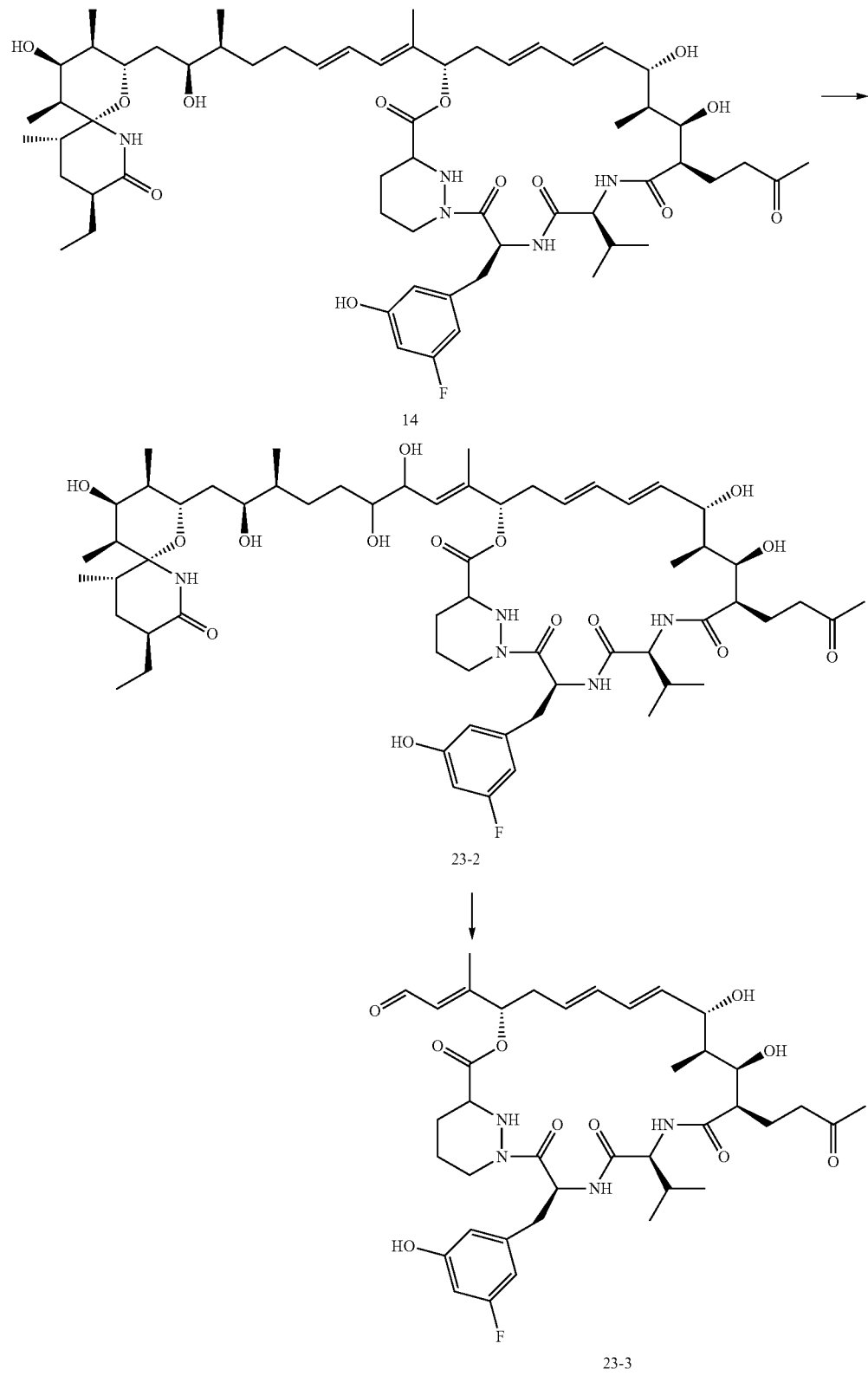

To a stirred solution of 14 (430 mg, 0.38 mmol), (DHQ)$_2$PHAL (18.6 mg, 0.024 mmol), osmium tetroxide (0.156 mL, 0.012 mmol) in tert-butyl alcohol (2.5 wt %, 0.079 mmol/ml), and methanesulfonamide (74 mg, 0.77 mmol) in 20 mL tert-butyl alcohol were added at room temperature, a solution of potassium ferricyanide (382 mg, 1.16 mmol) and potassium carbonate (160 mg, 1.16 mmol) in 20 mL water, resulting in a brown emulsion. After 2 h a solution of sodium sulfite was added, and stirring was continued for 20 min. The resulting mixture was extracted with ethyl acetate (3×50 ml). The combined organic layers were washed with brine, dried over anhydrous sodium sulfate, filtered, and concentrated under reduced pressure, purified by reverse-phase flash chromatography to yield 23-2 as a white solid.

To a stirred solution of 23-2 (240 mg, 0.21 mmol) in 24 mL of a 2:1 mixture of THF and water was added sodium periodate (91 mg, 0.42 mmol). The resulting mixture was stirred at room temperature for 3 h, and then saturated aqueous sodium bicarbonate was added. This mixture was extracted with three portions of ethyl acetate. The combined organic layers were washed with one portion of water and two portions of saturated brine, dried over anhydrous sodium sulfate, filtered, and concentrated under reduced pressure. The residue was purified by reverse-phase flash chromatography to yield 23-3.

Example 7

Preparation of Compound 24

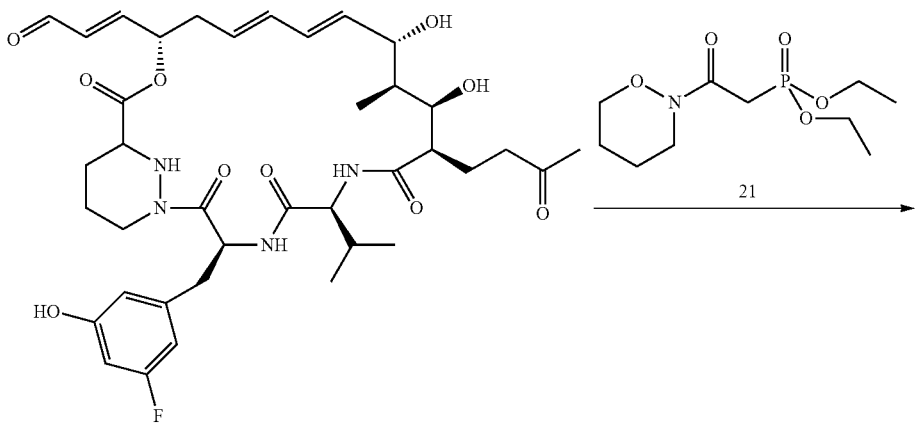

23-3

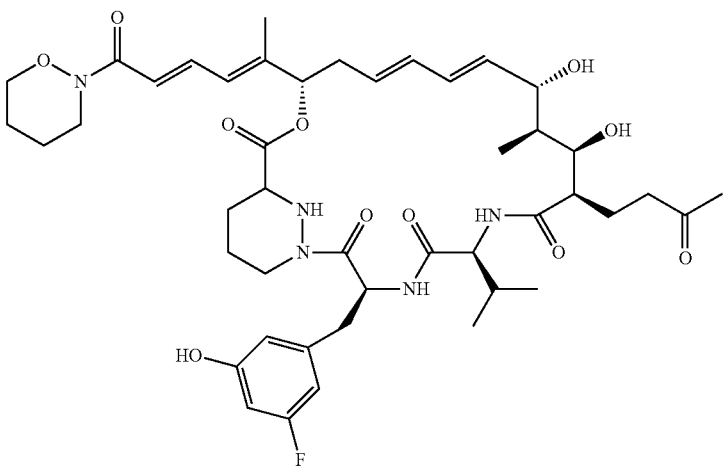

24

To a solution of 21 (42 mg, 0.168 mmol) in THF (2.0 mL) was added NaH (1.2 mg, 0.05 mmol) in anhydrous THF (0.2 mL) at 0° C. with stirring. The solution was then stirred at 20° C. until it became clear. Then 23-3 (30 mg, 0.042 mmol) was added to the clear solution and the mixture stirred at 20° C. for 2 h. The mixture was quenched with water (10 mL) and extracted with ethyl acetate (3×20 mL). The organic layer was washed with brine and dried over $Na_2SO_4$, filtered and reduced in vacuo. The residue was purified by preparative HPLC to obtained 24 as an amorphous white solid.

Example 8

Preparation of Compound 24 in Solid Crystalline Form (Form I)

10 mg of amorphous compound 24 was slurried in methyl isobutyl ketone (MIBK) (500 µL, 50 volumes) and then the temperature was cycled between ambient and 40° C. every 4 hours for a total of 5 days. The resulting solid was isolated by decanting off excess solvent followed by drying under vacuum to yield compound 24 in solid crystalline form (Form I). The XRPD pattern of Form I of compound 24 is illustrated in FIG. 2 and the peaks and their relative intensities are listed in Table 2 below. The method of obtaining the XRPD data is described in the General Methods.

TABLE 2

| Peak No. | Position [°2Theta] | Relative Intensity [%] |
|---|---|---|
| 1 | 6.2097 | 6.86 |
| 2 | 6.5031 | 7.76 |
| 3 | 8.2581 | 27.43 |
| 4 | 8.4838 | 33.64 |
| 5 | 9.5994 | 23.88 |
| 6 | 10.0981 | 8.54 |
| 7 | 11.0546 | 29.76 |
| 8 | 12.5883 | 14.81 |
| 9 | 13.1703 | 7.1 |
| 10 | 13.9184 | 100 |
| 11 | 14.2891 | 13.04 |
| 12 | 14.9759 | 10.37 |
| 13 | 15.3159 | 5.81 |
| 14 | 16.8844 | 18.15 |
| 15 | 17.1816 | 9.72 |
| 16 | 17.7384 | 53.03 |
| 17 | 18.1703 | 9.02 |
| 18 | 18.5613 | 32.19 |
| 19 | 19.0241 | 52.81 |
| 20 | 19.4201 | 5.08 |
| 21 | 20.0954 | 13.7 |
| 22 | 20.449 | 63.25 |
| 23 | 20.8962 | 43.44 |
| 24 | 21.1871 | 15.02 |
| 25 | 21.6388 | 16.08 |
| 26 | 23.0029 | 50.8 |
| 27 | 23.2869 | 17.19 |
| 28 | 23.6883 | 17.16 |
| 29 | 24.1071 | 13.7 |
| 30 | 24.2587 | 19.55 |
| 31 | 24.9948 | 13.34 |
| 32 | 25.209 | 26.16 |
| 33 | 25.9577 | 10.06 |
| 34 | 26.4298 | 9.38 |
| 35 | 27.3687 | 11.1 |
| 36 | 29.0171 | 7.95 |
| 37 | 29.5603 | 5.14 |
| 38 | 30.0609 | 7.35 |
| 39 | 30.5824 | 6.5 |
| 40 | 32.1814 | 4.39 |
| 41 | 32.6521 | 6.74 |
| 42 | 33.5957 | 6.6 |
| 43 | 34.7946 | 9.04 |

Example 9

Biological Data—HCV Replicon and Analysis

Compounds were analysed in the genotype 1b replicon assay using Huh5.2 cells as described in the General Methods. Cyclosporine A, 1, DEBIO-025, 2, sanglifehrin A, 5, and the hydroxymacrocycle, 6 were included as a comparison.

| Compound | EC50 (µM) | CC50 (µM) | Selectivity index (CC50/EC50) |
|---|---|---|---|
| Cyclosporine A, 1 | 0.62 | 28 | 52 |
| DEBIO-025, 2 | 0.096 | 11.2 | 111 |
| Sanglifehrin A, 5 | 0.318 | 9.1 | 28.7 |
| Hydroxymacrocycle, 6 | 8.4 | 83.6 | 9.9 |
| 24 | 0.033 | >100 | >3030 |

As can be seen, the compound of the invention, 24 is significantly more potent in the Huh5.2 replicon assay (as shown by the low $EC_{50}$), with significantly better selectivity against the cell line (as shown by a high selectivity index) as compared to CsA, Debio-025, SfA and the hydroxymacrocycle.

Example 10

Biological Data—Activity Against HIV

Compounds were analysed in an HIV antiviral assay using HeLa cells as described in the General Methods. Cyclosporine A, 1, DEBIO-025, 2, and the HIV antivirals emtricitabine and tenofovir were included as a comparison.

| Compound | HeLa cells $EC_{50}$ (µM) |
|---|---|
| Cyclosporine A, 1 | 5.3 |
| DEBIO-025, 2 | 1.5 |
| Emtricitabine | 0.4 |
| Tenofovir | 1.05 |
| 24 | 0.13 |

As can be seen, the compound of the invention, 24, is significantly more potent than CsA, DEBIO-025, emtricitabine and tenofovir at inhibiting HIV infection in this assay.

Example 11

Biological Data—Mouse In Vivo Oral and iv PK

To assess the pharmacokinetics of the compounds in an in vivo setting, compounds were dosed po at 10 or 5 mg/kg and iv at 1 mg/kg to groups of CD1 mice. Pharmacokinetic analysis was carried out as described in the general methods. The PK parameters are shown below.

| Compound | Dose level (mg/kg) | Clearance (L/hr/kg) | po $AUC_{last}$ (ng * hr/mL) |
|---|---|---|---|
| Sanglifehrin A, 5 | 10 | 0.054 | 2332 |
| 24 | 5 | 0.017 | 8223 |

As can be seen, compounds 24 has reduced clearance and increased oral exposure (as shown by a high po $AUC_{last}$), compared to sanglifehrin A.

Example 12

Biological Data—Inhibition of CypA PPIase Activity

To assess the direct inhibition of CypA Peptidyl Prolyl cis-trans Isomerase (PPIase) activity, a method was used as described in the general methods. Cyclosporine A, 1, DEBIO-025, 2 and Sanglifehrin A, 5 were included as controls.

| Compound | CypA PPIase $IC_{50}$ (nM) |
|---|---|
| Cyclosporine A, 1 | 9.7 |
| DEBIO-025, 2 | 0.8 |
| Sanglifehrin A, 5 | 2.4 |
| 24 | 0.31 |

As can be seen, compound of the invention, 24, inhibits CypA PPIase activity more potently than Sanglifehrin A, DEBIO-025 and Cyclosporine A.

Example 13

Biological Data—Inhibition of Bilirubin Transporters

To assess the potential of off-target inhibition of bilirubin transporters, thought to be the reason for the dose-limiting hyperbilirubinaemia seen with DEBIO-025, in vitro analysis of transporter inhibition was carried out as described in the general methods.

| Compound | OATP1B1 $IC_{50}$ (µM) | OATP1B3 $IC_{50}$ (µM) | MRP2 $IC_{50}$ (µM) | MRP3 $IC_{50}$ (µM) |
|---|---|---|---|---|
| Cyclosporine A, 1 | 0.85 | 0.13 | 4.1 | 3.1 |
| DEBIO-025, 2 | 0.45 | 0.19 | 16.0 | >50 |
| 24 | 4.3 | 1.8 | >50 | >50 |

As can be seen, the compound of the invention, 24, shows much less inhibition of conjugated and unconjugated bilirubin transporters as compared to DEBIO-025 and Cyclosporine A.

Example 14

Biological Data—Inhibition of Xenobiotic Transporters

To assess the potential of Drug Drug Interactions (DDIs) via inhibition of xenobiotic transporters, in vitro analysis of P-glycoprotein (Pgp/MDR1) and Bile Salt Export Pump (BSEP) inhibition was carried out as described in the general methods.

| Compound | Pgp $IC_{50}$ (µM) | BSEP $IC_{50}$ (µM) |
|---|---|---|
| Cyclosporine A, 1 | 0.73 | 0.46 |
| DEBIO-025, 2 | 0.72 | 0.18 |
| 24 | >50 | 12.3 |

As can be seen, the compound of the invention, 24, shows much less inhibition of xenobiotic transporters, potentially involved in Drug-Drug Interactions, as compared to DEBIO-025 and Cyclosporine A.

REFERENCES

Appel, N., T. Schaller, et al. (2006). "From structure to function: new insights into hepatitis C virus RNA replication." *J Biol Chem* 281(15): 9833-6.

Banteli, R., J. Wagner, et al. (2001). "Synthesis of derivatives of the novel cyclophilin-binding immunosuppressant sanglifehrin A with reduced numbers of polar functions." *Bioorg Med Chem Lett* 11(12): 1609-12.

Chatterji, U., M. Bobardt, et al. (2009). "The isomerase active site of cyclophilin a is critical for HCV replication." *J Biol. Chem.*

Colgan, J., M. Asmal, et al. (2000). "Isolation, characterization and targeted disruption of mouse ppia: cyclophilin A is not essential for mammalian cell viability." *Genomics* 68(2): 167-78.

Crabbe, R., G. Vuagniaux, et al. (2009). "An evaluation of the cyclophilin inhibitor Debio 025 and its potential as a treatment for chronic hepatitis C." *Expert Opin Investig Drugs* 18(2): 211-20.

Dolinski, K., S. Muir, et al. (1997). "All cyclophilins and FK506 binding proteins are, individually and collectively, dispensable for viability in *Saccharomyces cerevisiae*." *Proc Natl Acad Sci USA* 94(24): 13093-8.

E. Lawitz, R. R., T. Nguyen, M. Huang, J. Ke, J. Praestgaard, D. Serra, M. Koziel, T. Evans (2009). "Safety And Antiviral Efficacy Of 14 Days Of The Cyclophilin Inhibitor Nim811 In Combination With Pegylated Interferon 0.2a In Relapsed Genotype 1 Hcv Infected Patients." *Journal of Hepatology* 50(S1): S379.

Egorin, M. J., T. F. Lagattuta, et al. (2002). "Pharmacokinetics, tissue distribution, and metabolism of 17-(dimethylaminoethylamino)-17-demethoxygeldanamycin (NSC 707545) in CD2F1 mice and Fischer 344 rats." *Cancer Chemother Pharmacol* 49(1): 7-19.

Fehr, T., J. Kallen, et al. (1999). "Sanglifehrins A, B, C and D, novel cyclophilin-binding compounds isolated from *Streptomyces* sp. A92-308110. II. Structure elucidation, stereochemistry and physico-chemical properties." *J Antibiot (Tokyo)* 52(5): 474-9.

Flisiak, R., A. Horban, et al. (2008). "The cyclophilin inhibitor Debio-025 shows potent anti-hepatitis C effect in patients coinfected with hepatitis C and human immunodeficiency virus." *Hepatology* 47(3): 817-26.

Furniss, B. S., Furniss, A. I., Vogel, A. I., Ed. (1989). *Vogel's Textbook of Practical Organic Chemistry*, Prentice Hall.

Gaither, L. A., Borawski, J., Anderson, L. J., Balabanis, K. A. et al., (2010). "Multiple cyclophilins involved in different cellular pathways mediate HCV replication" *Virology* 397: 43-55

Glavinas, H., Krajcsi, P., Cserepes, J., Sarkadi, B. (2004). "The role of ABC transporters in drug resistance, metabolism and toxicity." *Curr. Drug. Deliv.* 1(1): 27-42.

Gomez, L., H. Thibault, et al. (2007). "Inhibition of mitochondrial permeability transition improves functional recovery and reduces mortality following acute myocardial infarction in mice." *Am J Physiol Heart Circ Physiol* 293 (3): H1654-61.

Goto, K., Watashi, K., Inoue, D., Hijikata, M., Shimotohno, K. (2009) "Identification of cellular and viral factors related to anti-hepatitis C virus activity of cyclophilin inhibitor" *Cancer Science* 100(10): 1943-1950

Hanoulle, X., Badillo A, Wieruszeski J M, Verdegem D, Landrieu I, Bartenschlager R, Penin F, Lippens G (2009). "Hepatitis C virus NS5A protein is a substrate for the Peptidyl-Prolyl cis/trans isomerase activity of Cyclophilins A and B." *J Biol Chem.*

Hartel, C., P. Iblher, et al. (2006). "Immunosuppressive activity of the immunophilin-binding drug Sanglifehrin A in human whole blood: potent inhibition of interleukin-6 produced by lymphocytes and monocytes." *Scand J Immunol* 63(1): 26-34.

Herrler, M., H. Bang, et al. (1994). "Cloning and characterization of ppiB, a *Bacillus subtilis* gene which encodes a cyclosporin A-sensitive peptidyl-prolyl cis-trans isomerase." *Mol Microbiol* 11(6): 1073-83.

Hite, M., Turner, S., Federici, C. (2003). "Part 1: Oral delivery of poorly soluble drugs". *Pharmaceutical Manufacturing and Packing Sourcer*. Summer 2003 issue.

Immecke, S. N., Baal., N, et al. (2011). "The Cyclophilin-Binding Agent Sanglifehrin A Is a Dendritic Cell Chemokine and Migration Inhibitor." PLOS one 6(3):e18406

Inoue, K., K. Sekiyama, et al. (2003). "Combined interferon alpha2b and cyclosporin A in the treatment of chronic hepatitis C: controlled trial." *J Gastroenterol* 38(6): 567-72.

Inoue, K., T. Umehara, et al. (2007). "Evaluation of a cyclophilin inhibitor in hepatitis C virus-infected chimeric mice in vivo." *Hepatology* 45(4): 921-8.

Ishii, N., K. Watashi, et al. (2006). "Diverse effects of cyclosporine on hepatitis C virus strain replication." *J Virol* 80(9): 4510-20.

Ke, J., E. L., R. Rozier, T. Marbury, N. Nguyen, D. Serra, K. Dole, J. Praestgaard, M. Huang, T. Evans (2009). "Safety, And Tolerability Of Nim811, A Novel Cyclophilin Inhibitor For Hcv, Following Single And Multiple Ascending Doses In Healthy Volunteers And Hcv-Infected Patients." *Journal of Hepatology* 50(S1): S229.

Jacobson, I., McHutchison, J G, Sulkowski, M. (2007). *Gastroenterol & Hepatol* 3(S34): 1-10.

Kallen, J., R. Sedrani, et al. (2005). "Structure of human cyclophilin A in complex with the novel immunosuppressant sanglifehrin A at 1.6 A resolution." *J Biol Chem* 280 (23): 21965-71.

Kawasaki, H., E. S. Mocarski, et al. (2007). "Cyclosporine inhibits mouse cytomegalovirus infection via a cyclophilin-dependent pathway specifically in neural stem/progenitor cells." *J Virol* 81(17): 9013-23.

Konig, J. H., Glaeser, M. Keiser, K. Mandery, U. Klotz and M. F. Fromm (2010), *Drug Metab Dispos*, 39, 1097-1102.

Manns, M. P., G. R. Foster, et al. (2007). "The way forward in HCV treatment—finding the right path." *Nat Rev Drug Discov* 6(12): 991-1000.

Martin Cabrejas, L. M., S. Rohrbach, et al. (1999). "Macrolide Analogues of the Novel Immunosuppressant Sanglifehrin New Application of the Ring-Closing Metathesis Reaction." *Angew Chem Int Ed Engl* 38(16): 2443-2446.

Mathy, J. E., S. Ma, et al. (2008). "Combinations of cyclophilin inhibitor NIM811 with hepatitis C Virus NS3-4A Protease or NS5B polymerase inhibitors enhance antiviral activity and suppress the emergence of resistance." *Antimicrob Agents Chemother* 52(9): 3267-75.

Melnikova, I. (2008). "Hepatitis C therapies." *Nature Rev Drug Disc* 7: 799-800.

Metternich, R., Denni, D., That, B, Sedrani, R. (1999). "Toward a Total Synthesis of the Immunosuppressant Sanglifehrin A. Preparation of Two Relay Compounds by Degradation and Their Use in the Reassembly of the Natural Product." *J. Org. Chem.* 64: 9632-9639.

Millay, D. P., M. A. Sargent, et al. (2008). "Genetic and pharmacologic inhibition of mitochondrial-dependent necrosis attenuates muscular dystrophy." *Nat Med* 14(4): 442-7.

Nelson, D. R., Ghalib, R. H., Sulkowski, M., Schiff, E., Rustgi, V., Pockros, P. J., Wang, C., Decosterd Kerhuel, D., and P. Grosgurin, Porchet, H., Crabbe, R. (2009). "Efficacy And Safety Of The Cyclophilin Inhibitor Debio 025 In Combination With Pegylated Interferon Alpha-2a And Ribavirin In Previously Null-Responder Genotype 1 Hcv Patients." *Journal of Hepatology* 50(S1): S40.

Niwa, T., Yamamoto, S, Saito, M, Shiraga, T, Takagi, A. (2007). "Effect of Cyclosporine and Tacrolimus on Cytochrome P450 Activities in Human Liver Microsomes." *Yakugaku Zasshi* 127(1): 209-216.

Paeshuyse, J., A. Kaul, et al. (2006). "The non-immunosuppressive cyclosporin DEBIO-025 is a potent inhibitor of hepatitis C virus replication in vitro." *Hepatology* 43(4): 761-70.

Parfieniuk, A., J. Jaroszewicz, et al. (2007). "Specifically targeted antiviral therapy for hepatitis C virus." *World J Gastroenterol* 13(43): 5673-81.

Pawlotsky, J. M. (2000). "Hepatitis C virus resistance to antiviral therapy." *Hepatology* 32(5): 889-96.

Pawlotsky, J. M. (2005). "Current and future concepts in hepatitis C therapy." *Semin Liver Dis* 25(1): 72-83.

Pawlotsky, J. M. (2006). "Virology of hepatitis B and C viruses and antiviral targets." *J Hepatol* 44(1 Suppl): S10-3.

Pemberton, T. J. and J. E. Kay (2003). "Cyclophilin sensitivity to sanglifehrin A can be correlated to the same specific tryptophan residue as cyclosporin A." *FEBS Lett* 555(2): 335-40.

Pockros, P. (2008). "Emerging Therapies for Chronic Hepatitis C Virus." *Gastroenterol and Hepatology* 4(10): 729-734.

Ptak, R. G., P. A. Gallay, et al. (2008). "Inhibition of human immunodeficiency virus type 1 replication in human cells by Debio-025, a novel cyclophilin binding agent." *Antimicrob Agents Chemother* 52(4): 1302-17.

Qu, X., Jiang, N. et al., (2011). "Cloning, sequencing and characterization of the biosynthetic gene cluster of sanglifehrin A, a potent cyclophilin inhibitor." *Mol. Biosyst.* 7:852-861

Robida, J. M., H. B. Nelson, et al. (2007). "Characterization of hepatitis C virus subgenomic replicon resistance to cyclosporine in vitro." *J Virol* 81(11): 5829-40.

Hopkins, S. D. H., E. Gavis, J. Lalezari, E. Glutzer, B. DiMassimo, P. Rusnak, S. Wring, C. Smitley, Y. and Ribeill (2009). "Safety, plasma pharmacokinetics, and anti-viral activity of SCY-635 in adult patients with chronic hepatitis C virus infection." *Journal of Hepatology* 50(S1): S36.

Sanglier, J. J., V. Quesniaux, et al. (1999). "Sanglifehrins A, B, C and D, novel cyclophilin-binding compounds isolated from *Streptomyces* sp. A92-308110.1. Taxonomy, fermentation, isolation and biological activity." *J Antibiot (Tokyo)* 52(5): 466-73.

Schneider, M. D. (2005). "Cyclophilin D: knocking on death's door." *Sci STKE* 2005(287): pe26.

Sedrani, R., J. Kallen, et al. (2003). "Sanglifehrin-cyclophilin interaction: degradation work, synthetic macrocyclic analogues, X-ray crystal structure, and binding data." *J Am Chem Soc* 125(13): 3849-59.

Seden, K. D. Back and S. Khoo (2010), *J Antimicrob Chemother*, 65, 1079-1085.

Smith, M. B. a. M., J., Ed. (2001). *March's advanced organic chemistry*, John Wiley and Sons Inc., UK.

Steinschulte, C., T. Taner, et al. (2003). "Cutting edge: sanglifehrin A, a novel cyclophilin-binding immunosuppressant blocks bioactive IL-12 production by human dendritic cells." *J Immunol* 171(2): 542-6.

Strader, D. B., T. Wright, et al. (2004). "Diagnosis, management, and treatment of hepatitis C." *Hepatology* 39(4): 1147-71.

Tropschug, M., I. B. Barthelmess, et al. (1989). "Sensitivity to cyclosporin A is mediated by cyclophilin in *Neurospora crassa* and *Saccharomyces cerevisiae*." *Nature* 342(6252): 953-5.

Vrolijk, J. M., A. Kaul, et al. (2003). "A replicon-based bioassay for the measurement of interferons in patients with chronic hepatitis C." *J Virol Methods* 110(2): 201-9.

Wring, S. C. Wille, C. Rewerts, R. Randolph, A. Scribner and S. Hopkins (2010), *Journal of Hepatology*, 52, S263

Yang, F., J. M. Robotham, et al. (2008). "Cyclophilin A is an essential cofactor for hepatitis C virus infection and the principal mediator of cyclosporine resistance in vitro." *J Virol* 82(11): 5269-78.

Zenke, G., U. Strittmatter, et al. (2001). "Sanglifehrin A, a novel cyclophilin-binding compound showing immunosuppressive activity with a new mechanism of action." *J Immunol* 166(12): 7165-71.

Zeuzem, S, and E. Herrmann (2002). "Dynamics of hepatitis C virus infection." *Ann Hepatol* 1(2): 56-63.

Zhang, L. H. and J. O. Liu (2001). "Sanglifehrin A, a novel cyclophilin-binding immunosuppressant, inhibits IL-2-dependent T cell proliferation at the G1 phase of the cell cycle." *J Immunol* 166(9): 5611-8.

All references including patent and patent applications referred to in this application are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:
1. A compound of formula (I):

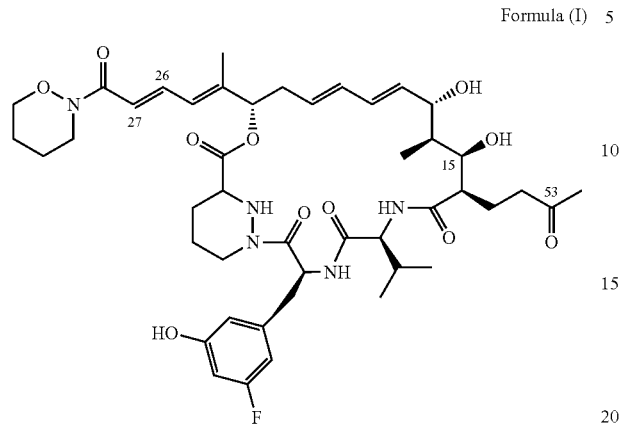

Formula (I)

including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl group and methanol; or a pharmaceutically acceptable salt thereof.

2. A compound according to claim 1 is solid crystalline form.

3. A compound according to claim 2 in the form of its Form I crystalline polymorph.

4. A pharmaceutical composition comprising a compound according to claim 1 together with a pharmaceutically acceptable diluent or carrier.

5. A pharmaceutical composition comprising a compound according to claim 1 together with a pharmaceutically acceptable diluent or carrier further comprising a second or subsequent active ingredient.

6. A method of treating an HCV, HBV, or HIV infection, which comprises administering to a subject a therapeutically effective amount of a compound according to claim 1.

7. A process for preparing a compound according to claim 1 which comprises reacting a compound of formula (V)

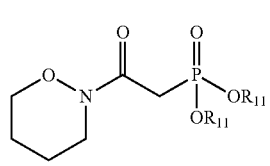

Formula (V)

wherein each $R_{11}$ is independently $C_{1-4}$ alkyl or benzyl; with an aldehydic macrocycle (compound of formula VI):

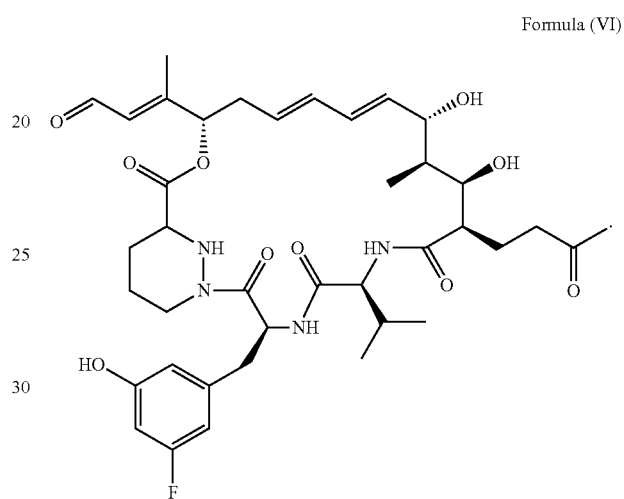

Formula (VI)

8. A process for the preparation of a compound of formula (I) in the form of its Form I crystalline polymorph according to claim 3 comprising the step of crystallising a compound of formula (I) from methyl isobutyl ketone.

* * * * *

```
                        SEQUENCE LISTING

<160> NUMBER OF SEQ ID NOS: 8

<210> SEQ ID NO 1
<211> LENGTH: 77
<212> TYPE: DNA
<213> ORGANISM: Artificial
<220> FEATURE:
<223> OTHER INFORMATION: Primer

<400> SEQUENCE: 1
cgctctgtgg cgcctggttt ccaagcggct cgcggaccgg caccggcaca tgcataatta      60
accctcacta aagggcg                                                    77

<210> SEQ ID NO 2
<211> LENGTH: 78
<212> TYPE: DNA
<213> ORGANISM: Artificial
<220> FEATURE:
<223> OTHER INFORMATION: Primer

<400> SEQUENCE: 2
tggatgtatc gtcgcaggac gcccagaatt cacctgcgac gtcctccaga tgcattaata      60
cgactcacta tagggctc                                                   78

<210> SEQ ID NO 3
<211> LENGTH: 46596
<212> TYPE: DNA
<213> ORGANISM: Artificial
<220> FEATURE:
<223> OTHER INFORMATION: Cosmid

<400> SEQUENCE: 3
acaccggcca caccggcggc ggcctgcgtg tgcccgatgt tggacttcac cgaaccgagc      60
cacagcggct cgtcccgctc ctgcccgtag gtggcgagca gcgcctgcgc ctcgatcggg     120
tcgcccagcc gcgtgcccgt accgtgcgcc tccaccgcgt ccacgtccgc gggcgtgagc     180
ccggcaccgg agagcgcctg acggatcacc cgctgctgcg aaggaccgtt cggggccgtc     240
agaccgttcg acgcgccgtc ctggttgatc gcggtgccgc gtacgacggc cagtacctgg     300
tggccgtggc ggcgggcgtc ggagagccgt tccacgagga gcatgccggc gccctcggac     360
cagccggtgc cgtcggccgc ggcggcgaag gacttgcagc ggccgtccac ggccaggccg     420
```

```
cgctggcggg agaagtcgac gaagacgtcg ggggcggaca tgacggtgac accgccggcc    480
agcgccatcg agcactcgcc gctgcgcagc gcctggatcg cccagtgcag ggcgaccagc    540
gacgccgagc acgcggtgtc cacggtgacc gcagggcctt ccaggccgag gacgtaggcg    600
atgcggcccg acagcacgct ggcggagttg ccgatgccga cgtagccctc gcgctctcg    660 acggtcctgc gcacgagctg ggcatagtcc tggccgttgg tgccgaggta gacgccgacg    720
tccgcgccgc gcagggactt cggggtcgatg ccggcgcgtt cgacggcctc ccaggcggtc    780
tccagggcca gccgctgctg cgggtccatc gccagcgcct cgcgcggcga gatcccgaag    840
aagtccgcgt cgaacccggc gacgtccgcg aggaagccgc cctcccgcac gtacgacgtg    900
cccgcgtgct ccggatccgg gtggaagagg cccgcgaggt cccagccccg gtcgtcgggg    960
aacggggtga gcgcgtcgcg ctcgtcggcg agcagccgcc acaggtcctc gggcgaggtc   1020
acgccgccgg ggtaccggca cgccatgccg acgatcgcga tgggatcgtc gtcggcgggg   1080
cgggcgacgg cgggcaccgg cgccgtctcc tcggcgcgtt cgccgaggag ttcgccagc    1140 aggtggccgg ccagggagcg cgggttgggg tggtcgaaca cgagggtcgc gggcaggcgc   1200
agcccggtgg cggcggacag ccggttgcgg agttcgacgg cggtcagcga gtcgaagccc   1260
agttccttga acgcccggcc ggggggtcacg gcggtgtcgt cggtgtggcc gaggaccacg   1320
gcggcgtgcg agcggacgag cgtgagcagg gtccgttcgc gttccgcggc ggtgagtccg   1380
gtgagctttc cggccagggt gtccggtccg gcgcccgcgg tggcggcgcg ccggacgggg   1440
ccacggacca gccggcgcat cagcgcgggt acgcggtga cgccggtggc gaacgaggtg    1500
aggtccagcc aggcggggac gacgacgggg gcggagccgg cggtggcgcg gtcgaacagg   1560
gcgagcgcgt cgggcgtcgg cagcggcacc acgccgtcgc gggccgcgcg ccgcaggtcg   1620
gcgccgccca ggtggccggt catgccgctg gcgtgcgccc acaggcccca cacctgggag   1680
gtggcgggca ggccctgggc gcggcggtgt ccgcgagcg cgtccacgaa ggcgttgccc    1740
gccgcgtagt tgccctgtcc gggcgccccg aagaggccgg aggtggagga gaacagcacg   1800 aagacgccg gccggtgcgg ggcggtgagt tcgtgcaggt tccaggcggc gtcgaccttg    1860
gggcggagca ccttggcgag ccgctcgggg gtctgggagg cgatgacgcc gtcgtccagg   1920 acgccgcgg cgtggacgac tccggtcagg gggtgctcgg cggtgatccg gtcgagcagg    1980
gcggccagtt cggtgcggtc ggcggcgtcg caggcggcga cggtcacctc ggcgccgagg   2040
gcgcgcagtt cgccggcgag ggtcacggcg tcggggccg cgtcgccgcg ccgtccggcc    2100
aggaccagcc ggcgtacgcc gtgctcggtg accaggtggc gggcgcagag ggcgccgagc   2160
gtgccggtgc cgccggtgac gaggacgacg ccgtcggacg ccacagggc cgcctggctc    2220 gtgggctcgt cggtgcgcgg ggcgcggacc agccggggtg cgaggacccg gccggagcgc   2280
acggcgatct cgggttcgcc ggtggcgagg acagcgggca gctgttgcag tgcgtcgggg   2340
ccgtcgatgt cgaccagcac cagcctgccg gggtgttcgg cgcgggcgga gcggatcagg   2400
ccccacacgg gcgcgtgggc gaggtcggtg acgtcctcgt gctcgaccgg gaccgcgccg   2460
tgggtgagga cggccagacg ggtgccggcc agtcgctcgt cggcgagcca ctcctgaaga   2520
gcggtcagca cgcgccgggc gccggcgtgg gccgcgccgg cggtgtcgtc ggccgactgc   2580
tgccgacacg gcagcacgag ggtgccgggc acggtgtcca gggcggcgac ggcggcgagg   2640
tcggggcagg agggtatcc gggcagcgga aggccgccga gcacggcgat gccgtcgacg    2700
tcggccgcgg gcagcggcac gggcgtccac tcgacccggt acagctcgtg gtcgcggccg   2760
```

```
gggccggccg tggccggcgg gcgcagggtc accgcgtcga cggtgagcac ggcggctccg    2820
ctgtcgtcgg tggcgtgcag ggtgaccgtg tgctcgcccg cggggtgcag gcgtacccgc    2880
agccgggtgg cgcccacggc gtgcaggtg acgccgtgcc aggcgccggg gaccaggccg     2940
gggtgtacgg ccgcgagggc gtcggtgagc agggcgggt gtacgcccca gccgccggcg    3000
gtctcgtcgg tcagctcaac ggtcacgtcg gtcagctcga cggtcacgtc ggtgtccggg    3060
tcccctggcg cggcggccgg ggcggtgccg gtgtgcggga ggaggacgcc ggtcgcgtgc    3120
cgggtccagg gctggtcgtc gtcggcgtcg gcggggcggg agtggacggc gaccgggcgg    3180
gcgccgtcct cgttctccgc gcccaggtg acctggaggc ggcgggcttc gccgacggtg    3240
tcgagcggtg cctcctcggt cagttcgccg agcgtcctgc cgtcggccgc gtgcagggcc    3300
aggtcgagta cggcgccggc cggcagctcg gtgccggccg gcacgcgccc ggtgaacacc    3360
tgtccgccgg atccggcgag cggggtgacg gcgccgagca gcggtgccc ggcgccggtc     3420 aggcccaggc cggcggcgtc ggaggcgacc gggccgctgg gccagaagcg gcggcgctgg    3480
aaggcgtagg tgggcaggtc gacgtggcgt ccgtcggggc agcccaccgt ccagtcgacg    3540
gacacgccgt ggacggcggc ctcggcgagc gaggtgagga ggcggcgcgg gccgtcctcg    3600
tcgcggcgga gggtgccgac gacgacgcg gtccgctcgg tggcctccgc cgtctcctgc     3660
acggcggccg tcagcaccgg gtgcgggctg atctccacga acacggcgtg gccggagtcg    3720
agcaggccgc gcaccacggg ctcgaaccgt acgggctccc gcaggttgcg gtaccagtag    3780
ccggcgtcga gccgtgtctc gccgagggg ccgcccagca gggtggagtg gaaggcgatg     3840
ccggcctcac cgggccgcag ttcggcgagc gcggcgcgca actcggcttc gagggactcg    3900
acatgggccg agtgggaggc gtagtcgacc gcgatgcggc gcagtcgtac cccgtcggcc    3960
gaccaggcgg ccatcaccct cgtccagcgca tcggggtcgc cgctgaggac caccgacgac    4020
gggccgttga gggcggcgac gcaaacgcgt ccggaccacg gtgcgagccg ccgtgtgacg    4080
gtggcctcgg gcagggcgac ggagaccatg ccgccgcgcc cggccagccg ctcggcgatg    4140
agccgcgacc gcagggcgac gatccgggcg ccgtccgcca gcgacagcac acccgccaca    4200
caagcagccg cgatctcccc ctgcgaatga ccgaccacag ccgacggcac gacaccgtac    4260
gaacgccaca cctccgccaa cgacaccatc accgcccaca acaccggctg aacgacatcc    4320
acccgctcca acgccaccgg atcacccagc acaccacgca acgaccagcc cacgaacggc    4380
tccaacgcca ccgcacactc agccatccgc cccgcgaaca ccggcgacga atccagcaga    4440
tccaccgcca tccccaccca ctgcgccccc tgacccggga acacgaacac cacccggccc    4500
tcacccggca acccggcaac acccgacacc acaccctcca ccggctcccc cgcggccaac    4560
gccgccagag aagcccgcgc accggccaca tcagcggcca ccaccaccgc acgatgcggc    4620
aacaacgccc gcgacgcggc aagggaccag gagaggtcca ccgggtccag gccgggtgg     4680 gtgtcgaggt gggcggcgag ccgggtggcc tgctcggcga gggcggcctg ggagcgggcg    4740
gagagcagcc acggcaccca gcgcggcgcg gcgccgcgcg cgggcgcggc cggttccgcc    4800
ggggcctcct ccaggatgag gtgggcgttg gtgccgctgg cgccgaacga cgacacgccc    4860
gcgcggcgcg gccggtcgtc gggggccag acggcggcgc cggtgacgag ttcgacggag    4920
ccggaggccc agtcgatgtg cggtgagggg gcgtccacgt gcagggtgcg gggcacttcg     4980
ccggcgcgca gcgcgagcac cgtcttgatc acgccggcca cgcccgccgc ggggccggtg    5040
tggccgatgt tggacttcag cgagcccagc cgcagcggct gtgcgcggtc ctggccgtag    5100
gtggccagca gggcgttggc ctcgatgggg tcgccgaggg tggtgccggt gccgtgtgcc    5160
```

-continued

```
tccacgacgt cgacgtcggc ggcggtgagg ccggcggcgg ccagcgcgga gcggatgacc    5220
cgctgctggg cggagccgtt gggggcggtg agcccggagg aggcgccgtc ctggttgatc    5280
gccgagccgc ggaccacggc cagcacgggg tggccgttgc ggcgggcgtc ggacagccgc    5340
tccagcacga ccacgcccgc gccctcggac cagccgatgc cgtccgcggc ggcggcgaac    5400
gccttgcagc ggccgtcggg ggcgaggccg cgctgccggg agaactccac gaaggcacgc    5460
ggggtcgaca tgaccatcac gccgccgcg agggccagcg agcattcgcc gctgcgcagg    5520
gactggccgg ccaggtgcag ggcgacgagc gaggacgagc aggcggtgtc cacgctgacg    5580
gccgggcctt ccaggccgag ggtgtaggcc accggccgg agagcacgct ggcgtagttc    5640
ccggtgccga gcagcccctc gtccacgccg gcgaccgcgc cgtgccgtga gtcgtagcgc    5700
tggtcggtga cgcccgcgaa gacgccggtg gcgctgccgc gcaggccgtg cggatcgacg    5760
ccggcgtgct cgaacgcctc ccaggcgact tcgaggaaca gccgctgctg cgggtccatc    5820
gccagcgcct cgcgcgggct gatgccgaag aagtcggcgt cgaagccggc ggcgtcgttc    5880
aggaagccgc cctggcgcag gtaggtgtgt ccggcccggt ccgggtcggg gtcgtagagg    5940
ccgtcgaggt cccagccgcg gtcggcgggg aagtcgccga tgacgtcacg gccttcggcg    6000
aggagctgcc acaggtcgtc gggcgaggcc actccgccgg ggaagcggca ggccatgccg    6060
accacggcca gcggctcgtc ggccggggtg gcgcggacgg cggggcgggc cgggacgggc    6120
gcgccgtcga gccgggtgag cagatggtcg gtgagggcgg ccgggttcgg gtggtcgaag    6180
acgacgctgc tggccagcgt caggccggtc gcctcggtca gcgcggtgcg cagccgcagg    6240
gaggcgaggg agtcgaagcc gagggcggcg aaaccgcggt gcggttcgat cgcggcgggg    6300
tcggcgtggc cgagcacggc ggcggtccgc agccgtacca ggtccatgac gcggtgccgg    6360
cgttcggcgg gggtcagccc ggccagctcg tcgcgccagg gcgtgccctc gtcggcggtc    6420
cgctgcgcgg ggagcgcgac gggggtggcg gccggggggca gcgggcgggc cgctgcgtcc    6480
acgggcggcc agtaccggtc gcgctggaag gcgtacgtcg gcaggtcggc cgggtgggct    6540
ccggtgcccc ggaagaaggc ggtccagtcg atgcgcacgc cgtgcgtgtg cgcctcggcc    6600
aggttggtca gcagggtcgg caggccggcc cggtcgcgct ggagggtgcc gacgaccgcg    6660
gctccggtct ccgtgcgctc gacggtctcc tgggtgccga cggtcagtac ggggtgcgga    6720
ctgacctcga tgaagcccg gtggccctgg gcgagcaggg cggcgacggc gtcggcgtag    6780
cggacgggtt cgcgcaggtt gcggtaccag tagccggcgt ccagcgccgt gccgtccgcc    6840
cactcccccg tcacggtgga gaacagcgga accgtgccct cacccggccg cacgccctcc    6900
agatcagcca gcagagcctc acgcaccggc tccaccagca ccgaatgcga ggcatagtcg    6960
acagcgatac gccgggcccg cacccccga ccccgcaat gagccaggaa ctcctccagc    7020
gccaccccct cacccgcgac gacgaccgac tcaggaccgt tgaccgcagc caccgccaac    7080
cggcccgccc agcccaccaa cagctcctcg acaccgacg gccgcagc gaccgacacc    7140 atccccccac tgcccgccag cgccgtcaaa gccctgctgc gcagggcgac gacccgggcg    7200
ccgtccgcca gcgacaacac acccgccaca caagcagccg cgatctcccc ctgcgaatga    7260
ccgaccacag ccgacggcac gacaccgtac gaacgccaca cctccgccaa cgacaccatc    7320
accgcccaca acaccggctg aacgacatcc acccgctcca acgccaccgg atcacccagc    7380
acaccacgca acgaccagcc cacgaacggc tccaacgcca ccgcacactc agccatccgc    7440
cccgcgaaca ccggcgacga atccagcaga tccaccgcca tccccaccca ctgcgccccc    7500
```

```
tgacccggga acacgaagac ggcgcggccg tcgccgacgg cgcggccgcg caccacgtcg    7560
gccgactcgg cgccttccgc cacggcggtc aggccggcga gcagggtgtc gtggtccgcg    7620
ccgaggacga ccacgcggtg ttcgaaggcc gtacgggtgg tggcgagggc gagggccacg    7680 tcgtggggggg cggcgtcgtg cgcgggccgg tgggcgagga ggcgttcggc ctgggcgcgc    7740
agtccggccg ccgtccggga ggacagcgtc cacgggacga ccggcagggt gcggtccgtg    7800
gcctcgtcgg tgggctcggg ccgggcgggt gcctgctcca ggatggcgtg ggcgttggtg    7860
ccggacacgc cgaacgacga cacgcccgcg cggcgcggct gctccccgcc cggccagtcc    7920
cgctcctcgg tgagcagttc cacggcgccg cggtccagt cgacgtgcgg tgacgcctcg    7980
tccacgtgga gcgtgcgcgg cagcgtgccg tggcgcatgg cctgcaccat cttgatcaca    8040
ccggccacac cggcggcggc ctgcgtgtgc ccgatgttgg acttcaccga accgagccac    8100
agcggctcgt cccgctcctg gccgtaggtg gcgaggaggg cctgcgcctc gatcgggtcg    8160
cccagccggg tgcccgtacc gtgcgcctcc acgcgtcga cctggctcgc ggccaggcgg    8220
gcgtcggcca gcgcctggcg gatcacgcgc tgctgggcga gtccgttggg ggcggtgagt    8280
ccgctgctcg cgccgtcctg gttgatggcg gtgccgcgga ccacggccag cacggggtgg    8340
ccgttgcggc gggcgtccga gagccgttcc aggacgagca tgcccgcgcc ctcggcgaag    8400
ccgaacccgt cggccgccgc ggcgaacgcc ttgcagcggc cgtcggccgc gagggcccgc    8460
tgccggctgt actcggtgaa cacgccgggc gtggacagca cggtcgcccc gccggtgagc    8520
gccagcgtgc actccccggc gcgcagcgag cggaccgcga ggtgcagggc gaccagggac    8580
gaggagcagg cggtgtccac ggagagggcg gggccctcca ggccgagggt gtaggcgacc    8640
cggccggaga gcacgctggg cgaggtgccg gtgacgacgt accctccag ctcggtggcc    8700 accgggccgg tgatgtcgga gtagtcctcg ctgctgaagc cgacgaacac gccggtggcg    8760
gtggagcgca ggccggccgg gtcgatgcca gcccgctcca gggcctccca tgaggtctcc    8820
agcaccagcc gctgctgcgg gtccatggcc agcgcctcgc gcgggctgat gccgaagaag    8880
ccggcgtcga agtccgcggc gccgtcgagg aatccgcctt cgcgggcgta ggaggttccg    8940
ggccggtcgg ggtccgggtc gtagaccgag gccatgtccc agccgcggtc ggcggggaac    9000
gccgagaccg cgtcggtccc atcggtcacc agccgccaca ggtcctcggg cgaggtcacg    9060
ccgccggggt agcggcaggc catgcccacg atcgcgatcg gttcgcggtc gcgggcctcg    9120
gcctcgcgca gccggcgccg ggcgacctgg agatcgcccg tgacctgctt gaggtagtcg    9180
agcagtttgg cctcgtcagc catcggtgca ccccgtgcg gttcgttcgg cgcgggtcac    9240
gagacgcccc ggtcgatcag gtcgaagagt tcgtcggcgg tgacgccgtc cagagcggcc    9300
cgctcgggtg tgccgtcggt cgtgccggcg tcccagcggg ccgcgaggtc ccgcaggtgc    9360
gccgccaccc gggcgcggtc ggtgccgtcg gccggcagtg cgccgagcgc gctctccacg    9420
cgggccagtt cggcgatgat ccggtcggcg ctcgcctcgc cggactcgct cggcaggagc    9480
gcgtcgagga ggtggtcggc gagcgcggcc gggttcgggt ggtcgaacac gatggtggtg    9540
ggcagtcgca ggccggtggc ggtgccgagg cggttgcgca gttccacggc ggtcagcgag    9600
tcgaagccca gttccttgaa gccgcggtcg ggtgccaccg cgtcgcgtcc ccggtgtccc    9660
aggacgtcgg cgacctggcc gcggacgacg tcgagcaggg cggggggcgcg ctcggcgcg    9720 ggcagcccgg tgatccgcgc caccagggcc gccgcaccgg gcaccgggcg ggcggcggcc    9780 gggcggccg ggtggcgac caggccgcgc agcagcggcg gggtgggcgc ggcggaggcg    9840
gtggcgaggt ccaggcgcgc ggtgacggtc acggcgtcgc cggtggcggt ggccgtgtcg    9900
```

-continued

```
aacagggcca gtccttcggc ggcggccatc ggcacgatgc ggttgcggcc ggcgcgggcg      9960
acgtcggcgg cgtccaggtg ccgggtgagg ccggtggcgt cggcccacag gccccaggcc     10020
gcggcggtgc cgggcaggcc ggcggcgcgg cgccgttcgg cgagcgcgtc gaggaaggcg     10080
ttggcggcgg cgtagttggc ctgcgcgggg gtgccgaggg tggccgccgc ggaggagaac     10140
agcacgaagg cggacaggtc cttgtcctcg gtgagttcgt gcaggtgcca ggcggcgtcg     10200
gccttcgggc gcagtacgcc cggcagccgg ccggcgccga gttcggtcag cacgccgtcg     10260
tcgagggcgc ccgcggtgtg caccaccgcg gtcagcgggg cctcggcggt cagcttggcg     10320
agcagcgcgt cgagggcggc gcggtcggtg acgtcgcagg tctcgaagcg gacggtggcg     10380
cccgccgcgg ccagttcggc gaccaggtcc gcgctgccgg gggcggcggc gccgcgccgg     10440
ctggccagca ccaggtcacg ggcgccgtgt tcggacacca gatgccgggc gagcatgccg     10500
ccgagcacgc cggcgccggt gatcaggacg gtgccgtcgg cgtacggggc gacggtgagc     10560
acgatcttgc cggtgtgccg ggcctgggcc atgaaccgga acgcggtgcg cgcgtcggcg     10620
aggggccagg tccgggtggg cagcccggtc agctcgcccg cctcggcgtg ggcgacgacc     10680
tcggtcagca ggctctggac gcggtcgggg ccggcgtcca gcagcaggtc gaacgggagg     10740
tagtcgacac cgggcaggcc ggcggggtcg cggcggtcgg tcttgccgag ttccacgaac     10800
cgtccgccgg gacggagcag tcgcagcgac gcgtccacga actcaccccgt gagggagttc     10860
agcacgacgt ccatctccgg gaaccgctgc gcgaactccg tatcccgcga cgacgccaca     10920
cgcgcctcgt ccagaccggc cgcccgcagc acctcgtgct tgccgggact cgccgtcgca     10980
tacacctcgg cgcccagcag ccgcgccacc cgcaccgcgg ccatgcccac caccaccggcc     11040
gccgcgtgca ccagcacccg ctcccccgcc cgcaccccgg ccacatcgcg cagcgcgaac     11100
caggcggtgg cgaacacgga cggcagggcc gcggcgcgga cccaggacca gccggcggga     11160
acgggcacca cgagccgccg gtccaccacg gcgagggtgc cgaagccgcc cggcaccatg     11220
ccgaggactc ggtcgccgac ggcgaggtcg gtgacgtccg gggcgaccgc gaccacggtg     11280
cccgcggcct cggagccgat cgcgtcgacc tcgtccgggt acatgtcgag cgcgcacagc     11340
acgtcgcgga agttcaggcc cgccgcgcgg acggcgatgc ggacctggcc gggtgccagg     11400
ggggcggtgg cgtcgggagc ggcgacggcg tcgacgccgt cgatgctgcc gggccggacc     11460
acgtcgacgc gccaggcgtc ggcgccgacg ggcgggcgca gcgcggtctc agcggcccgg     11520
gtgagccggg cgacgaggcg ttcgccgtcg cggagcgcgg tctgcggctc gtcgccgacg     11580
gccggcacag cgtccaggga ggcgggtgtg ccgtcggtgt cgacgagcag gaaccggtcg     11640
gggtgctcgg tctgcgcgga gcgcaccagg ccccagaccg cggcggcggc cgggtcgggt     11700
tcctcgccgg gccgggcggc gacggcgtgc cgggtgacga tcgcgagccg ggcctgcccg     11760
aaccggtcgt cggcgagcca ctcgtgcagc agttccagca cctgggcggt ggcccggtgg     11820
gcggcggcga ccacatcggc tcctgtgctg acggagcgga ggacgaggtc caccgcgccg     11880
gcgtcgatgt cggcgagggc ggtgctcagg ggcgcggcga ggccttccgg tccgtcgccc     11940
aggacgcgc agcgcgcggc ggcgggtgtc tcggcgtcgg gggtctgcca ggtcacgcgg     12000
aacagcgcgt cgcgcgtgcc ggcggcggcc acggcgcgga gctgcccggc cgacgcgggc     12060
cgcagccgca gcgcggccag ctccacgacg ggccggccct cgcggtcggt cgcggtgagg     12120
ctcagcgtgt cggcgctctc ccgggcgcg cgcacccgca ggaccgggc cgggccgggg       12180
tgcacggtca cgccggtcca ggtgaacggc agcagcagcg gcgcgtcctc gggctcggcg     12240
```

```
gcgggcacgg cctgggtgac ggcgtcgagc agcgccgggt gcacgagatg gccggcggtg   12300
tcgacggtgt cggggagttc gacctcggcg tagacctcgg tgtcccggcg ccacagggcg   12360
cgcaggccct ggaaggcggg cccgtagccg tagccgcggg cggcgaaacg gtcgtacacg   12420
ccgtccaccg ggaccggctc agcgcccgcc gggggccacg cgccggtctc gggctccgcc   12480
ggctcggccg gctcggccgg tgccaggacg cccgtggcgt gccgggtcca gccgtcgccg   12540
gagtgggagt ggacggcgac cgtgcggcgg ccggacccgt cggcgccgtg cacggtgacg   12600
cgcagggtca ggccgtcggc ggggacgccg atgggcgcgg ccagggtcag ctcctcgatc   12660
tgggcgcggt cgagccggtg gccggcgtgg gccaccatct ccaggacggc ggtgccgggc   12720
agcagggcgg tgcccagcac ggtgtgctcg gtcagccagg ggtgcgtctc ggggctgatc   12780
cggccggtga ggagcaggcc gtcctcgtcg gggagttcgg cctcggcggc gagcagcgga   12840
tgccctccgg cggtgaggcc gacggcggtc aggtcgccgg cggcggcctg gggggtgagc   12900
cagtagcgct cgcgctggaa ggggtaggcg ggcagttcga ccgggcgggc gccggtggcg   12960
tcgaacaggg ggcgccagtc gaccggcacg ccgtcggcgg ccacctcggc cagtgcggtg   13020
gtcaggcgca gccggtcgct ctcgtcgcgg cgcagggtgg cggcgacccg cagttcggtg   13080
cccgccgcct cggcggtctg ctgcatggcg accgtgagca cggggtgcgg gctgatctcc   13140
acgaagccgt ggtggccggc ggcgagcaga tcgctgatcg cgttctggaa gagcacgggc   13200
tcgcgcaggt tgcggtacca gtagcgggcg cccagttcgc tgccgtcgat ccagtcggcg   13260
gtgacggtgg agtagagggg cacgtcgccg tcccgggggc ggatgcccct gaggtcggcg   13320
agcagccgct gccgtacggc ctccacctgc ggggagtgcg aggcgtagtc ggcggcgacg   13380
cggccggcgc gcagcccctc gtcgtcgcag aggtcgagca gctcctccag ggcatcgcgg   13440
tcgcccgcga cgaccagcga gcgggggctg ttggcagcgg cgatgccgag ccggccgggc   13500
cagcgctcca gcatccgctc gacgttcgcc gcggggcgg cgacgaaggc catgccgcag   13560
cggccgggca ggtcggcgac ggccttggcg cgcagcgcga cggtcttcgc ggcgtcgtcc   13620
agggtgaggg cgccggcgac gcaggcggcg gcgatctcgc cctgggagtg gccgaccacg   13680
gccgccggca cgacgccgtg ggagcgccac accgcgccca gcgagaccat gagcgcgaac   13740
agcaccggct gcaccacgtc gacgcggctg agcggcggcg cgtcctcggc tccgcgcagc   13800
acgtccacga ccgaccagtc caggtagggg gcgagggcgc gctcgcactc ggccatgcgc   13860
gcggcgaaca ccgggtgggt gtcgagcagt tccacgccca tgccgagcca ctgtccgccc   13920
tggccggcga agacgaagac gacgctgccg tcggctccgg cggtgccgcg gacgacggcc   13980
gggtcggcgc cgcccgcggc gagcacgtcg agcgcggcga gcagttcggc gcggtccgg   14040 cccacgacgg cggcgcggtg ctcgaacgcg gtgcggcggg tggccagggt gaacccgacg   14100
gaggcgggct cgaggccggg gtcggcggcg acgaactcgc gcagcgggc ggcctgttcg   14160 agcagcgcgg cctcggtgcg cgcggacagc tgccagggca cggggagcgc accggccggc   14220
ggcgccgtcg cttcctcggg ttcgggcgcc tccgccacga tcacatgggc gttggtgccg   14280
ctgacgccga acgaggacac gccggcccgg cggggacgct cgccccgggg ccacgggcgg   14340
gcctcggtca gcagccgtac gtcgccggac acccagtcca cgtgcgggt gggctcgtcg   14400 acgtgcagcg tcttcgggag cagtccgtgc cggagcgcga gcaccgtctt gatcactccg   14460
ccgacgccgc cggcggcctg ggcgtggccg aggttggact tcagcgagcc cagccacagc   14520
ggccggtcgc ggtcctggcc gtaggaggag aggagtgcct gggcctcgat ggggtcgccc   14580
agggcggtgc cggtgccgtg gccctccacg gcgtccacgt cggcgggacg cagtccggcg   14640
```

-continued

```
tcggccagtg cctgccggac cacgcgctgc tgggcggcgc cgctcggcgc ggtgaggccg   14700
ttggaggcgc cgtcctggtt gacggcggtg ccgggcagca gggcgagcac cgggtggccg   14760
tttcgccggg cgtcggagag ccgctccagc aggagcatgc cgacgccctc ggaccagccg   14820
agtccgtcgg cggccttggc gtacgagcgg cagcgaccgt cctcggacag gccgccctgc   14880
ttggtgaagt cgacgaacag ctccggcgtc ggcatgacgg tcacaccgcc ggccagcgcg   14940
agggtgctct cgcccgagcg cagcgaccgc accgcctggt gcagggcgac gagggaggac   15000
gagcaggcgg tgtccaccgt gaaggcgggg ccttccaggc cgaggacgta ggagatgcgg   15060
ccggccacca cgctggccag gcggccggtc agggcgtgcc cgtcgccgcc ttccgggatg   15120
ccggcgagca gcgaggagta ggactgggcg ttggcgccga cgaacacgcc gacgcgtccg   15180
ccccgccacg agccgggtgc gacgccggcc cgctccagcg cctcccagct ggtctccagc   15240
agcagccgct gctgggggtc catcagctgg gcctcgcgcg ggctgatgcc gaagaagccg   15300
gcgtcgaaca gggcgacgtc gtcgaggaat ccgccgtgcc gggtgcggct ggccgagggg   15360
ccgtccgggt cggcgagggc ggcgaggtcc cagccgcggt cggcggggaa cggcgtgatg   15420
gcgtcgcgct cctccagcac gagccgccac agctcgtcgg gggtggtcac accgcccggg   15480
aagcggcagg ccatgccgac cacggcgacc gggtcgtcgt cggccgcgcg ctgtacgggc   15540
tcgtcgtcct cggcgagccg gacgtgccgg ccggaggcgg cgtcgaccag gacgtccgcc   15600
agggcgcggg cggtggggtg gtcgtagatg gcggtggtgg gcagcttcac gccggtgccg   15660
cggctgagcc gcagcagcag ttgtacggcg gtcagcgagc gcagtccgag ttcccggatc   15720
gcccggtccg gcggtacgtc ggcggcggtg ccgaggtcga gcacctccgc gacctgtgtc   15780
cggaccaggt ccaggacgac gcgccggcgc tcgggttcgg gcagaccggc gagccggtgc   15840
gcgagcgcgg gcggctgagc agccttcggg tcggtcagcg gctcagtcat gggtggtccc   15900
ctccagcggg tccggtgcgt gcagtgcgga gacgggcagg ccgggttcgg cgagtgcggc   15960
ctgtagcagc gcggcggtgc cggccagcag gccgtccacg acgcgtcggc cgagggcggc   16020
ggcgcggtgt acgacgtgtc cggtgaggcc gccgtcgggg tcctcgacca ggtgcacctc   16080
gaggtgccag cgggcgtacg cctgttggcc cgtgaactgc tcgacgcggg cgccaggcag   16140
gccgagttcg ccgagttcga cgttgacgag ctggaacacg acgtcgacca gcggctgttc   16200
ggggtccagg ccgaggcctt cgacgacgcg ttcccagggc agggcctggt gggcgtaggc   16260
gtcgagggcg gtgtcccgga cccgctccag caggccggcg aaggacgggt cgccgctgag   16320
gtcgacgcgc aggggcacga agttggcgaa gaagccgatc agcccctcga cctcggcccg   16380
ggtgcggccc gccaccgggg agccgacggc gaggtcgtcc gtgcccgccc agcgggcgag   16440
cgtgccgtg aacgcggcca gcagggtcat gtagagggtg gcgtcgtgct cggcgccgac   16500
ccggcgggcg gtggcgacca ggccggcggg cagccgccac tcggtcagca cgccggtggc   16560
gtcgtgggcc gcgtcggccg ggacgcccgg cagggcgagg ggccgcaggc cgtccagccg   16620
gcggcgccag tggccgagct gggcgtcgag cgcggctccg gtcagccagg accgctgcca   16680
gaaggcgaag tcgccgtact ggacgggcag ttcgggcagc tcggccggac ggttctctcg   16740
tagtgccgcg taggcgccgg acagttcggt ccagagcacg ccctgggacc agccgtcggt   16800
ggcgatgtgg tgcaccgtca gcagcaggac gtggtcgtcg ggggcgatcc gcagcagtgc   16860
gggccgcagc accggtcccc ggacgaggtc gaacggccgg gccgctgcct cgtcggccag   16920
ggcgcgggcg gcggtctcgt cggccacgtc caccgggtcc agcacgatgt ccgtggcggg   16980
```

```
caggatcacc gacgccggct cgtcgccggg cacgaagacc gtgcgcagcg cctcgtgccg   17040
gcgcacgacc tcggtcaggg cgcggcccag caggtccgcg tccagttcgc cggtgatccg   17100
cacggccagc gggatcgtcc agaccgggtc gccggggtcg gcctcgtgca gccgccacag   17160
ccgcagctgg cccagcgaca gcggcagggg ctcctgccgg acaccggca ccaggggcgg    17220 tacggccgtg cgcggggcca cggcgacgac ctcggcgagg gcgcgcgggg tgcggtgctg   17280
gaacagctcc gcagggaca cctcggcgcc cagcgcctcg cggatccggg cgaccgtgcg    17340
ggccgcgacc agcgagtgcc cgccgagcgc gaagaagtcg tcgtcgatgc cgaccccgcc   17400
ggtctccagc acctcggcga acacctcgca cagcgtctgc tccgcaccgg tacggggtgc   17460
ggtgaagccg gtgtcgagcg tggtgcgcag gtccggggcg ggcagcgcgg cccggtcgat   17520
cttgccggtg gtggtcagcg ggaacgcgtc cagcgcgacg agcgccgacg gcaccatgta   17580
gtccggtacg gcgtcggcca ggtgggcgcg cagccggggcc ggcagccctc cgtcggtacc   17640
ggggacgggc acgacgtagc cgacgagccg cttgacgccg ggggcgtcct cgcgggcgac   17700
gatgacggcg cgggtgacct cggggtggcg cagcaggacg gcctcgacct cgcccagctc   17760
cacccggaag ccccggatct tgacctggtg gtcgagccgg cccaggtatt ccaggctgcc   17820
gtcgggccgc cagcggccca ggtccccggt gcggtagagg cggagccgg gcgggccgaa    17880 cgggtcgggc acgaacttct gcgccgtcag ttccggcttg ccgacgtagc gcgggcgag   17940 tccggggccg gcgaagcaga gttgccggc cacgcccacg gggaccggcc gcagccggtc    18000
gtccaggacg taggcgcggg agttgtcgac cggctcgccc aggtgtgcgg tccggggcca   18060
gtcggcgacg tcagcgggca gggtgaagga ggtgacgacc tggatctcgg tggagccgta   18120
gtggttgtgc agacgcagac ggggccgggc ggcgcagaac tcgcgcagca cggtgtccag   18180
cgacagcggc tcgcccgcct gggagatgtg ccgcagcgag gtgagccggg cccggccggc   18240
gccggcctcc tcggcgagcg cgcggatcat caggttgggc acgaatatct gctcgacggc   18300
ccgttcgtcg agccagcggg cgaagcgggc cgggtcgcgg cgggtctcct cggtggggat   18360
gaccagcgtc tcgccgtaca ggagcgcgga gagcacctcc tgcacatgca cgtcgaaggt   18420
gagggcggtg aactgggcgg tgcgcgtgcc gggtccgccc ggtaccgtct tcttctgcca   18480
ggcgagcatg ttgaccacac accgggcggg catggcgatg cccttgggca cgccggtgga   18540
gccgagggtg tagacgacgt aggcgaggga gtcggggccg ggtcgtccgg cggccgttgc   18600
cgcgggcggc tcctgcccgg ccggggcgtc cacgaggacg agggcggtgc cctcggcgaa   18660
gacgtccgcg tgagcccggt cggtgacggc gacggtcatc cgggcgtcgt cgacgatgag   18720
ccggatccgg tcccgggggt ggctcgggtc gatcggcaca taggcggcgc cggccttgag   18780
gatgccgatc agagcggcca tctgcacggt gccgcgctcc aggcagaggc cgacgaggtc   18840
gtccggcccc acgccctggg cccgcagccc ggcggcgatc cgctcggcct cgtggtccag   18900
cgcggcgtag gtgaggacgt cgtcctcgca ctccacggcg cgggcgcgg gggtgcgggc    18960 gacctgctcg gcgaacagct ccacgagcgg gacgtcccgg tacgggaggg cggtgtcgtt   19020
ccaccgctcc agcagcaggc gccggtcgtc gtcgtccagc agcgagagcg cggacagcgg   19080
cgcgtccggg tcggcgaggg cggcgcgcag cagcaccgtg tggtgatgca gcaggcggcg   19140
gaccgtgtcc gcctcgaaca gcgcggtgga gtgcagcacg gtgccgcgca cccggtcgcc   19200
gtcctcggtg aggtgcactt cgaggtcgac gcgggtgaag gcgtgctcgt ccagcagcgg   19260
ttccaggcgg gcgcgccga ggcggtcgcc cttgtccccg ggcgcccgca tcagctgaa     19320 gaccacctgg accagcgggt tgcgggacag gtcccgctcg ggtgccaggg tctccaccag   19380
```

```
gtgctcgaag ggcaggtcct ggtggtccat ggcgcccacc accgtctcgc gcacccggcc    19440
cagcaggtcg cggaaggtcg ggtcgccgga gacgtcggtg cgcagcacca gcatgttgac    19500
gaagaagccg atcagccgct ccacctcggg gcgggtacgg cctgccacgg gggcgccgac    19560
ggcgacgtcc tcggtgccgg cgaaccgtgc caggaccacg gtgaaggcgg tcagcagcgt    19620
catgtagagg gtggcgccct cggtgtcgcc gaacgcgcgc gcggcccgga ccaggtcctc    19680
gggcagttcc cacggctggg aggcgcccgc cgagccggcg accgcggggc ggggccggtc    19740
caggggaagt tccagggggc gcagcccggc gagccgcgcc cgccagtagg tgaggtaccg    19800
ctccagttcg gcgccggtga gccggccctg ctgccagacg gcgaagtcgc cgtactggac    19860
aggcagttcg ggcagttcgg cggggtcgcc ggacagttcg gcgcggtagg cctcggccag    19920
ctcgccccag aacacggcgt gcgaccagcc gtccgtgacc gcgtggtgcg cggtgatcag    19980
gacggcgtgg tcctcggccg cgaggcgcag cacgcgggcg cgcagcagcg gtccccgggc    20040
caggtcgaag gggcgcgcgg cgtccgcctc ggccagggcg cgtacctcgg cctcgtcggc    20100
gacgtccgtg acctccaggc ggagcggggt cgcgggccgt acgacggcca taggctcgcc    20160
ggcgtcggcg gcgaagacgg tgcgcagcgc ctcgtggcgg gagaccacca gggacagtgc    20220
ccggccgagg gcgtcgacgt cgagcgggcc gtgggcgcgt acgcccatcg ccacgttcca    20280
gaagccgctg tccggggtga gccggtccag gaaccacagg cgccgctggg aggacgacag    20340
cggaagcgcg gcgccgtccc ggcgggccgg ccggatgacg tccgtggccg tgccgggctc    20400
gccgagggtc tcggccagcc ggcgcgggga gcgccgttcg aacaccgcct ggagcggcac    20460
gtcgggcccg aagcgggcgc ggatccgggc gatggcgcgg gtggccagca gcgagtgccc    20520
gcccagggcg aagaagtcgt cgtcggcgcc caccgggtgg acgtccagca cctcggcgaa    20580
gatctcgcac agcacccgct ccgcctcggt cgcgggcggg acgtaccgc tctcggcgac    20640 cgagcgggtg tcgggcgcgg gcagggcccg gcggtcgatc ttgccggtgg tggacagcgg    20700
gaacgcgtcg agcgcgacga acgccgacgg caccatgtag tcgggtacgg agcccgcggc    20760
gtgggcgcgc agggcgggca gcacgctcgc gccggcctcc ggctccagca ccacataggc    20820
gaccaggcgc ttgtcgcccg ggatgtcctc gcgcacggcg acggtgacct gcgagaccgc    20880
cgggtgccgc agcagcgcgg cctcgacctc gccgggctcc acccggaagc gcgggatctt    20940
gacctggacg tcgcgcggc cgaggaactc cagcgcgccg ccgggcagcc accgtacgac    21000
gtcgcccgta cggtacatcc gctcgcccgg cccgccccac gggtccggca cgaacttctc    21060
ggcggtcagt cgggccggc ccaggtagcc gcgcgccacc cggggcccgc cgatgaccag    21120
ttcgcccgcc acgccagcg gcgccgggcg gagggtgtcg tcgaggacgt acacccgggt    21180
gttgtcgatc ggcgcgccga tgggcacccg ggagccggcg agccggaagc cgggttccat    21240
cgggaacagc gtggtgaacg cggtcgcctc ggtcgggccg taggcgtcgg ccacggtcag    21300
gtgcgggtgg gcgccatca cctgggcgac ggtctcgccg acacggcct cgccgccggt    21360 gagcacctcg cgcagcccgc cgaagcactc catgcactcc tcggccagga ggctgaacag    21420
gggtgcgggc aggcacatcg cggtgacgcc gtgctcgcgg atgagccggt cgaaggtgtg    21480
cggttcgacg tgctcgtcgg tggcgacgac gatctgcttg ccggtcagca ggaacggcca    21540
cagctcgtag gtggagatgt cggtggccag cggatagtgc agcagcaccc gttcgtggtt    21600
gccgttgctc cagcggcggt cggcggccag cacgacgacg ttgcggtggg tcacggccac    21660
gcccttgggc tcgccgctgg accggaggt gtagatgacg tacgccgtgg tgtcggggtg    21720
```

```
cgggtcgata ccggggtcgg tgtcgggccc ggggcccggg tcggtgacgt cgaggacggt   21780
gatgccgtcg gtgccgggca ccgggcggtc ggcgatgacg acgcgcagcc ccgaggtggc   21840
cacgatgcgc tcggtgcggc ccgggggggtt cgcgggtcg agcggcacgt aggcggcgcc   21900
cgccttgagc acgccgagca cggcggccac catgccggtg gagcgtccgg tggcgacgcc   21960
gaccggttcg tcggcgccga cgccgtgggc cagcaggagg tgggcgaagc ggttggcccg   22020
ccggtccagt tcggcgtagg tgacccgctc gtcgccgcag atcagggcga cggcgtcggg   22080
ggtgcgggcg gcctgctcgg cgtagagccg gggcacgcag ccgtccggca gcggtgcggc   22140
cgtgtcgttc caggcgacca gggtgcggtg ccggtcggtc tcgtcgagca tggtcgccgc   22200
ggagaccggc cggtcggggt cggcgagcac ctcgccgagg accaccgaca cgtggtgcat   22260
cagctggcgg acggtgtcgg cgtcgaacag gtcggccgcg tacaggacgg tcgcgccgac   22320
ctcgtcgccg gtctcgacgg cgtgcacctc caggtccatc cgggtgtacg cgtggtcgat   22380
gtcgaacggc tcggcccggg cgccctgcca ccagggccgc cggggcgcgt cggcgagcag   22440
ctggaacgcc acctgcacga gcggttgcg ggacaggtcg cgctcgggc gcagccgttc   22500 caccaggtgc tcgaagggga cgtcctggtg ctcgacggcg ccgaccaccg actcccgtac   22560
ccggcccagg agttcccgga aggtcgggtc gccggacagg tcggtgcgga cggcgacgac   22620
gttgacgaag aagccgatca gcgcctcggt tcggcgcgg gtccggccgg ccgtcggcga   22680
gcccacggcg atgtcctcgg tgcgggcgta ccggacagg acgagggtga acgcggccag   22740
gagcaccatg tagagcgtgg ctccctcgcg ggcggcgacg gcccgggcgt cccggatcag   22800
ctcggcgggc agctgccagg gcaggtgcc cgcccgcccg gtggcgacgg cgggccgggc   22860
cttgtccagc ggcagttcca gcggggcgag gccggccagc cggccggtcc agtagccggc   22920
ccggcgctcc agcacctcgc cggtcagcca ggaccgctgc catacggcgt ggtcgccgta   22980
ctggacgggc agttcgggca gcggggcgcc gtcgtacgcg gcggcgatct cggcccacag   23040
cagggcctgg gaccagccgt cggtcgcgat gtggtgcacg gcgacgacga ggacgtggtc   23100 gtcggggcg agccggagca gcgtggcgcg cagcagcggg ccccgcgtca ggtcgaaccc   23160
ggtggacagc tcggcggagg ccgcggcgcg tgccgcgtcg gcgtcgggta cgtcgacgat   23220
ccgcggggcg accggggcgg cggcgccgat gaccgcggcg ggcacgccgt cggcgaccgt   23280
gaaggtggtg cgcagggtct cgtgccgggc gacgaccgcc gacagggcgc cggccagccg   23340
ctcggggtcc agcggtccgc gcacgcgcag ggctccgccg gaggtgtacg aggcgctgcc   23400
gggggcgagc tggtccagga accacatccg ctgctgggcg aaggacacg gcagcagccg   23460 gtcgcggtcc gcgggcacca gcggcggcgc cgggtcggcc gggagcgcgg cgccggcgac   23520
caccgaggcc agggctcgcg gggtgcggtc ctcgaacacc tcgcgcagcg ggacctcggt   23580
gccgaaggcg cgggcgattc gggcgacgag gcgggtggcg agcagcgagt ggccgccgcg   23640
tacgaagaag tcgtcctcgg cgccgaacgc gtcggcgtcg agcagctcgg cgaagatctc   23700
gcacagcgcc cgctcggcgt cggtgcgcgg ggcgccagg ccggcgtccg ccgtctccgc   23760
cggggcgggc agcgcggcgc ggtcgaccct gccggtggcg gtcagcggca gcgcgtcggc   23820
gaggacgaag gccgagggca ccaggtagtc gggcagggcc gccgcggcgt gggcgcgcag   23880
ggcggcggtg tcggtggtgc ggccggcgcg cgggacgacg tgggcgacga gccgcttgcc   23940
ggccgggccg tcaccgcgca ccacgacggc ggcgtgcgcg acggcggggt gggcggccag   24000
gacggcctcg acctcgccgg gctcgacccg gaggccgcgc agcttcgcct ggtcgtcggc   24060
gcggccgagg aactccagga cgccgtcggg gcggcggcgc accacgtcgc cggtgcggta   24120
```

```
catgcggctg cccgccggtc cggacgggtc gggcaggaag cgctcggcgg tggccgccgg    24180
ccggccggcg tagccgcggg ccaggcgcgg ccgccgacg  tacagttcgc cgggcacgcc    24240
gaacgggacg ggccgcagcc ggtcgtcgag gacgtgggcg cgggtgttgt ccagggggct    24300
gccgatgggc acccggccgc cggggcccgg gtcggccggc gcgatcgggt ggagggtggc    24360
gaaggtggtg gtctcggtgg ggccgtagcc gttgacgacc gtcaggtccg ggtgggcgcc    24420
gcgcacgcgg gccacggtcg ccggggacac ggtgtcgccg ccgacgacga gttcgcggac    24480
gccggccagg caggtgacgt cctcctcgac cacgaggtcg aagaggccgg aggtcagcca    24540
cagcgcggtg acgccctggt cggcgacgac acgggcgagg gcggcgggtc cgagggcgcc    24600
gggcggggcc accacgacgc ggcggccgga cagcagcggg gaccacagtt cgtaggtgga    24660
ggcgtcgaac gcctgcgggg agtgcagcag gacccgttcg tgggcgccgc cggaccagcg    24720
ccggtggagg gcgagggcgg ccacggcgcg gtgggtcgtg gcgacggcct tgggcgtgcc    24780
ggtggaaccg gaggtggaca tcacgtacgc gaggccgtcc gggccgacgg tgttcggcaa    24840
agccgtgtcg ggggctgtgc cggggacggc gcgcaggtct acggccggca ggtgctcggt    24900
gccggcgggt gcgggaccgc cgtcggtcag cagcagcgcg gcaccggtgt cggcgaggac    24960
ggcgcgggtc cggcggccg  ggttgcgggc gtcgagcggc aggtaggcgc cgccggcctt    25020
gaggaccgcg agcacggcga cgaccaggtg ggcggaacgt tccgtcgcca gcgcgacgac    25080
gctctcgggt ccggctccgt ggccggccag gacatgggcg agccggttgg cggcgcggtc    25140
cagctgggcg taggtgaggt gttccgtccc gtcggccacg gcgacggcgt ccggggtgcg    25200
ggcggcctgg gcggcgaaca gctcgggcag cgaggcctcg ggcagcggta cgccggtgcc    25260
ccgggcggcc cggtccaggg ccgcgtcctc gcccgcgtcg gtcatcgtca gccgggacag    25320
cggccggtcg ggctcggcgc aggcggcgcg cagcagggcc gtcaggtggc gggccagccg    25380
ctcgacggtc tcccggtcga acagggcgcg gctgtagttg atcagtccct cgacgccgcc    25440
ctcggcgtcc tcgccgaggt agacctccag gtccatgcgg gtgaaggcgc ggtcgcccgc    25500
gaagggttcg gcggtggtgc cggggaacgg cgcggggcgc gcggcggcc  ggggcacgta    25560 ctggaagacg acctgggcga gcgggttgcg ggacaggtcg cgctcgggga ccagccgctc    25620
caccaggtac tcgaacggca cgtcctggtg cgccatctcg tccaccgagg cggcgcggac    25680
gcgttcgacg agttccgcga aggtgggtc  gccgccgagg tcggtgcggg tgacgacggt    25740
gttgacgaag aatccgatga gttgctcgac ctcggccagg ggccggccgg cgaccggctg    25800
ggcgacggcg acgtcctcgg tgcggcgtg  ccgcccgagg accgcgctga acgcggccag    25860
cagggtcatg tgcagggtcg cgccctgccg tgcggcgacg gcccggggcgg cggcgacggc    25920 gtccgccgga agccgccagg tgacgacgcc gccctcggcg gaggcgacgg ccgggcgggg    25980
ccggtcgagc ggcaggtcca gcgggggcag gccggccagc cggtcctgcc agtacgccag    26040
ccgccgctcc agcacggcgg gcgacagggt acgcgctgc  caggcggcga agtcggcgta    26100
ctgcaccggc agttccggca gcgcgggctg ccggccgtcg gccagggcgg tgtaggccgc    26160
ggtcagctcg gcccacagca ggccgtgcga ccagccgtcg gtggcgatgt gatgcaccgt    26220
cagcagcagg acgtggtcgt cgtcggcgag ccgcagcagg cgggcgcgga gcaggggcc     26280 cttggtgagg tcgaaggggc gcgcggcctc ctcgccggcc agccgctcgg cgtcggcctc    26340
gtccacggcg tcggtcacgg gaacgggcac cggctccggc ggcaggacga cggcgccggc    26400
cacgccctcg tggtcggcga agacggtgcg cagggtctcg tgccgggcga cgacacagct    26460
```

```
cagcgcccgg gccagcaggc cggcgccgag cgggccgcgg acgcgcacgg cggtgccgaa    26520
gttgtagaag gcgctgtccg gcatcagccg gtcgaggaac cacagccgct gctgggcgaa    26580
cgacagctcc agcggccggt cgcggggggac ccggctgatg cccgcgggtg tcgtgccggt   26640
cctcgccgtg cgctcccgga gccggttgag tgccgagtcc agtcccggcc gtcgcgagct    26700
cccctgcgtc atccggctgt ctcccgctcc tcgtcggctt cggtgagtcc gcggtcgcgc    26760
atcacgctgg ccagggcgcg gtgggtgccg gactcgcttg cttcgaactg ctcgaccacg    26820
cgccgccgca tcggggcggg cttctcctgg ctgagcttga acatcgtctg cacggaatcg    26880
acccgcaggg tgaaggcgcc cacgccgggc gcgatctggc ggaagtagtc gagggaggac    26940
tcctggtccc agccgcgccc gaagccggac tccagccgcc gggcggtgtc ggagacgatg    27000
tccagcacgg cggcggggtc ggcggtgggc tccactgtgc cgttcacgtg gacggcgatg    27060
aagtcccagg tggggccgc gggcgtgacc ccgtagaccg tcggcgagac atagccgtgc     27120
gggccctgga agacgatgag cgcccggtcg ccggagcgca tccggcgcca ctgcgggttc    27180
tcgacgttca tgtggccgat cagggtggag ccggcgagcg ggacggtgcc cgcggcgacg    27240
gcctcggcgt cggcgccgtc gggtccgtgc cggaacagca ccggcgcgtg ggtggccacc    27300
gggacgtcgt cgtgcgaggt gacgaccatt gccagtgggt tgtgtcgcag aaacgccagg    27360
acgacgccgt cgcaatcctc ccggtacagc ggacgttcgt acacttcagc ccctgttccc    27420
cgctgctgcc ttgcttccgg tggagcggtc cgggtcgcac cggccgccgg tgatcgaccg    27480
ggcgatctcg cccgcgcgga ccgccaccat ggacagcagg gtggaggcga tgccgtgggt    27540
cgcctcggtg gcgccctgga cgtagatgcc gcaccggaaa tccccggtgg tgccgagccg    27600
gtagtcgcgg ccgatcagca actcccccgc ctcgtcccgg cggagggcgc cggagacgcc    27660
gccgagcagt tcgccgggt cggtggagtc gtacccggtg gcgtacacga ccaggtcggc     27720
gtccaggtcg gtgtgttcgc ccgtgggcag gaactccacg cgtacggcgg cggattcctg    27780
gcgcggttcg acggacacca ggcgggaggc gttcatcacc cgcagccgcg gggcgccgga    27840
caccttctgc tcgtactggc ggcggtagag gccctggagg acgtcctcgt cgacgacggc    27900
gtagttggtg ccgccgtggt agcgcatgat ggcctgcttg acctcgggcg gggcgaagta    27960
gaagtcgtcc acggcggccg ggtcgaagac gcggttggcg aacgggctgg agtcggcgac    28020
gctgtagccg tagcgggcga acaccgcgca cacctcggcc tgcgggtagc ggtccatgag    28080
gtgcgcggcg acctcggccg cgctctggcc ggcgccgacc acgacggccc ggcggggcgg    28140
gcgttcgtcg aacgcgggca gccggtgcag caactgggag ctgtgccaga cgcgttcgcc    28200
ggtctccgcg ccctcgggca gccgggggcg caggccggag gcgaggacga ggtttctggt    28260
ccgggcgacc acccggtccc cggcgagcac gtcgagcgcg acgacctcac cggcttcggt    28320
caccggccgc acaccggtgg cctccacgcc gtactcgacc aggtggttca gccggtcggc    28380
ggcccactgg aggtagtcgt ggtactcgat ccgggagggc agcagggtgt gctggttgat    28440
gaagtcgacc agccggtcct tctcctggag ataggacagg aatccgaaat cactggtggg    28500
attgcgcatc gtggcgatgt ccttgagaaa ggacacctgg agcgaggagc cccccaggag    28560 catccccga tgccagccga attccttctg cttctccagg aaaagggcct tcccggcggc     28620
ttcggattca tggagcgcca ccgccagggc gagattcgcg gcaccgaatc cgattccggt    28680
gacgtccagt acttctgatt ccgggctctg ctgcgcagtg gatgattgct ctgcgagccg    28740
ggtcatatat caaccgccat tagttttca atggatgtat cgtcgcagga cgcccagaat     28800
tcacctgcga cgtcctccag atgcgtgagg gaacgcgcgc tgtaaaaggt ggtctggtac    28860
```

```
tgggttatgt cgtagtcgac gtgggccatg tcggcgatgt ccagcggccg gatctccgcg    28920
gaacggaagt gctccagctc gccgtaggag gagacgacgc tggcgccgta ggcccggggc    28980
ccgtcggcgg cgtccagcag gccgcattcg agcgtgaacc agaaggtctt ggcgacgaac    29040
tggacggcgt cctcggactc caccctgcgc acggcctcgc cggccaggcg gtacaggttg    29100
gcgaaccggt cgtcggccag ggcgctgccg tgcccgatga cctcgtgcag gatgtccggt    29160
tccgtcgagt agaagggtgt cgcgctgtcg cggaggtact gggtggagtg gaagtacccg    29220
tcggccagag agccgcagaa cagggcgaag ggaaccacgc cggacgcggg gcgtaggcgg    29280
aatccggtca gctggtcgag ccggtcggac acttcacgca actgcgggac gccgtcgccg    29340
cccacctcga gccgctccgc cgcctcgacg aactccggcg ccgccatgtg ccggtgccgg    29400
tccgcgagcc gcttggaaac caggcgccac agagcgtgct cggcgtccgt gtactcgacc    29460
tctggaatgg gctcgccggg cacataggcg gcagcgcttg cggcgatttg gtcacgccgc    29520
tgctgataca ccgacgacgc ggttaattcg ggcgcgccg agccgatttc cacgaacttc    29580
cccctacttc catcgacaga aggcagcagt tgctgtccga agctattttg gttcggacgc    29640
ccgcatcaac cttcccttgt ccagccgatt cattaggacc ctacaagcca cccgcagcac    29700
tcgcaagagt tttctatgcg cccgctatgt acccttttgg gcagactcac cggaaattat    29760
cgtcatccgc accgccggaa ccggagtcaa gcgttggctc ggcagggcgg cttcaagttc    29820
ccgataggag cgggccctag gcgattcctc agatccggcc ggcgcgttcg ggtgtgtccc    29880
aaatcactgg cctaaatcct tcatgaggac ccgtcagctt gccgacggac gctctttcgc    29940
ttgtggtgcc gggcgtttcg gtgtccgggc aggccgcgcg ggagcgcccc aactgccgcg    30000
tcgggctgtc gcgtcgggtg ggcgccgggt tccacggctc cggagtcct tcgacagggc    30060 ccggcgaata tctccaggac caagccgtgg gcggtgaggt ggtcggcgag ggcggtgagt    30120
tcggcggcgt tgcgaccgag ccgcttccgc tcgtacaccg tgaagatgac acggcagtgt    30180
ggggcgtgcg ccttgacctc ccgcgccgcc ctcagcgcct cctcccggaa cttcgggctg    30240
ccccgcgccc gggtgctgat cttctcgccg aagatgtagt cgcgcgagat gccgtgtttg    30300
gcgagcgcgt cgagctggga gtcacttcgc ctgcatccgc ccgcgcgcgg agtggtgcgg    30360
catcgtggca gcgcgcgtca gatgcgcggc gtcgccccca ggtgaactcc gtccgccctg    30420
gggcagggtg ggcggagttc accgcgtcgt gcggttcaac gggtccaatg gaggtcgcga    30480
tacggtccgc ccggcgcgcg ggccgcgatc atcattccgg cggggcggag ccgtcagtgc    30540
ttgacggtga acgtggcgcc ttggggcgcg aaggtcgtgt cgtggtcctt ggcggtggcc    30600
agcacggata cgtgccagac gcccttgggc aacgcggcgg cttccttggc cgagctcttc    30660
acggtgtagg tgcacaccga ggccgtcgcg gaagtcgcct tgcacgtggc ttcctcgaca    30720
tcccgcatct cgcccgccgt gggcgcaagg cccgaactcg ccggccaggc gagcacccgc    30780
aggctcttga ttccggagtt gtcggccacg gtggcgctga aggtgagcga ggcgctccca    30840
ccggccgtac tggtgtagtg ggcggtggcc tttgagatct ccggcttggc cggcacagcg    30900
gcgtcggccg aggagacgaa caccacggtg ccggcaacga cggctgcggc cacggcgagc    30960
gacgagacga caaggcgctt ggacatgaag tatcccctca tagatgaccg ctactggtct    31020
cttcgccgag cgctctgcgc accgcggcgt tgtgtacaca gcctgtctcg acggccctgc    31080
ccctcacatg ggcagaacta ctcaaccgaa gtactcagac gccctgagct tgtcgttcaa    31140
cctcgtctcc gttggggcg ggtattgagc aggcgctttt cgaatgtggc gtccagcacc    31200
```

```
gccgtccagg atgtgcagcc ggtctgcaag cttcgtcgcg atcaggacct tcagcagatc    31260
cagcgcgtcg tccaccgccc gcgacgtgag gtacaccgcc gcggccagca gcgttgtgag    31320
gctgcgagag tccgagtgcc ggcgcggcaa cgacaccttg tcgtccgccc cgtaccgcga    31380
ccactctgcg ccgccccgtc acccgtaccg gtccgcggcg cagccggtcc agctccacca    31440
ggcggcccga cgagcagaga atccagcacc gcccgctgca cgacgcgcgg catcccgcac    31500
aaggcgtccc aaaacgccga ttcgccgcct cccacaccga tcccacagga caggccggac    31560
agctcgcccc cagcagcagc ggctactgtc acccgttcgg cggcgggcgc gacagagccc    31620
gtgacaacca gattgtgacg ttcggtgatc gtgacaccaa ttcggagctg gcccgctgac    31680
ctgtgacagc ggactggcct cgaaggtgga ccgaatgcag ttcttgacag caaagacgga    31740
ccgccgcagc tcaggggcgc agtgcccgcc cgcagcacag tcggttcagg gctcgacgcc    31800
ggctacggac agacgtggat cgccggtcgc ggtcagcgcg aacgctgtcc ggtgaagagg    31860
cggtacagca ggagcacgat caccgagccg acgaccgcgg cgatccatgt cgagaggtgg    31920
aagaagccgt tgatggagtg cacgccgaag atcaccttgc cgagccagcc gccgagcaga    31980
ccgccgacga tgccgatgag catcgtgacg aggcagccgc ccgggtcctt gccgggcatg    32040
agtgccttgg cgatggcgcc cgcgatgagg ccgatgagaa tccaggcgat gatgcccacg    32100
gtgtgcgtcc tttgctgtag gtggtgccga ggaaggcccg acgaggctcc gccggggctg    32160
cccgccggtc gctccgcgcg gacgaccggc gacatacgga tatccgctcc ggaacactcc    32220
acacgggtca aggtcccgt ttcctccgac cgacccaccc ggcatccgat ccgtcggccg    32280
atccggtcga cggcggattc ggtgactggt caaccttcga tggcgctcga tcaaggttcg    32340
ctgtcacagg tcatccgccc tcagtccctc aggtcgcccc tcggaaggcg tccaccagag    32400
gtcaggcggg tccattcctc cggatcccca gctgcctcac agggtgctgg ggacccgggg    32460
acggccctcg gtgttatgga taagccgaag ctcaggacgt tctcacggcg acgccggatg    32520
agctggcgag gagggcgtgc cgaggcagtt cggttgtcac cgaggaggca tcccacttct    32580
cacgcgtgct cattcggcgg acttcctgtc accggcgccg acgagccgga gttcccgggc    32640
tccccggctg ggcccggctg agggctgagc ccttccacgg cgaggcggaa gaggcggtcg    32700
gcctgggtgt cggggtctgt gtggtgctcg gtggccaggg cgatgccgac ggcgagggtc    32760
agcaggtcgt gaaaggtgac gtgcggtgca accgccttgt cgcggatggc ccgctggagc    32820
aagggagttg cggctgcttc gattacgccc ccgcagctct tcggggaggg ttcttcggtg    32880
ggcggctcgt agctgaggat atgggcgaat ccgcgggctg agacggcgta gcggacgaag    32940
gcgtggaacc actccagcag tgcggtgcgg ccgtcctcgg acgcactcag ccgatgggcg    33000
cgctcgcaca ggccccgcaat gcgctcctgg aagacggctt cgaggagcgc ccggcgggtg    33060
gggaagtgac ggcgcacggt cgccgaaccg acgcctgcga tgcgggcgat ctgctcctgg    33120
gatgcctcgg cgccgtgcgc ggcgacttcg gcttcggcga cggcgaggat gcgctgatag    33180
ttgcgtcggg cgtccgagcg ctggccagtc atggtctcct cgttgctaag tggcgggccc    33240
cgccatatct tagcggcaca cgaaacggcg ggcccgccg ttttgtctct ccggcccttg    33300
aggagcagca ccatgcccag cagcagcgat accgtcctgg tcaccggcgc caccggccag    33360
caaggcgggg ccacggctcg cgcgcttttg gccgccaagg tgcccgtacg tgcgctcgta    33420
cgcgatccct cgtcgaagtc cgcccgggcg atcgaggcgc tgggcgcgga actggtacgc    33480
gcggatcttt ccgaccgggc ctccctcgac ccggcggtcg aggggggtccg cgcggtgttc    33540 tcggtgcaga tgccgcccat gaccgagacc agcgtggact tcgcgagcga actcgcccag    33600
```

```
gccaccaacc tggtggacgc ggcgaagata gggggagtac ggcagttcgt acagtcctcg   33660
accagtggag tcgtgaaca cacccgggtc gccggctggg ccgagggccg ctgggcggcg   33720
atggcggagt acttccacac caagcaggcg atcatggagg cggtgcgtgg tgcgggtttc   33780
gcccgctgga cggtgatcaa gcccgccttc ttcatggaga acctgcccct gctggcaccc   33840
aaggggcccc gcggcggact gctgacggta ctgaagccgg acaccgaact ggccttggtg   33900
gccgtgcggg acatcggcac ggccgcggca cacgccctcc gagaccccga ccggttccac   33960
caggtggaac tggaactggc tggtgacctt cgcacgatgg agcagatcgc gcagaccttg   34020
tccgccgcct gggcgtgcc cgtgaccgcg ccctccctga gcgtggaaga ggcccttgcc   34080
gcgggcatgc cgaagtgggg agccggacac gagtggaaca cgtggtcct ccagcccgcc   34140 cggcccacat tcgcccggaa gttgggcatc ccgctcacca ccttcgccga gtgggcggat   34200
gagcagttga cacatgtgtc tgattagggg tgtggcggca agggcgcgcc attgacccct   34260
acggggagcg cggcggttgc ccgcagaggg cattgcggtc gggggcatc ggtgccggtc   34320 ccctggacgg gctgcaatga gcaggacagc gcagaggggt ggacacgaga tccctggagt   34380
gcacgacgtg gccatcaggg ggtcgggcgg tacgggatgg ggatgatgta gcgcgggtgt   34440
ggaggcatcg gcccagtgcg ctgcttccgc tgttcgcgcg ggtgccggca gcctgttcgt   34500
tggagtcgtc gtggcttcgg agcccgtccg ggaagtacac gccgtgggcg ctggcccatg   34560
ctgcccgggt gtcgctcgcg tgggggaacg agtaccgcaa ggacgcgggc gatgcggctt   34620
cggcggcctc cctcgggtcc tcgccctctt cctcgtcgct ctcgttccag tcgagagcgc   34680
ggccgggtcc cgcccatccg cacgagcaca ccgcgcgcaa cgctgccgcc cgcggtccgc   34740
catgaggccg gccgtcgtag acgctccgct ccgatagcca cctggcctcc gctccggaag   34800
agctgaggaa gagcacagga tccggacgg tgccatcggc cagcaacacc ccgaccgcac   34860
ccacgtggga cgaccgaac tcctccgtcg tccacgtctc cctctcacct tcacccatcg   34920
tctcgcccct ctcctcatcg ccgcatccgc accggccga acgcacggat acagacgatt   34980
ccggagtcca aggttccgca cagcgagatc ctcgaaaagg tgacctcgca cctccaccgt   35040
gcaccaggcc tcaaagccca cgacgagccg accgagcgca gaccaccgaa gacgaagcgc   35100
atcgccgctt cccagtgcgc tggttgatga ggttcaggaa agcggggtca cttctctaca   35160
tcggacagct accgcagctt gccgcgcccg ccgcccggag cggcggttgc tcggcgcccg   35220
cgtgcgggtc ggaagcggag gctcggccgg cgaggttcgc cgtcgatgcc ggcggcacga   35280
cgggccagct ctccgatctt ctcctcgggc agtccggaca tcctgacggc ctggcgcact   35340
gcggcccggc agtcgggccg tgagcagtgc gccgacgata ccggccgtcc gaccgtcgga   35400
tgctcgggcg gcaggtagat cgctgcgcag ccgacgcaca gatagattga tcgcaaggcg   35460
cttccccttc gtcagctgag gccgctgccg tggcaggtat tgcaggagcc ggtccagcta   35520
cgggcgacgg gcttctggtt cccgtcctta tcgacttcga cagagtgctc ggtgtgctca   35580
gtgactccgg atccgctgca agcggagcaa ggcacgtcag acatttccc aggatgcccg   35640 attctgtggg gccgtgtcag tcgtcccgcg acactcgcgc gctaccggac cgggcgggcc   35700
catcccgaga atctcccgcc tgcatcacgg cggcgccaac ggcgagcccg aacctctggg   35760
ccacgcggtc gctcgccggc ccggtgggcg acctcgtgcc gccacgttcc cactgcgcgc   35820
tgttccgcca ctccccgcc ccccaggcg agtcctcgct gcgctcgcag tactgccgca   35880
cgagcaggtc gcccgctccc ggagaggccc cagcatcacg gcccgtcaag gtgctccgga   35940
```

```
tcggtggtgg ccgttgtgaa ccgccacgcg ccgcccggct cgtcggcctg gccatcgccc    36000
ggcctggtcc cgctcaggat gccggggcgg tcaggacggc cttggcagcc agccggaaat    36060
tcctgatcat cggattcggg tcgcccttgc ggctgaccag gacgacccgg ctgggggag     36120 cgccctcgac cgggacggtg acgaggtcgg gacgcagtga gctgcgccga tcgccgaccg    36180
gtagcacggc gatggccctg ccgctcgcga cgagttcgag cttgtcctcg tagctctcga    36240
tcggcggcac gccggtcccg aggaactggt aggaagccca gcctgcggtc tcgaacgcac    36300
acggcgccgc ctcttcgccg gccagttctt ccgcggtcac cgacgcgcgg tcggccagag    36360
gatggccgcg cgggaccacg agcatcccggg gctcctcgta cagcggggtg gtgaacacgt   36420
cgtcggcgac gagcggcagc ggggcccgcg cgatcagggc gtcgacgcgc ctgtcggaca    36480
gtgccccgac gtcgcggcag tgcagatgcc gggtggcgat ctcggcgtcg ggtaacggc     36540 ggcgcagttc ccgcacggcg gcagtgatca ccaggtcttc gacgtagccg atggcgattc    36600
gttcggtccg ggcttgttca cgcacggcca gctcggcctg cgggcggcc cgcagcaggg     36660 cctgggcccg ggggaggaac gtccggccgg ccggagtgag ccgggtgccc tgggggtgc     36720 ggtccagcag tcgtgtgccg agatatttct cgagccgttg gatctgacgg ctcagcgccg    36780
gctgggctac gtgcaggtcg gcggcggccc ggccgaagtg ctggtgcgcc gccaccacgg    36840
tgaagtagcg caccagccgc agttccaggt cctgcccgag atcgttcacc ctcgcagggt    36900
acgcgtcatg ccgtttcgga atggtcagat tgccgaaccg gtcttggacg gccatgccgt    36960
cccgggcttt gactgaagga gcaacgtttc cccgagaaag cgacaggcgc gatgaaggcg    37020
atccagatcc acgaagcggg tgggccggaa gttctgcggt acgacgaggt gccggctccc    37080
gagatcggcc cgggcgaggt gctcgtccgg gtgcacgcgg cgggcatcaa cccgccggac    37140
tggtacctgc gtgaagggat gaaggtcatg ccggccggga tgaggccggc gctggagttc    37200
cctctgatcc ccggaacgga catgtcgggc gtggtccagg cggtcgctcc ggacgtgccg    37260
gggttcggcg tcgcgacga ggtcttcggc atgctgcggt tccccggatt cgacggccgg     37320
acgtacgccc agtacgtggc cgcgccggct tctgacctgg ctcacaagcc ggccggtatc    37380
gaccacgtgc aggcggccgg ggcgccgatg gccgtgctca cggcctggca gtacctggtc    37440
gacctcggcc acgaggtgcc gtctcctttc accggccagg tgcaccagcc ggtgccgatc    37500
acgccgggga tgaccgtgct ggtcaacggg gccgccggtg gagtgggcca tttcgcggtg    37560
caattggcga aatggaaggg ggcacacgtc atcgcggtgg cctcaagtcg gcacgagcgg    37620
ttcctgcgcg agctcggtgc cgatgagttc atcgactaca ccacgacgca ggcccgcgac    37680
gtggtcagcg gtgtcgacct ggtgatcgac accgtcggcg gccggacgg ctcacgcttc     37740 ctgaccgtac tcaagcgcgg cggcaccctg ctcccggtgt tcttcgccga gtacgacccg    37800
gaagagacgg cgagtctgga catcaccgtc tcgaacattc aggtacgttc ccacggcccc    37860
cagctcgccg agatcgggcg cctgttcgac gagggcacac tccgggtcgg ggtggacagc    37920
acctacccgc tgtccgaagc ggtcagcgca cacacgcgag ccgcgcaggg ccacatccaa    37980
ggcaagatcg tgctgacggt ggcctcgtga tcgccgaaac tccagcaggc ggtggcgaac    38040
tacgcccacg ccttggacga gttgcatata cccgagctgg aaacggtcct ggccgaagac    38100
accacctgga ccgtcacgat gccggacag gggatgctcg gccccgtcgc cggacgcgcg     38160
gccgcggcgg tgctcgactt catcttcatc cccgtgtca gctcggtgag cggtgtccca     38220
gaccggcccg gaacctcagc agttgcccag ccgacccgat gagcgcgggc gccgagttgc    38280
ccgcgagcag ccgcggcgcc atcttgacgg gcaggcccag tcgcgctgcc gcgtcggatt    38340
```

```
cacgccggtt tcctcgggtc gctgtcggcc aagtcagcgg tcattgtgcc acccgtccca   38400
cttcggaaga cgctgaccgc cgctcccccg atcctggatg cggcggcttt cacggcacgc   38460
tgctccgctg ccgtgccgac gaggtctccg gacggctgag ccgtgctgcg catgccgcgc   38520
cgcctcggcg accgatcgcc gcgcagcgtc agatgcgccg gactttcgcc acggcaaggg   38580
cgtccgcgac ctcccggacg acacgcttcg cgtcgtcggg gctgttcacc acgtcggtgc   38640
ggttcatgtc gatcacgagg acatcgctgg cggaatagtg ctcgtgcacc cagtcgtcgt   38700
acccggccca aagcgtccgg tagtactcga cgagactttg gtcctgctcg aagtcacgcc   38760
cccgcagtcc gatgcggcgc agcaccgtct cgaagtccgc tctgagatac accatgagat   38820
cgggtgcctt gcgatagggc aggccgtcga tctcacgcat catctccgcg agcaacccct   38880
cgtacacctg catctccagg gaactgatcc tgccgaggtc gtgattgact ttggcgaagt   38940
accagtcctc gtagatcgac cggtcgagga cgttgtcgtc ctgtttgtac gcctccttga   39000
tcgcggcgaa tcgcgtctgc aagaagtaga gctggagaag gaaggatag cgcttcgccg    39060 ctatctcctc aggaccggcg gtgtagaaga gcggcaggat cgggttgtcc tccacgctct   39120
cgtagaagac catgctcccc agctctttgg cgatcagctc ggccacgctt gtcttcccga   39180
tcccgatcat gccgccgacg cagatcactg ccatacctcg cttctttccc gggacaccgt   39240
ccgcgggcgc gattcccgcg caccggctct tccacggcac acgcaccgcc gcggagcgca   39300
gtcgtggaag cgccccaggc gcaggtgacg agcctggcct ccgtcggacg accgaagcgg   39360
catcatatcg gcacggaggg gtgttcgaat ctacgtgctc gtgccctgga tggaagacgc   39420
tggtgcaccg ggtagcggga tcatcggagg tgatcatgta gcggtgggc ggaacgacgc    39480 ggaacgacgg agtggtggga caggggccac tgacgcacgt atccgcagcc gcgctggagt   39540
cgccgacctc cacaggttca ctctcaccgg tgaccaagga aagatcgccc gcatgccagg   39600
ctcgcccgct cctccccgga acagcgcgta caccgatcag gagaacgacg ccgcgacccc   39660
gagcgagcag ccgagcctgt gtggacgccg aacgtgtcgg ttaccactcg acgaccagcc   39720
ttgacacacc gcgcgtcgcg aggccctccc gccatacgag ggcctcgtcc cccggtgcga   39780
gtcgcaggcc ggggaagcgc tgccacaagc gggtcagcgc gatcttcatc tggagaagaa   39840
ccagtggcgc gcccatgcac cggtgggcgc cgtgtccgaa tgtgaggtgt gcaggccggc   39900
gggcgctgct cttcgcaccc gatgtgcaaa atacttcggc gtcatgattg ccgtgcagca   39960
acgagacgat gacggcctct ccttggcgca ccgtcgtccc gcccaggaca aggtcctcga   40020
tggccactcg gggaaaactg ataggtgtgg acggcgtctt gcggagcagc tcctcaacca   40080
gatcctccac ggattgcccg tcgagcgcgt caccggtgag cagttcgagt atggcaaggc   40140
tcaattgatg ggcggtggtc tcgtaaccgg ccatgagaag tgccagtccg aggttgatca   40200
actcgatgcg ggatatctca cccgactgct caacccgcac cagcgcgctc aggagatcct   40260
gcccgggcgc atccctcttt ctttcgatca gtgaggacat gtacttgata agagtcagga   40320
tatggcggcc tcttctgcgg gttccctgag gcgtcatgtc gaacagcgca gtcacggcgg   40380
cgtcgaaaac gggccgctcc gccgccggca cgccgagcag tgagctcaac gcgaccatgg   40440
gaaggggcga agcataaccg ctgaccaggt cggcgcctgg ccccgcaacc tgtagccgat   40500
ccagcagtgc gtcggcggcc tcctcgatca ccgctgcctg tgcggtgact cgggcgctgg   40560
tgaacgctgc tccggcgacc cggcgcagcc gggcgtggtc cgcaccgtcc agactcatga   40620
tcgagttggg tgagaggtcg acggatcccc atttcggagc atcggggtgg gtggccgcag   40680
```

```
ctctgctgag acgtgtgtcg gcgagcgcgg cgcgccccac ggcgtagtcg gtgaccagcc   40740
acatgtgatc accagtgggc atccgcaccc gtttgacggc ctcacttgat ggcgctgcca   40800
ggaagggcgg caggggggccg accctgtggt gatcgaaagt gccggacatg gtcgattact   40860
cctgttcggt cggaaacgcc gcggggtgtc tgtctcccct gccgccgacg gccgtgggag   40920
acgacccatc gggtggcggc cgggtcgggc gagcgggctt tttccaccgc ccggaaggcg   40980
gcccgctgtt cggtctgcac gctgttcggg ctgcccggct tcggcggaca gaccggcttt   41040
ggcggacaga ccggctgccg gatgttcgtc acgtagcgcg cacggtgtgt tccctgcctc   41100
tcagcgcatc ccgccgtcgc ggcctgacgc gttggacgcc tgtggtctca gccgagcgtg   41160
ggcaccgaac tgcgtcggcc cgtcgacctg cgctctgcgg gacaggacga ggtcccggag   41220
tcgctgtggc agggcgtcgt caaagcggag gtggtccggc accgtgacgc cggcgttgcg   41280
cagcggcgtc gcgatctcgc ggcaggtggt gctgagccag ttgaggaccg cgggatctcc   41340
cgagcggccc gcgaccggcg tccaggtggc cacttccggc tgccggaggc cggcgtcgag   41400
gaacgtccgg gtgaggcggg ggccgaagtc ggggacggcc ccggccgcca ggaagggcc   41460 gggccacagc gcgtagtact cgtcccactc cggcagcggc ggacgtgacg gcgacgtgtt   41520
ggtgaagtcc atctcgtgca tgacgacgat cccgtccggt ttcagcaggg acgtcagacg   41580
gcgcagtgcg gatgcgggat cgggcaggta catcaggatg tacctgccga ccaggacgtc   41640
gaacttcatc ggccaggtga agtcggccag gtccgcggct tcgtaccgca ccgagtccgc   41700
gagccccgcc tcctgtgcca ggatccgcgc cttgtggacg gttccggggt cgcgctcgat   41760
tcccacgacg tgtccgccgg gcccgaccag ttgggcggcc agcagagaga cgtatcccag   41820
tccggcaccg atgtcgagga cgctcatccc cggacgtact ccggccgacc gcagggtgcg   41880
ttcggtgaac ggcgagatcg cctcgttctg aagggtcagc cttggtgct cgctatcgga   41940 gtaaccgagc aggtatgcgt cgtgcgccat gcgaggcctc cagggccggt cgtgcgggga   42000
gttccccacg gcaggtggcc aggggggctcc gcggtgtctg gagcactgag tgccctgtag   42060
cggccgtgcg gtgtggtccg gtgttccggg tatgtcacgc accggagcgg gacatgtacg   42120
tgtccgaagg cggcgggcgg cgcagagcct tgccgctgga ggtgcgtgcg atcccgccgc   42180
gccgcacgaa ctcgatcgtg tcgggtgtga tgcccagctc ggccaccaca cgtgcgcgga   42240
tgtgttgcgt cgtggcacga cggctcgcct cgtcgtgccg cgtcgtctcg acgacgagcc   42300
cgaggcggcc tccctcgtcg ctccagatct gctcggccag gacgccgtgg acgaggaggc   42360
cgggtgtgtc ccgcacgacc gcctcgatgt cgctcgccca gtggttcgcg ccgaagacga   42420
tgatcacctc tttcgtgcgg cccacgatgt acagctcgcc gtcgtgccac aggcccaggt   42480
caccggtcgc caaccagccg cccggaagga ggacgcgacg gctctcttcg gggtggcggt   42540
cgtacccggt gctcgtgacg gacgcccccc ggacctcgac ggcgccgacc gtgccgggca   42600
cggccggtgc gccgctcgcg gtggtgagcc ggacctcggt acgccgcacc ggcgttccca   42660
cactgaccag ttcgcgacac ggcccggcgc cggacggcac cggtacgtaa cggccccggt   42720
tcagttcgtc ccggtcggca cgcagcacct tggccgggcg gccgagggga gggaaggcga   42780
ccgccagggt cgcctccgcc agtccgtagg ccggcaggaa gacgttctcg gacagtccgg   42840
cgggcgcgaa acgtcggcg aaggcgtcct gaagccgccg gtcgaccggc tcggcgccgt   42900
tcaccgcgat gcgccagcgg gagagatcga ggcggccgg cggcgccgcg tcgcgcctca   42960
ggacgtagcg gtagccggag tcaggagcca tggtgaaggt cgcccccagc cgccccatgg   43020
cccggatcca gtcacccgga ctgcgcaggt agtcctccgg tgtcagcaga tggatgtcga   43080
```

```
cgtcgtgcag cagcggtgtc aagaaggaac cgatcaggcc catgtcgtgg aagaggggca   43140
gccaggtgca gccgacgtcg gtcctggcga gccgtgtgcc atgggcgatg gccgccaccc   43200
cggccgccac gttgccgtgg ctgagcacga cgccccgcgg ttcgctgctc gtgcccgacg   43260
tgtactgaac gacggccggg tccgacgccg cccgcgcgac gtgggccgcg gacggctcgg   43320
ccacctccgg caccaggagt acgtcgaccg ggcgggcgcc gtcggacagt ccaggaccga   43380
gcagcgggcg catggccgga gccgtcagca cggtccgtac ccgagagcgg cgcagggccg   43440
cggaggtgcg ccggagatag gcgtcggacg acccgaaggg cgcgggaccg ggcagcggca   43500
ccgcgaccgc gcccgccgcc agcacgccga agaaggcgcg cgcgaagtcc accgacgtcg   43560
gcaggacgag ggcgacccgc tcgccgggtc gcaccccgcg cgacagcagc cccgcggcca   43620 cccgccggc ctcggcgaag aggtcgctgt aggacagcgc gtcgccgtcc tggcccggc    43680 gcagcacgtg catgccccgt ccggagcctt gtgcggcgac gcggccgagc gcggcgaaca   43740
gggtcacgac agcggttccg tgccggcctc cgcgatcacc ttggtgatcg cggccgcgaa   43800
ctcccgcacg gtgctcgtct cgaagacgat gcggtcctcc acctcgatgt cgtagtgctg   43860
ctcgatctcc agcacgatct ggagcgcgtg gatcgagtcg aagcgcggca aggagcgcag   43920
atcggtgtcc acgcccacct cctcgacacc gatgcgcagt tgctcggcga cggatcggcg   43980
gacggtctgt tcgatgtcgg tgacactcgc ctgtgacatg gcgtggtgtt gtcctgttct   44040
gtgaggccgg cgcgtcgggg cgcggcggga ggcggacgcc gggactgacg gtcagcgagc   44100
gccgggccgg cgggccaggg cgcgcagctt ggctttgatg tcccgcgggg tctccaacga   44160
gtcgtcgtcc gccaggagcc ggacgatcga catcaccttg gcgtccgcgg cgtccaccga   44220
gtcgtgctgg atggtctcga tacgcggat gccggccgtg gatgtggaat gcgggtagaa   44280
catgcccgcc gggtgcttga cgccgttgct acggtccgcg agccagatgt aggccatgcg   44340
cagcgcggcg gcctgatggg ccggatcgct gtcgcacagt tccgcatga agacggagaa   44400 cgcacggcag tgccgggcct cgtcgcgggc caggagccgc cagattctgc ggatcaccgg   44460
ctccgacaca tgggcggcga gcgccttgta gagggcggac gcgcgtgact ccgagatcac   44520
gttcatcatg agggtggcgg agcgcacgtc gccctgcgga tacggctctc gtttgtagag   44580
cgcgtgcttc gaacggagtg agaccccgat ccggtccagg tagcgggcct ggaccagtga   44640
gtgccgggat tcctccgcac cccattgcag tgcccaggag gagaagctga cctcgtcctg   44700
ccattcccgc aggaagttgt gagcgccggg tagggtgccg aactcgatga cggccgcctc   44760
ggtgaggaag tccacggtcc gttcgtcgag catgccgtgc tcgatgcggt ccaggtccac   44820
ctcggtccag tcccagcgcg tcgtctcgaa ccagtcgaag atcttgttga aggtcatgtc   44880
gaggtagtag tcggtgtaga ggtcgtccgt catcagcgcg cggtgcgccc gcagggccag   44940
ttcgaccgag gtggtgaacc cttcgggcgc caccgcggcg ggccggacga tgtcctcgac   45000
gtccagtgct tccgcccagc cgggaaccgg gccgccgta tcgggcccga cgacgtacac    45060
ccgggtccgg ttgaacttcg agtgcgaccg cagcgcccgg acggcgggca gcggctcggc   45120
gtccgccccg atccacaccg ccgcgagctc ggatgacggt tcgaactcgt gcaggtagcg   45180
gtgccagtcg gcgtgtgccg gccggtccac ggtgacgtcg ccgaaggcgg ggacggtgag   45240
cctttcggcg ggggagactg cggtggtggg tgccagcagg gcgatggtgt gcggggggcac   45300 ggagggcgtc ctctctgtcg gtctgcgcag gccgtcggcg agcaccttgc cgcgcgttgt   45360
gtggggctcg gctccgtaac acgtgcgtgc cgcgacgtca gagccgcccg tactccgcgg   45420
```

```
cagggccgag gagtacgggc agcgcctcga tgctgttgct gacgaacgag ggcacgggcc    45480
gcacggtcca cgtgtcggac ggggccagcc gcacgtcggg gaaccgggtg aagaatccgg    45540
ccagtgccgt ctccagctgg agacgggcca ggtgtgtccc gatacagaag tgcgggccgt    45600
gcccgaagcc gaggtggccg gcctgccgcc ggcggacgtc gaagaggtcc gcgtccggcc    45660
cgtggtgcgc cgggtccggg cccgccgagc cgaaggacgc gaggatggct tctccccggt    45720
ggatcgtctg gccggcgatg acgacgtcct cggtcgggta gcgcatcggg aactggttca    45780
ccgcgccgtt ccagcgcatc gtctcctcga ccaccgcact ccacgggacc tccccggcgc    45840
gggcggaggc cagttgctcg gggtgggtga gcagcgcgtg gcaggcgttg acgagtacgt    45900
tgatgacgct ctggtggccg gcgaagaaca tcagcaggat catgccgtgc agttcgctgt    45960
cggtgagccg gtcgtctccg tcctggcgtg ccgtgagcag gacgctgatg aggtcgtccc    46020
gggggacgtc gcgacgttcg gcgacgatct cccggagcag cgcttcgatc cgtccgtcga    46080
tctcctggac ctgttcgggg gagttgttcg tacgggtctg catgccgtgg agcacgtgca    46140
gcagacgccg cttgcgctgc gggatcccca gcaggtccga gatgacggtg gtggggatgg    46200
ggtaggcgaa agccttgcgg agatccaccg gccggtcttc cggccgtgtg gcgagctggt    46260
cgaggagccc gtcgacgagg cgttccaccc ccgggcgcat ggcctccacc cgttccgggg    46320
tcagtgcctg gtcgaccagt ccgcgcagcc gccggtgatc cgcgccgtgc gaattgatga    46380
cgctgtcggt cgcgacgaag cccatcaacg gccacccgtc cggcacttcg ccgcgggccg    46440
ctgcctccca gtgcgtgatt cccttggcga ccctgggatc cgtcagcact cggcgcaggt    46500
cctcgtggtg cggaatcgcc cacgcccgca caccgccggg gagttggacc ggaacggctc    46560
tccccgccgc ccgcaggcgg gcgttctccg cgtgct                              46596
```

```
<210> SEQ ID NO 4
<211> LENGTH: 37
<212> TYPE: DNA
<213> ORGANISM: Artificial
<220> FEATURE:
<223> OTHER INFORMATION: Primer

<400> SEQUENCE: 4
cagagaattc gcggtacggg gcggacgaca aggtgtc                              37

<210> SEQ ID NO 5
<211> LENGTH: 39
<212> TYPE: DNA
<213> ORGANISM: Artificial
<220> FEATURE:
<223> OTHER INFORMATION: Primer

<400> SEQUENCE: 5
gcgcatgcat gtgccggtgc cggtccgcga gccgcttgg                            39

<210> SEQ ID NO 6
<211> LENGTH: 40
<212> TYPE: DNA
<213> ORGANISM: Artificial
<220> FEATURE:
<223> OTHER INFORMATION: Primer

<400> SEQUENCE: 6
cctcatgcat ctggaggacg tcgcaggtga attctgggcg                           40

<210> SEQ ID NO 7
<211> LENGTH: 33
```

```
<212> TYPE: DNA
<213> ORGANISM: Artificial
<220> FEATURE:
<223> OTHER INFORMATION: Primer

<400> SEQUENCE: 7
gggcaagctt ctcctggctg agcttgaaca tcg                                33

<210> SEQ ID NO 8
<211> LENGTH: 3994
<212> TYPE: DNA
<213> ORGANISM: Artificial
<220> FEATURE:
<223> OTHER INFORMATION: DNA fragment

<400> SEQUENCE: 8
cagaggatcc gcggtacggg gcggacgaca aggtgtcgtt gccgcgccgg cactcggact      60
ctcgcagcct cacaacgctg ctggccgcgg cggtgtacct cacgtcgcgg gcggtggacg     120
acgcgctgga tctgctgaag gtcctgatcg cgacgaagct tgcagaccgg ctgcacatcc     180
tggacggcgg tgctggacgc cacattcgaa aagcgcctgc tcaatacccg cccccaacgg     240
agacgaggtt gaacgacaag ctcagggcgt ctgagtactt cggttgagta gttctgccca     300 tgtgagggc agggccgtcg agacaggctg tgtacacaac gccgcggtgc gcagagcgct     360
cggcgaagag accagtagcg gtcatctatg aggggatact tcatgtccaa gcgccttgtc     420
gtctcgtcgc tcgccgtggc cgcagccgtc gttgccggca ccgtggtgtt cgtctcctcg     480
gccgacgccg ctgtgccggc caagccggag atctcaaagg ccaccgccca ctacaccagt     540
acggccggtg ggagcgcctc gctcaccttc agcgccaccg tggccgacaa ctccggaatc     600
aagagcctgc gggtgctcgc ctggccgcg agttcgggcc ttgcgcccac ggcgggcgag     660
atgcgggatg tcgaggaagc cacgtgcaag gcgacttccg cgacggcctc ggtgtgcacc     720
tacaccgtga agctcggc caaggaagcc gccgcgttgc caagggcgt ctggcacgta     780 tccgtgctgg ccaccgccaa ggaccacgac acgaccttcg cgcccaagg cgccacgttc     840 accgtcaagc actgacggct ccgccccgcc ggaatgatga tcgcggcccg cgcgccgggc     900
ggaccgtatc gcgacctcca ttggacccgt gaaccgcac gacgcggtga actccgccca     960
ccctgcccca gggcggacgg agttcacctg ggggcgacgc cgcgcatctg acgcgcgctg    1020
ccacgatgcc gcaccactcc gcgcgcgggc ggatgcaggc gaagtgactc ccagctcgac    1080
gcgctcgcca aacacggcat ctcgcgcgac tacatcttcg gcgagaagat cagcacccgg    1140
gcgcggggca gcccgaagtt ccgggaggag gcgctgaggg cggcgcggga ggtcaaggcg    1200
cacgccccac actgccgtgt catcttcacg gtgtacgagc ggaagcggct cggtcgcaac    1260
gccgccgaac tcaccgccct cgccgaccac ctcaccgccc acggcttggt cctggagata    1320
ttcgccgggc cctgtcgaag gactcccgga gccgtggaac ccggcgccca cccgacgcga    1380
cagcccgacg cggcagttgg ggcgctcccg gcgggcctgc ccggacaccg aaacgcccgg    1440
caccacaagc gaaagagcgt ccgtcggcaa gctgacgggt cctcatgaag gatttaggcc    1500
agtgatttgg gacacacccg aacgcgccgg ccggatctga ggaatcgcct agggcccgct    1560
cctatcggga acttgaagcc gccctgccga gccaacgctt gactccggtt ccggcggtgc    1620
ggatgacgat aatttccggt gagtctgccc aaaagggtac atagcgggcg catagaaaac    1680
tcttgcgagt gctgcgggtg gcttgtaggg tcctaatgaa tcggctggac aagggaaggt    1740
tgatgcgggc gtccgaacca aaatagcttc ggacagcaac tgctgccttc tgtcgatgga    1800
```

-continued

```
agtaggggga agttcgtgga aatcggctcg ggcgcgcccg aattaaccgc gtcgtcggtg    1860
tatcagcagc ggcgtgacca aatcgccgca agcgctgccg cctatgtgcc cggcgagccc    1920
attccagagg tcgagtacac ggacgccgag cacgctctgt ggcgcctggt ttccaagcgg    1980
ctcgcggacc ggcaccggca catgcatctg gaggacgtcg caggtgaatt ctgggcgtcc    2040
tgcgacgata catccattga aaactaatg gcggttgata tatgacccgg ctcgcagagc     2100
aatcatccac tgcgcagcag agcccggaat cagaagtact ggacgtcacc ggaatcggat    2160
tcggtgccgc gaatctcgcc ctggcggtgg cgctccatga atccgaagcc gccgggaagg    2220
cccttttcct ggagaagcag aaggaattcg gctggcatcg ggggatgctc ctgggggct    2280
cctcgctcca ggtgtccttt ctcaaggaca tcgccacgat gcgcaatccc accagtgatt    2340
tcggattcct gtcctatctc caggagaagg accggctggt cgacttcatc aaccagcaca    2400
ccctgctgcc ctcccggatc gagtaccacg actacctcca gtgggccgcc gaccggctga    2460
accacctggt cgagtacggc gtggaggcca ccggtgtgcg gccggtgacc gaagccggtg    2520
aggtcgtcgc gctcgacgtg ctcgccgggg accgggtggt cgcccggacc agaaacctcg    2580
tcctcgcctc cggcctgcgc ccccggctgc ccgagggcgc ggagaccggc gaacgcgtct    2640
ggcacagctc ccagttgctg caccggctgc ccgcgttcga cgaacgcccg ccccgccggg    2700
ccgtcgtggt cggcgccggc cagagcgcgg ccgaggtcgc cgcgcacctc atggaccgct    2760
acccgcaggc cgaggtgtgc gcggtgttcg cccgctacgg ctacagcgtc gccgactcca    2820
gcccgttcgc caaccgcgtc ttcgaccccg ccgccgtgga cgacttctac ttcgccccgc    2880
ccgaggtcaa gcaggccatc atgcgctacc acggcggcac caactacgcc gtcgtcgacg    2940
aggacgtcct ccagggcctc taccgccgcc agtacgagca gaaggtgtcc ggcgccccgc    3000
ggctgcgggt gatgaacgcc tcccgcctgg tgtccgtcga accgcgccag gaatccgccg    3060
ccgtacgcgt ggagttcctg cccacgggcg aacacaccga cctggacgcc gacctggtcg    3120
tgtacgccac cggtacgac tccaccgacc cggccgaact gctcggcggc gtctccggcg     3180
ccctccgccg ggacgaggcg ggggagttgc tgatcggccg cgactaccgg ctcggcacca    3240
ccggggattt ccggtgcggc atctacgtcc agggcgccac cgaggcgacc cacggcatcg    3300
cctccaccct gctgtccatg gtggcggtcc gcgcgggcga gatcgccggg tcgatcaccg    3360
gcggccggtg cgacccggac cgctccaccg gaagcaaggc agcagcgggg aacagggct    3420
gaagtgtacg aacgtccgct gtaccgggag gattgcgacg cgtcgtcct ggcgtttctg     3480
cgacacaacc cactggcaat ggtcgtcacc tcgcacgacg acgtcccggt ggccaccca     3540
gcgccggtgc tgttccggca cggacccgac ggcgccgacg ccgaggccgt cgccgcgggc    3600
accgtcccgc tcgccggctc caccctgatc ggccacatga acgtcgagaa cccgcagtgg    3660
cgccggatgc gctccggcga ccgggcgctc atcgtcttcc agggcccgca cggctatgtc    3720
tcgccgacgg tctacggggt cacgcccgcg gccccacct gggacttcat cgccgtccac    3780
gtgaacggca cagtggagcc caccgccgac cccgccgccg tgctggacat cgtctccgac    3840
accgccggc ggctgagtc cggcttcggg cgcggctggg accaggagtc ctccctcgac     3900
tacttccgcc agatcgcgcc cggcgtgggc gccttcaccc tgcgggtcga ttccgtgcag    3960
acgatgttca agctcagcca ggagtctaga gccc                                3994
```